US007169603B2

(12) United States Patent
Hedley et al.

(10) Patent No.: US 7,169,603 B2
(45) Date of Patent: Jan. 30, 2007

(54) α-MSH RELATED COMPOUNDS AND METHODS OF USE

(75) Inventors: Mary Lynne Hedley, Lexington, MA (US); Robert G. Urban, Lexington, MA (US); Nazneen Aziz, Lexington, MA (US); Hongmin Chen, Framingham, MA (US); Bijan Etemad-Moghadam, Jamaica Plain, MA (US); Peng Yin, Newton, MA (US)

(73) Assignee: MGI Pharma Biologics, Inc., Lexington, MA (US)

( * ) Notice: Subject to any disclaimer, the term of this patent is extended or adjusted under 35 U.S.C. 154(b) by 871 days.

(21) Appl. No.: 09/906,206

(22) Filed: Jul. 16, 2001

(65) Prior Publication Data
US 2005/0239170 A1    Oct. 27, 2005

Related U.S. Application Data

(60) Provisional application No. 60/298,317, filed on Jun. 14, 2001, provisional application No. 60/258,764, filed on Dec. 29, 2000, provisional application No. 60/238,380, filed on Oct. 6, 2000, provisional application No. 60/226,382, filed on Aug. 18, 2000, provisional application No. 60/218,381, filed on Jul. 14, 2000.

(51) Int. Cl.
*C12N 1/00* (2006.01)
*C12P 21/02* (2006.01)
*C07H 21/00* (2006.01)

(52) U.S. Cl. ............. 435/320.1; 435/69.7; 435/69.1; 536/23.1; 536/23.4; 536/24.1

(58) Field of Classification Search ............ None
See application file for complete search history.

(56) References Cited

U.S. PATENT DOCUMENTS

| | | | | |
|---|---|---|---|---|
| 4,675,382 A | | 6/1987 | Murphy | 530/350 |
| 5,374,548 A | * | 12/1994 | Caras | 424/450 |

FOREIGN PATENT DOCUMENTS

| | | | |
|---|---|---|---|
| WO | WO 90/06369 | * | 6/1990 |
| WO | WO 93/02692 | | 2/1993 |
| WO | WO 99/57148 | * | 11/1999 |
| WO | WO 99/60135 | | 11/1999 |
| WO | WO 00/33658 | | 6/2000 |
| WO | WO 00/42856 | | 7/2000 |

OTHER PUBLICATIONS

Kezuka T, Streilein JW. Invest Ophthalmol Vis Sci. Jun. 2000;41(7):1803-11. In vitro generation of regulatory CD8+ T cells similar to those found in mice with anterior chamber-associated immune deviation.*
Brandenburger et al. J Recept Signal Transduct Res. Jan.-Jul. 1999; 19: 467-480.*
Dorr et al. Life Sci. 1996;58(20):1777-84.*
Airaghi et al., "Elevated concentrations of plasma α-melanocyte stimulating hormone are associated with reduced disease progression in HIV-infected patients," Lab. Clin. Med. 133(3):309-315 (Mar. 1999).
Catania et al., "The Neuropeptide α-MSH in HIV Infection and Other Disorders in Humans," Ann. NY Acad. Sci., 840:848-856 (1998).
Cone et al., "The Melanocortin Receptors: Agonists, Antagonists, and the Hormonal Control of Pigmentation," Recent Progress in Hormone Res., 51:287-318 (1996).
Cool et al., "Carboxypeptidase E Is a Regulated Secretory Pathway Sorting Receptor: Genetic Obliteration Leads to Endocrine Disorders in $Cpe^{fat}$ Mice," CELL, 88(1):73-83(Jan. 10, 1997).
Fan et al., "Role of melanocortinergic neurons in feeding and the agouti obesity syndrome," NATURE, 385(6612):165-168 (Jan. 9, 1997).
Funasaka et al., "Expression of Proopiomelanocortin, Corticotropin-Releasing Hormone (CRH), and CRH Receptor in Melanoma Cells, Nevus Cells, and Normal Human Melanocytes," J. Invest. Dermatol. Symp. Proc., 4(2):105-109 (Sep. 1999).
Hohmann et al., "Differential role of melanocortins in mediating leptin's central effects on feeding and reproduction," Amer. J. Physiol., 278(1):R50-R59 (Jan. 2000).
Ichiyama et al., "Autocrine α-Melanocyte-Stimulating Hormone Inhibits NF-κB Activation in Human Glioma," J. Neurosci. Res., 58(5):684-689 (Dec. 1, 1999).
Joosten et al., "Alpha-Melanocyte Stimulating Hormone Promotes Regrowth of Injured Axons in the Adult Rat Spinal Cord," J. Neurotrauma, 16(6):543-553 (1999).

(Continued)

Primary Examiner—Elizabeth Kemmerer
Assistant Examiner—Christina Borgeest
(74) Attorney, Agent, or Firm—Fish & Richardson P.C.

(57) ABSTRACT

The invention provides polypeptides containing α-MSH that can be used to treat diseases characterized by inflammation and/or autoimmunity. Also included in the invention are α-MSH analogs and nucleic acids encoding polypeptides containing α-MSH and α-MSH analogs optionally linked to heterologous sequences. Also included in the invention are methods of delivering α-MSH containing peptides, α-MSH analogs, an DNA encoding α-MSH and α-MSH analogs.

12 Claims, 29 Drawing Sheets

OTHER PUBLICATIONS

Kim et al., "ARC POMC mRNA and PVN α-MSH are lower in obese relative to lean Zucker rats," Brain Res., 862:11-16 (Apr. 2000).

Korner et al., "Regulation of Hypothalamic Proopiomelanocortin by Leptin in Lean and Obese Rats," NEUROENDOCRINOLOGY, 70:377-383 (Dec. 1999).

Krude et al., "Severe early-onset obesity, adrenal insufficiency and red hair pigmentation caused by *POMC* mutations in humans," Nature Genetics, 19(2):155-157 (Jun. 1998).

Lankhorst et al., "Functional Recovery After Central Infusion of α-Melanocyte-Stimulating Hormone in Rats with Spinal Cord Contusion Injury," J. Neurotrauma, 16(4):323-331 (1999).

Lankhorst et al., "Combined treatment with a MSH and methylprednisolone fails to improve functional recovery after spinal injury in the rat," Brain Research, 859:334-340 (2000).

Marsh et al., "Response of melanocortin-4 receptor-deficient mice to anorectic and orexigenic peptides," Nature Genetics, 21:119-122 (Jan. 1999).

McMinn et al., "Effect of intracerebroventricular α-MSH on food intake, adiposity, c-Fos induction, and neuropeptide expression," Amer. J. Physiology, 279(2):R695-R703 (Aug. 2000).

Mountjoy et al., "Obesity, Diabetes and Functions for Proopiomelanocortin-derived Peptides," Mol. Cell Endocrinol., 128(1,2):171-177 (1997).

Rheins et al., "Alpha-Melanocyte Stimulating Hormone Modulates Contact Hypersensitivity Responsiveness in C57/BL6 Mice," J. Investigative Dermatology, 93(4):511-517 (Oct. 1989).

Saperstein et al., "Interlekin 1β Mediates Stress-Induced Immunosuppression Via Corticotropin-Releasing Factor," Endocrinol., 130(1):152-158 (Jan. 1992).

Schwartz et al., "Leptin Increases Hypothalamic Pro-opiomelanocortin mRNA Expression in the Rostral Arcuate Nucleus," Diabetes, 46(12):2119-2123 (Dec. 1997).

Tam et al., "The amino-terminal sequence of pro-opiomelanocortin directs intracellular targeting to the regulated secretory pathway," Eur. J. Cell Biol., 62(2):294-306 (Dec. 1993).

Taylor et al., "Alpha-Melanocyte-Stimulating Hormone Suppresses Antigen-Stimulated T Cell Production of Gamma-Interferon," NEUROIMMUNOMODULATION, 1:188-194 (1994).

Thiele et al., "Central infusion of melanocortin agonist MTII in rats: assessment of c-Fos expression and taste aversion," Amer. J. Physiol., 274(1):R248-R254 (Jan. 1998).

Vergoni et al., "Chronic melanocortin 4 receptor blockage causes obesity without influencing sexual behavior in male rats," J. Endocrinology, 166(2):419-426 (Aug. 2000).

Yaswen et al., "Obesity in the mouse model of pro-opiomelanocortin deficiency responds to peripheral melanocortin," Nature Medicine, 5(9):1066-1070 (Sep. 1999).

Yeo et al., "The role of melanocortin signalling in the control of body weight: evidence from human and murine genetic models," QJMed., 93(1):7-14 (Jan. 2000).

Zemel & Shi, "Pro-opiomelanocortin (POMC) Deficiency and Peripheral Melanocortins in Obesity," Nutr. Rev., 58(6):177-180 (Jun. 2000).

"Oklahoma Medical Research Foundation: Obesity Breakthrough: Lessons From Fat Yellow Mice" http://www8.techmall.com/techdocs/TS990830-4.html (1999).

"Mutant Mice Provide Insight Into Obesity" http://www.omrf.ouhsc.edu/omrf/news_releases/releases/19990831b.asp (1999).

"Worth the Weight" omrf.ouhsc.edu/omrf/news_releases/releases/19990831.asp (1999).

Bishai et al. (1987) "High-level expression of a proteolytically sensitive diphtheria toxin fragment in *Escherichia coli*" J. Bacteriol. 169(11):5140-51.

Rajora et al. (1997) "Alpha-MSH modulates experimental inflammatory bowel disease" Peptides 18(3):381-85.

Taylor et al. (2000) "Alpha-melanocyte stimulating hormone (α-MSH) induction of regulatory autoreactive T cells" FASEB Journal 14(6):A1112, Abstract No. 140.5.

Mizuno et al., "Hypothalmaic pro-opiomelanocortin mRNA is reduced by fasting and in *ob/ob* and *db/db* mice, but is stimulated by leptin," Diabetes, 47:696 (1998).

* cited by examiner (SEQ ID NO:43) aagcttgcgctgcctggaag (SEQ ID NO:42) atg ccg aga tcg tcg tgc agc cgc tcg ggg gcc ctg ttg ctg gcc ttg ctg ctt cag gcc
M   P   R   S   C   C   S   R   S   G   A   L   L   L   A   L   L   L   Q   A tcc atg gaa gtg cgt ggc tgg tgc ctg gag agc agc cag tgt cag gac ctc acc acg gaa
S   M   E   V   R   G   W   C   L   E   S   S   Q   C   Q   D   L   T   T   E agc aac ctg gag tgc atc cgg gcc tgc aag ccc cgc gag ggc aag cgc tcc tac tcc
S   N   L   E   C   I   R   A   C   K   P   R   E   G   K   R   S   Y   S atg gag cac ttc cgc tgg ggc aag ccg gtg taa ggatccctcgag
<u>M   E   H   F   R   W   G   K   P   V</u>

FIG. 2A (SEQ ID NO:46) aagcttgcgcgctgcctgaag (SEQ ID NO:47) atg ccg aga tcg tgc tgc agc cgc tcg ggg gcc ctg ttg ctg gcc ttg ctt cag gcc
M   P   R   S   C   C   S   R   S   G   A   L   L   L   A   L   L   Q   A tcc atg gaa gtg cgt ggc tgg tgc ctg gag agc agc cag tgt cag gac ctc acc acg gaa
S   M   E   V   R   G   W   C   L   E   S   S   Q   C   Q   D   L   T   T   E agc aac ctg ctg gag tgc atc cgg gcc tgc aag ccc cgc gag ggc aag cgc tcc tac tcc
S   N   L   L   E   C   I   R   A   C   K   P   R   E   G   K   R   S   Y   S atg gag cac ttc cgc tgg ggc aag ccg gtg GGC taa ggatccctcgag
<u>M   E   H   F   R   W   G   K   P   V   G</u>

FIG. 2B (SEQ ID NO:48)  aagcttgcgcctgcctgaag (SEQ ID NO:49)
```
atg ccg aga tcg tgc tgc agc cgc tcg ggg gcc ctg ttg ctg gcc ttg ctg ctt cag gcc
 M   P   R   S   C   C   S   R   S   G   A   L   L   L   A   L   L   L   Q   A tcc atg gaa gtg cgt ggc tgg tgc ctg gag agc agc cag tgt cag gac ctc acc acg gaa
 S   M   E   V   R   G   W   C   L   E   S   S   Q   C   Q   D   L   T   T   E agc aac ctg ctg gag tgc atc cgg gcc tgc aag ccc cgc gag ggc aag cgc tcc tac tcc
 S   N   L   L   E   C   I   R   A   C   K   P   R   E   G   K   R   S   Y   S atg gag cac ttc cgc tgg ggc aag ccg gtg GCC AAG AAG taa ggatccctcgag
 M   E   H   F   R   W   G   K   P   V   G   K   K
```

FIG. 2C (SEQ ID NO:50) aagcttgcgcgctgcctgaag (SEQ ID NO:51) atg ccg aga tcg tgc agc cgc tcg ggg gcc ctg ttg ctg ctt cag gcc
              M   P   R   S   C   S   R   S   G   A   L   L   L   L   Q   A tcc atg gaa gtg cgt ggc tgg tgc ctg gag agc agc cag tgt cag gac ctc acc acg gaa
 S   M   E   V   R   G   W   C   L   E   S   S   Q   C   Q   D   L   T   T   E agc aac ctg gag tgc atc cgg gcc tgc aag ccc cgc gag ggc aag cgc tcc tac tcc
 S   N   L   E   C   I   R   A   C   K   P   R   E   G   K   R   S   Y   S atg gag cac ttc cgc tgg ggc aag ccg gtg GCC AAG AAG CGG taa ggatccctgag
 M   E   H   F   R   W   G   K   P   V   G   K   K   R

FIG. 2D (SEQ ID NO:79) aagcttgcgctgcctgaag (SEQ ID NO:78) atg ccg aga tcg tgc agc cgc tcg ggg gcc ctg ttg ctg gcc ttg ctg ctt cag gcc
M P R S C C S R S G A L L L A L L L Q A tcc atg gaa gtg cgt ggc tgg tgc ctg gag agc agc cag tgt cag gac ctc acc acg gaa
S M E V R G W C L E S S Q C Q D L T T E agc aac ctg ctg gag tgc atc cgg gcc tgc aag ccc cgc gag ggc aag cgc tcc tac tcc
S N L L E C I R A C K P R E G K R S Y S atg gag cac ttc cgc tgg ggc aag ccg gtg CGG TTC AAG CGG taa ggatccctcgag
M E H F R W G K P V R S K R

FIG. 2E

| CONSTRUCTS / α-MSH | pCMV-ssMSH | pZYC-ssMSH | pIRES-2X ssMSH |
|---|---|---|---|
| B16/F10 MOUSE MELANOMA | 780 | 992 | 1073 |
| GH3 RAT PITUITARY | 1600 | 3000 | 3200 |
| RAW MOUSE MACROPHAGE | 25 | 40 | 100 |
| 293T HUMAN KIDNEY | 0 | 0 | 0 |
| 3T3 MOUSE FIBROBLAST | 0 | 0 | 0 |

FIG. 9

| | |
|---|---|
| SHI95 | <320 pg/ml |
| SMI95 | <320 pg/ml |
| HLFα (H9) | >5,000 pg/ml |
| MLFα (M2) | >5,000 pg/ml |

FIG. 10

α-MSH RELATED COMPOUNDS AND METHODS OF USE

CROSS REFERENCE TO RELATED APPLICATIONS

This application claims priority from U.S. Provisional Application No. 60/218,381, filed Jul. 14, 2000, U.S. Provisional Application No. 60/226,382, filed Aug. 18, 2000, U.S. Provisional Application No. 60/238,380, filed Oct. 6, 2000, U.S. Provisional Application No. 60/258,764, filed Dec. 29, 2000, and U.S. Provisional Application No. 60/298,317, filed Jun. 14, 2001. These applications are incorporated herein by reference in their entirety.

FIELD OF THE INVENTION

The invention relates to alpha-MSH compounds and methods of use.

BACKGROUND

Pro-opiomelanocortin (POMC) is a precursor of various bioactive peptides, including adrenocorticotropic hormone (ACTH) and alpha MSH (α-MSH). α-MSH and ACTH are members of the melanocortin family, which also includes β-MSH and γ-MSH. POMC contains eight pairs of basic amino acids and one sequence of four basic amino acids, which are the sites of cleavage for the enzymes prohormone convertase 1 (PC1) and prohormone convertase 2 (PC2). Specifically, PC1 cleaves the POMC polypeptide to yield ACTH(1-39), which is in turn cleaved by PC2 to yield ACTH(1-17), which is further cleaved by PC2 to result in ACTH(1-14). A 13 amino acid α-MSH peptide is generated by the action of peptidylglycine alpha-amidating monooxygenase, which results in a C-terminally amidated α-MSH peptide. ACTH(1-17) contains the consensus amidation signal of Gly-Lys-Lys immediately carboxy the valine residue at position 13. This valine residue is subject to amidation in α-MSH and ACTH peptides. Further enzymatic modifications including N-alpha-acetylation by opiomelanotropin-acetyltransferase can occur during or after proteolytic processing. α-MSH and ACTH can be produced in amidated or non-amidated forms, as well as des-acetylated, mono-acetylated or di-acetylated forms. C-terminal amidation and/or N-terminal acetylation may contribute to the biological activity of α-MSH and/or ACTH peptides.

Under normal conditions the level of α-MSH is tightly regulated, having a half-life in the circulation on the order of a few minutes (Lipton et al. (1990) Yale J. Biol. Med. 63:173). α-MSH is found in the circulation of normal individuals at a level of about 21 pg/ml. α-MSH is also found in the aqueous humor of the eye (Taylor et al. (1992) Curr. Eye Res. 11:1199), cerebral spinal fluid (Taylor et al. (1996) Neuroimmunomod. 3:112), in skin (Luger et al. (1997) J. Invest. Dermatol. Symp. Proc. 2:87), and at sites of inflammation such as the synovial fluid of arthritic human joints (Catania et al. (1994) Neuroimmunomod. 1:321).

α-MSH and its carboxy terminal tripeptide act as in vivo and in vitro regulators of inflammation (Cannon et al. (1986) J Immunol. 137:2232; Robertson et al. (1986) Inflammation 10:371; U.S. Pat. No. 5,028,592). The mode of action of α-MSH appears to be via interference with NF-kB activation (Ichiyama et al. (1999) J Neuroimmun. 99:211). In vivo administration of α-MSH or the tripeptide α-MSH 11–13 inhibits LPS-mediated brain inflammation by preventing inactivation of I-κB and subsequent activation of NF-κB (Ichiyama et al. (1999) Brain Res. 836:31). NF-kB is a transcription factor that is necessary for the transcription of proinflammatory cytokines, including γIFN (Baeuerle et al. (1994) Ann Rev Immunol. 12:141).

SUMMARY OF THE INVENTION

The invention is based on the discovery that fusion polypeptides containing α-MSH can be used to elicit a variety of biological responses, in vitro and in vivo.

In one aspect, the invention features a polypeptide, or a nucleic acid sequence encoding a polypeptide, wherein the polypeptide contains an α-MSH concatamer. The polypeptide can further include a trafficking sequence, e.g., a signal sequence. In one embodiment, the signal sequence contains the pro-opiomelanocortin (POMC) signal sequence or a portion thereof that directs the secretion of the polypeptide when expressed in a mammalian cell. Alternatively, the trafficking sequence can direct the α-MSH concatamer to an endosome, nucleus, or a lysosome. In another embodiment, the trafficking sequence can direct secretion of the α-MSH concatamer.

A polypeptide containing an α-MSH concatamer can further include a linker between two α-MSH units of the α-MSH concatamer. The linker can optionally include a protease cleavage site, e.g., a protease cleavage site specific for a cell associated protease or a serum protease.

A polypeptide containing an α-MSH concatamer can further include a membrane sequence. The membrane sequence can include the membrane domain or a portion of the membrane domain of a naturally occurring protein, e.g., a human protein, e.g., the transferrin receptor. The polypeptide optionally includes a linker between the α-MSH concatamer and the membrane sequence. The linker can include a protease cleavage site. The polypeptide can further include a signal sequence and/or a cytoplasmic domain.

A polypeptide containing an α-MSH concatamer can further include a glycosylphosphatidylinositol (GPI) attachment signal peptide. The polypeptide optionally includes a linker between two α-MSH units of the α-MSH concatamer. The linker can contain a protease cleavage site.

In one embodiment, a polypeptide containing an α-MSH concatamer can further include a therapeutic polypeptide. Examples of therapeutic polypeptides include α-gliadin, basement membrane collagen, collagen, albumin, islet autoimmune antigen (IAA), insulin, thyroid stimulating hormone (TSH) receptor, thyroglobulin, voltage-gated potassium channels, glutamic acid decarboxylase (GAD), insulin receptor, insulin associated antigen (IA-w), heat shock protein (Hsp), synaptogamin in voltage-gated calcium channels, myelin basic protein (MBP), proteolipid protein (PLP), myelin oligodendrocyte-associated protein (MOG), αB-crystallin, acetyl choline receptor, RNA-binding protein HuD, PeV antigen complex, desmoglein (DG), dihydrolipoamide acetyltransferase, pyruvate dehydrogenase complex 2 (PDC-E2), DNA topoisomerase, RNA polymerase, immunoglobulin Fc, collagen, topoisomerase I, interphotoreceptor retinoid-binding protein, and S antigen (rod out segment).

In another aspect, the invention features a polypeptide, or a nucleic acid sequence encoding a polypeptide, wherein the polypeptide includes α-MSH and a membrane sequence. The membrane sequence can include the membrane domain or a portion of the membrane domain of a naturally occurring protein, e.g., a human protein, e.g., the transferrin receptor. The polypeptide can further include a linker between α-MSH and the membrane sequence. The linker can contain a protease cleavage site.

A polypeptide containing α-MSH and a membrane sequence can further include a signal sequence, a cytoplasmic domain, and/or a therapeutic polypeptide, as described herein.

In another aspect, the invention features a polypeptide, or a nucleic acid sequence encoding a polypeptide, wherein the polypeptide includes α-MSH and a signal sequence. The signal sequence can direct secretion of the polypeptide. In one embodiment, the signal sequence contains the pro-opiomelanocortin (POMC) signal sequence or a portion thereof that directs the secretion of the polypeptide when expressed in a mammalian cell. For example, the polypeptide can include the sequence

```
MPRSCCSRSGALLLALLLQASMEVRGWCLESSQCQD    (SEQ ID NO:42)
LTTESNLLECIRACKPREGKRYSMEHFRWGKPV,

MPRSCCSRSGALLLALLLQASMEVRGWCLESSQCQD    (SEQ ID NO:47)
LTTESNLLECIRACKPREGKRSYSMEHFRWGKPVG,

MPRSCCSRSGALLLALLLQASMEVRGWCLESSQCQD    (SEQ ID NO:49)
LTTESNLLECIRACKPREGKRSYSMEHFRWGKPVGK
K,

MPRSCCSRSGALLLALLLQASMEVRGWCLESSQCQD    (SEQ ID NO:51)
LTTESNLLECIRACKPREGKRSYSMEHFRWGKPVGK
KR, or

MPRSCCSRSGALLLALLLQASMEVRGWCLESSQCQD    (SEQ ID NO:78)
LTTESNLLECIRACKPREGKRSYSMEHFRWGKPVRS
KR.
```

A polypeptide of the invention can further include a linker, as described herein, between α-MSH and the signal sequence. The polypeptide can include a secreted peptide, e.g., human or murine serum albumin, or a portion thereof that directs secretion of the polypeptide. For example, the polypeptide can include the sequence

```
MKWVTFISLLFLFSSAYSRGVFRRDAHKSEVAHRKD    (SEQ ID NO:59)
LGEENFKALVLIAFAQYLQQCPFEDHVKLVNEVTEF
AKTCVADESAENCDKSLHTLFGDKLCTVATLRETYG
EMADCCAKQEPERNECFLQHKDDNPNLPRLVRPEVD
VMCTAFHDNEETFLKKYLYEIARRHPYFYAPELLFF
AKRYKAAFTECCQAADKAACLLPKLDELRDEGKASS
AKGGYGGRIRRSYSMEHFRWGKPV,

MKWVTFISLLFLFSSAYSRGVFRRDAHKSEVAHRFK    (SEQ ID NO:70)
DLGEENFKALVLIAFAQYLQQCPFEDHVKLVNEVTE
FAKTCVADESAENCDKSLHTLFGDKLCTVATLRETY
GEMADCCAKQEPERNECFLQHKDDNPNLPRLVRPEV
DVMCTAFHDNEETFLKKYLYEIARRHPYFYAPELLF
FAKRYKAAFTECCQAADKAACLLPKLDELRDEGKAS
SAKGGYGGRIRRSYSMEHFRWGKPVG,

MKWVTFISLLFLFSSAYSRGVFRRDAHKSEVAHRFK    (SEQ ID NO:71)
DLGEENFKALVLIAFAQYLQQCPFEDHVKLNEVTEF
AKTCVADESAENCDKSLHTLFGDKLCTVATLRETYG
EMADCCAKQEPERNECFLQHKDDNPNLPRLVRPEVD
VMCTAFHDNEETFLKKYLYEIARRHPYFYAPELLFF
AKRYKAAFTECCQAADKAACLLPKLDELRDEGKASS
AKGGYGGRIRRSYSMEHFRWGKPVGKK,

MKWVTFISLLFLFSSAYSRGVFRRDAHKSEVAHRKD    (SEQ ID NO:72)
LGEENFKALVLIAFAQYLQQCPFEDHVKLVNEVTEF
AKTCVADESAENCDKSLHTLFGDKLCTVATLRETYG
EMADCCAKQEPERNECFLQHKDDNPNLPRLVRPEVD
VMCTAFHDNEETFLKKYLYEIARRHPYFYAPELLFF
AKRYKAAFTECCQAADKAACLLPKLDELRDEGKASS
AKGGYGGRIRRSYSMEHFRWGKPVGKR,

MKWVTFISLLFLFSSAYSRGVFRRDAHKSEVAHRRK    (SEQ ID NO:73)
```

```
                -continued
DLGEENFKALVLIAFAQYLQQCPFEDHVKLVNEVTE
FAKTCVADESAENCDKSLHTLFGDKLCTVATLRETY
GEMADCCAKQEPERNECFLQHKDDNPNLPRLVRPEV
DVMCTAFHDNEETFLKKYLYEIARRHPYFYAPELLF
FAKRYKAAFTECCQAADKAACLLPKLDELRDEGKAS
SAKGGYGGRIRRSYSMEHFRWGKPVRSKR, MKWVTFISLLFLFSSAYSRGVFRRDAHKSEVAHRFK    (SEQ ID NO:60)
DLGEENFKALVLIAFAQYLQQCPFEDHVKLVNEVTE
FAKTCVADESAENCDKSLHTLFGDKLCTVATLRETY
GEMADCCAKQEPERNECFLQHKDDNPNLPRLVRPEV
DVMCTAFHDNEETFLKKYLYEIARRHPYFYAPELLF
FAKRYKAAFTECCQAADKAACLLPKLDELRDEGKAS
SAKGGYGGRIRRSYSMEHFRWDEGKASSAKGGYGGR
IRRSYSMEHFRWKGPV, MKWVTFLLLLFVSGSAGSRGVFRREAHKSEIAHRYN   (SEQ ID NO:61)
DLGEQHFKGLVLIAFSQYLQKCSYDEHAKLVQEVTD
FAKTCVADESAANCDKSLHTLFGDKLCAIPNLRENY
GELADCCTKQEPERNECFLQHKDDNPSLPPFERPEA
EAMCTSFKENPTTFMGHYLHEVARRHPYFYAPELLY
YAEQYNEILTQCCAEADKESCLTPKLDGVKEKALVS
SVRGGYGGRIRRSYSMEHFRWGKPV, MKWVTFLLLLFVSGSAFSRGVFRREAHKSEIAHRYN   (SEQ ID NO:74)
DLGEQHFKGLVLIAFSQYLQKCSYDEHAKLVQEVTD
FAKTCVADESAANCDKSLHTLFGDKLCAINPNLREN
YGELADCCTKQEPERNECFLQHKDDNPSLPPFERPE
AEMCTSFKENPTTFMGHYLHEVARRHPYFYAPELLY
YAEQYNEILTQCCAEADKESCLTPKLDGVKEKALVS
SVRGGYGGRIRRSYSMEHFRWGKPVG, MKWVTFLLLLFVSGSAFSRGVFRREAHKSEIAHRYN   (SEQ ID NO:75)
DLGEQHFKGLVLIAFSQYLQKCSYDEHAKLVQEVTD
FAKTCVADESAANCDKSLHTLFGDKLCAIPNLRENY
GELADCCTKQEPERNECFLQHKDDNPSLPPFERPEA
EAMCTSFKENPTTFMGHYLHEVARRHPYFYAPELLY
YAEQYNEILTQCCAEADKESCLTPKLDGVKEKALVS
SVRGGYGGRIRRSYSMEHFRWGKPVGKK, MKWVTFLLLLFVSGSAGSRGVFRREAHKSEIAHRYN   (SEQ ID NO:76)
DLGEQHFKGLVLIAFSQYLQKCSYDEHAKLVQEVTD
FAKTCVADESAANCDKSLHTLFGDKLCAIPNLRENY
GELADCCTKQEPERNECFLQHKDDNPSLPPFERPEA
EAMCTSFKENPTTFMGHYLHEVARRHPYFYAPELLY
YAEQYNEILTQCCAEADKESCLTPKLDGVKEKALVS
SVRGGYGGRIRRSYSMEHFRWGKPVGKKR, or MKWVTFLLLLFVSGSAFSRGVFRREAHKSEIAHRYN   (SEQ ID NO:77)
DLGEQHFKGLVLIAFSQYLQKCSYDEHAKLVQEVTD
FAKTCVADESAANCDKSLHTLFGDKLCAIPNLRENY
GELADCCTKQEPERNECFLQHKDDNPSLPPFERPEA
EAMCTSFKENPTTFMGHLYHEVARRHPYFYAPELLY
YAEQYNEILTQCCAEADKESCLTPKLDGVKEKALVS
SVRGGYGGRIRRSYSMEHFRWGKPVRSKR.
```

The polypeptide can further include a therapeutic polypeptide described herein.

In another aspect, the invention features a polypeptide, or a nucleic acid sequence encoding a polypeptide, wherein the polypeptide includes α-MSH and a GPI attachment signal peptide. The polypeptide optionally includes a linker between α-MSH and the GPI attachment signal peptide. The linker can include, for example, a furin cleavage site. The polypeptide can further include a therapeutic polypeptide.

The invention also features an expression vector encoding a polypeptide as described herein. Examples of expression vectors include a plasmid, a viral genome or portion thereof, and a bacterial genome or portion thereof. Expression vectors also include linear or circularized nucleic acids containing promoter elements, α-MSH encoding units, and transcription terminators with RNA processing signals (e.g. polyadenylation sequences).

The invention also features a method of making a polypeptide. This method includes maintaining a cell containing an expression vector containing a nucleic acid of the invention under conditions permitting expression of the encoded polypeptide.

In another aspect, the invention features a method of treatment including delivering a nucleic acid, polypeptide, or analog as described herein to an individual, e.g., a mammal such as a human or mouse, suffering from, or at risk of, a disorder of the immune or nervous system. The method optionally includes a step (prior to the delivery step) of identifying an individual as suffering from, or at risk of, a disorder of the immune or nervous system. In this method, the α-MSH composition preferably mediates an immunomodulatory or neuro-modulatory function, e.g., an anti-inflammatory function, when delivered to the individual.

The compositions of the invention can be used to effect a wide variety of immunomodulatory functions, e.g., to inhibit the activity of various cells and/or molecules of the immune system. For example, the α-MSH compositions can be used to inhibit histamine release from mast cells, neutrophil chemotaxis and/or migration to an inflamed site, macrophage activation, or the expression of costimulatory surface markers, e.g., CD86 and/or CD40, by antigen presenting cells. The compositions may also induce the secretion of TGFβ or IL-10 by cells.

In one example of a method of treatment, the individual has an inflammatory disorder, e.g., rheumatoid arthritis, asthma, sepsis, cirrhosis, dermatitis, psoriasis, contact hypersensitivity, inflammatory bowel disease, or autoimmune encephalitis. In another example, the individual has an autoimmune disorder, e.g., diabetes, rheumatoid arthritis, multiple sclerosis, lupus, uveitis, or coleiac disease. In another example, the individual is a candidate for, or has received an organ transplant. In another example, the individual is on chronic dialysis. In another example, the individual has damage to neurons, e.g., spinal cord injury or Alzheimer's disease. In another example the individual has obesity. A nucleic acid or polypeptide can be delivered to the individual via any of the following routes: pulmonary, intravenous (e.g., portal or tail vein), nasal, subcutaneous, intramuscular, rectal, vaginal, intra-arterial (e.g., hepatic artery), transmucosal, and/or oral.

In another aspect, the invention features a composition containing a polypeptide including an α-MSH concatamer. This composition can further include a membrane sequence, a signal sequence, a GPI attachment signal peptide, and/or a therapeutic compound, e.g., a therapeutic polypeptide. Other compositions of the invention include: (1) an α-MSH containing peptide and a membrane sequence; (2) an α-MSH containing peptide and a signal sequence; and (3) an α-MSH containing peptide and a GPI attachment signal peptide. Any of these compositions can further include a therapeutic compound. The therapeutic compound can be attached to the polypeptide, e.g., as a fusion polypeptide. Alternatively, the therapeutic compound and polypeptide can be mixed in a single composition, though not attached to each other.

The invention also features a composition comprising a delivery vehicle and a nucleic acid and/or polypeptide of the invention. Examples of delivery vehicles include a depot, a microparticle, a liposome, a suspension, a colloid, a dispersion, a pellet, an implant, a pump, a particulate, a hydrogel, and an Immune Stimulating Complex (ISCOM).

In another aspect, the invention includes a method of generating regulatory T cells by providing a population of T cells in vitro and mixing the population of T cells with an α-MSH analog (or a cell expressing an α-MSH analog, or a nucleic acid encoding an α-MSH analog) and a therapeutic compound, e.g., an autoantigen. Any therapeutic compound as described herein can be used in this method. According to this method, the mixing of the population of T cells with an α-MSH analog and a therapeutic compound results in the generation of regulatory T cells in vitro. In one example, the α-MSH analog used in this method is capable of binding to a melanocortin receptor expressed on an antigen presenting cell. The α-MSH analog used in this method can be a selective analog. For example, the α-MSH analog may be unable to bind to or activate one or more melanocortin receptors, e.g., an MC3-R receptor and/or an MC4-R receptor. In one example, the α-MSH analog binds and activates a single melanocortin receptor.

The regulatory T cells generated according to this method can be introduced into an individual following their generation in vitro. The source of the cell population used to generate the regulatory T cells in vitro can either be from the same individual receiving the treatment (autologous), a different individual of the same species (allogeneic), or from an animal of a different species (xenogeneic). In one example of this method, the individual suffers from an autoimmune or inflammatory condition, and the administration results in the improvement of one or more symptoms of the condition.

Also included in the invention is a method of generating regulatory T cells by administering to an individual an α-MSH analog and a therapeutic compound. According to this method, the administration results in the generation of regulatory T cells in the individual. The α-MSH analog used in this method can be capable of binding to a melanocortin receptor expressed on an antigen presenting cell. The α-MSH analog used in this method can be a selective analog. For example, the α-MSH analog may be unable to bind to one or more melanocortin receptors, e.g., an MC3-R receptor and/or an MC4-R receptor. In one example, the α-MSH analog binds and activates a single melanocortin receptor.

In one example, the individual suffers from an autoimmune or inflammatory condition or is the recipient of an organ transplant, and the administration results in the improvement or alleviation of one or more symptoms of the condition.

Also included in the invention is a nucleic acid including a sequence encoding a polypeptide including an α-MSH analog concatamer. The polypeptide can include two or more α-MSH analogs or an α-MSH analog and an α-MSH.

Also included in the invention is a nucleic acid including a sequence encoding a polypeptide including an α-MSH analog and a membrane sequence. The invention also includes a nucleic acid including a sequence encoding a polypeptide including an α-MSH analog and a trafficking sequence such as a signal sequence. In one embodiment, the signal sequence contains the pro-opiomelanocortin (POMC) signal sequence or a portion thereof that directs the secretion of the polypeptide when expressed in a mammalian cell. Also included in the invention is a nucleic acid including a sequence encoding a polypeptide including an α-MSH analog and a GPI attachment signal peptide.

In another aspect, the invention includes a method of treatment including delivering a therapeutic compound (or a nucleic acid encoding a therapeutic compound) and an α-MSH-containing polypeptide (or a nucleic acid encoding an α-MSH-containing polypeptide) to an individual suffering from, or at risk of contracting, a disorder of the immune system. The disorder can be an autoimmune disorder, e.g., multiple sclerosis. The therapeutic compound can be contained in a composition that is administered to an individual to treat the disorder of the immune system. For example, the therapeutic compound can be contained within an interferon beta-containing composition. In this example, administration of the interferon beta-containing composition can cause an adverse local reaction in the treated individual. The method can include an additional step of identifying an individual as having, or being at risk of having, a disorder of the immune system, e.g., an autoimmune disorder such as multiple sclerosis. The α-MSH-containing polypeptide (or nucleic acid encoding an α-MSH-containing polypeptide) can optionally include an α-MSH analog in place of or in addition to the α-MSH amino acid sequence.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 2A depicts the nucleotide (SEQ ID NO:43) and amino acid (SEQ ID NO:42) sequences of the miniPOMC construct. The α-MSH sequence is underlined in this figure.

FIG. 2B depicts the nucleotide (SEQ ID NO:46) and amino acid (SEQ ID NO:47) sequences for an ACTH(1-14) construct. The ACTH(1-14) sequence is underlined in this figure.

FIG. 2C depicts the nucleotide (SEQ ID NO:48) and amino acid (SEQ ID NO:49) sequences for an ACTH (1-16) construct. The ACTH(1-16) sequence is underlined in this figure.

FIG. 2D depicts the nucleotide (SEQ ID NO:50) and amino acid (SEQ ID NO:51) sequences for an ACTH(1-17) construct. The ACTH(1-17) sequence is underlined in this figure.

FIG. 2E depicts the nucleotide (SEQ ID NO:79) and amino acid (SEQ ID NO:78) sequences for an αMSH-f construct. The αMSH-f sequence is underlined in this figure.

FIG. 9 depicts melanin synthesis (pg/ml) by untransfected B16/F10 cells treated with supernatant produced by B16/F10 cells transfected with: (1) pCMV-ssMSH; (2) pZYC-ssMSH; or (3) pIRES-2X-ssMSH.

FIG. 10 depicts melanin synthesis (pg/ml) by untransfected B16/F10 cells treated with supernatant produced by B16/F10 cells transfected with: (1) SH195 human serum albumin control vector; (2) SM195 mouse serum albumin control vector; (3) HLFα vector; or (4) MLF α vector.

DETAILED DESCRIPTION

Figure 1A:
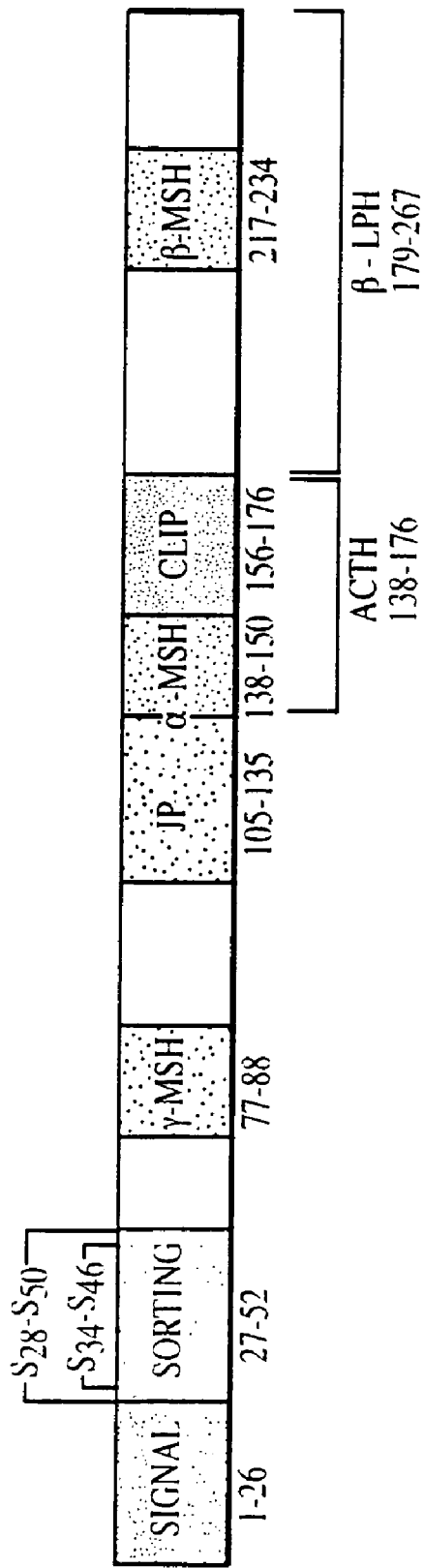
FIG. 1A depicts the structure of the POMC polypeptide, with the various regions indicated below the polypeptide by reference to their amino acid positions.

The invention encompasses compositions and methods for the in vivo and in vitro delivery of polypeptides containing α-MSH, α-MSH analogs, and nucleic acids encoding α-MSH and/or α-MSH analogs.

Polypeptides

Polypeptides of the invention include an α-MSH peptide fused to additional amino acid sequences. As used herein, "α-MSH" refers to a peptide of which the amino acid sequence is SYSMEHFRWGKPV (SEQ ID NO:1) or a fragment thereof that binds to a melanocortin receptor, e.g., MC1-R, with a binding affinity of at least 50% of that possessed by the SYSMEHFRWGKPV (SEQ ID NO:1) peptide. Preferably, the α-MSH peptide includes the amino acid sequence KPV (SEQ ID NO:2) or EHFRW (SEQ ID NO:41). Polypeptides of the invention can, for example, include any of the following sequences: SYSMEHFR-WGKPV (SEQ ID NO:1); SYSMEHFRWGKPVG (SEQ ID NO:62); SYSMEHFRWGKPVGKK (SEQ ID NO:63); SYSMEHFRWGKPVGKKR (SEQ ID NO:64); or SYSME-HFRWGKPVRSKR (SEQ ID NO:69). An α-MSH containing peptide can be N-terminal acetylated and/or C-terminal amidated.

In one embodiment, the polypeptide induces the generation of regulatory T cells, either in vitro or in vivo. In another embodiment, the polypeptide causes weight reduction in a subject having an obese phenotype, e.g., POMC or leptin deficient mice. In another embodiment, the polypeptide possesses at least 50% of an anti-inflammatory activity of the SYSMEHFRWGKPV (SEQ ID NO:1) peptide, as reviewed in Lipton and Catania (1997) Immunol. Today 18:140–145, herein incorporated by reference. Examples of anti-inflammatory activities of the SYSMEHFRWGKPV (SEQ ID NO:1) peptide include: (1) inhibition of hepatic nitric oxide and leukocyte infiltration in mice pretreated with *Corynebacterium parvum* followed by an acute injection of lipopolysaccharide (LPS); (2) inhibition of the development of chronic inflammation in mycobacterium-induced rats; (3) improvements of aspects of systemic inflammatory-response syndrome; (4) decreased histamine release by mast cells; (5) decreased neutrophil migration; and (6) decreased macrophage and dendritic cell activation, as measured by cytokine release or expression of a cell surface marker. In another embodiment, the polypeptide has one or more of the following activities: (1) the ability to reduce the activity of NF-kB (methods of evaluating NF-kB activation are described in Example 5); (2) the ability to increase melanin production by melanocytes (methods of evaluating melanin synthesis are described in Example 3); or (3) the ability to increase cAMP levels in a cell expressing a melanocortin receptor.

α-MSH fusion polypeptides can be produced by recombinant DNA techniques, chemical coupling, or chemical synthesis. As used herein, "fusion polypeptide" refers to a polypeptide that does not correspond to the amino acid sequence of a naturally occurring protein or fragment thereof. Fusion polypeptides including an α-MSH fused to additional peptide sequences can take many forms, as described below.

A polypeptide can include an α-MSH concatamer. An "α-MSH concatamer" is a polypeptide containing two or more α-MSH peptides. The α-MSH units of the concatamer may optionally include additional amino acid sequences between the units and/or flanking the units. This arrangement of α-MSH peptides can include any number of α-MSH units, e.g., at least 2, 3, 4, 5, 10, 20, 30, 40, 50, 100, 200, or more α-MSH units.

The α-MSH units of an α-MSH concatamer can be separated by a linker sequence. The linker sequence need not be of any defined length. A linker sequence separating α-MSH units can include an amino acid sequence that functions as a protease cleavage site (an amino acid sequence that can be specifically recognized and cleaved by a protease). For example, an α-MSH concatamer containing five α-MSH units, each unit linked to another by a linker sequence comprising a protease cleavage site, can be cleaved by a protease to release five individual α-MSH units, with or without leftover linker residues at one end or the other. Additionally, some of the linkers may not comprise a protease cleavage site, resulting in one or more intact α-MSH concatamers following protease cleavage. The linker sequence between two α-MSH units can optionally contain two or more protease cleavage sites. For example, the linker can include a protease cleavage site that cleaves immediately adjacent to the carboxy end of a first α-MSH unit, followed by a stretch of amino acids, followed by another protease cleavage that cleaves immediately adjacent to the amino end of a second α-MSH unit. This results in the release of α-MSH units having few if any linker amino acids remaining attached to the α-MSH sequence.

The protease cleavage site can be a site recognized, for example, by a cell-associated protease or a serum protease. Cell associated proteases include membrane proteins, membrane-associated proteins, and cytosolic proteins. An example of a protease cleavage site recognized by a cell-associated protease is the amino acid sequence recognized by furin, a cell-associated protease found in the trans golgi.

As an alternative (or in addition) to facilitating protease-induced cleavage, the linker sequence can provide spacing and/or orientation to the respective α-MSH units that promote the biological functioning of the individual α-MSH units in the context of an intact α-MSH concatamer. In this context, the linker sequence should separate the α-MSH units by a distance sufficient to ensure that each α-MSH unit properly folds into its secondary structure. Preferred linker sequences of this variety (1) should adopt a flexible extended conformation, (2) should not exhibit a propensity for developing an ordered secondary structure that could interact with the functional α-MSH units, and (3) should have minimal hydrophobic or charged character, which could promote undesired interaction with the functional α-MSH units. Typical surface amino acids in flexible protein regions include Gly, Asn and/or Ser. Permutations of amino acid sequences containing Gly, Asn and Ser would be expected to satisfy the above criteria for a linker sequence. Other near-neutral amino acids, such as Thr and Ala, can also be used in the linker sequence.

A linker sequence length of 20 amino acids can be used to provide a suitable separation of functional protein domains, although longer or shorter linker sequences may also be used. The length of the linker sequence separating the α-MSH units is generally greater than 3, and preferably greater than 4 amino acids: for example, from 5 to 500 amino acids, or more preferably from 5 to 100 amino acids Preferably, the linker sequence is from about 5–30 amino acids. In preferred embodiments, the linker sequence is about 5 to about 20 amino acids, or about 10 to about 20 amino acids. Amino acid sequences useful as linkers of the α-MSH units include, but are not limited to, $(SerGly_4$; SEQ ID NO:65$)_y$ wherein y is at least 2, or $Gly_4SerGly_5Ser$ (SEQ ID NO:66). A preferred linker sequence has the formula (SerGly$_4$)$_4$ (SEQ ID NO:67). Another preferred linker has the sequence ((Ser$_4$Gly)$_3$SerPro) (SEQ ID NO:68).

Alternatively, the α-MSH units can be directly fused without a linker.

A polypeptide including an α-MSH concatamer can further include a trafficking sequence. A "trafficking sequence" is an amino acid sequence that causes a polypeptide to which it is fused to be transported to a specific compartment of the cell and/or to be secreted by the cell. As defined herein, the term "trafficking sequence" is used interchangeably with "targeting sequence". The trafficking sequence can be included in the fusion polypeptide in the presence or absence of a linker sequence between α-MSH units and/or between the trafficking sequence and an α-MSH unit.

A signal sequence, a particular type of trafficking sequence, can fused to the α-MSH concatamer. A "signal sequence" is a peptide sequence that interacts with a signal recognition particle and directs a ribosome to the endoplasmic reticulum (ER) during translation. A signal sequence results in the protein of which it a component either being secreted or targeted to a membrane. The signal sequence is cleaved from the polypeptide in the ER, resulting in the mature form of the protein, e.g., a secreted protein. An example of a useful signal sequence that can be fused to the α-MSH concatamer is the signal sequence of the POMC polypeptide (MPRSCCSRSGALLLALLLQASMEVRG; SEQ ID NO:3) or a portion thereof that directs the secretion of the polypeptide when expressed in a mammalian cell. Preferably, the portion of the POMC signal sequence includes a fragment of the POMC signal sequence at least five amino acids in length. Other useful signal sequences include the signal peptide of HLA-DRα (MAISGVPVLG-FFIIAVLMSAQESWA; SEQ ID NO:4) and the signal peptides of the Adenovirus E3 and E1a proteins.

The trafficking sequence, e.g., a signal sequence, can include the sequence of a secreted peptide, e.g., serum albumin, e.g., human or murine serum albumin, or a portion thereof that directs secretion of the polypeptide.

Other examples of trafficking sequences that can be fused to the α-MSH concatamer include an amino acid sequence that guides a polypeptide to an endosome (e.g., the trafficking sequence of the invariant chain), a secretory granule (e.g., the POMC sorting sequence (WCLESSQCQDLT-TESNLLECIRACKP; SEQ ID NO:5)), and a lysosome (e.g., KFERQ (SEQ ID NO:6), QREFK (SEQ ID NO:7), and other pentapeptides having Q flanked on one side by four residues selected from K, R, D, E, F, I, V, and L).

A polypeptide containing an α-MSH concatamer can further include a membrane sequence. A "membrane sequence" of the fusion polypeptide can be any sequence that can be anchored in a membrane, thereby maintaining the membrane attachment of the polypeptide of which the membrane sequence is a component. A membrane sequence includes a sequence of at least about 15 amino acid residues, e.g., about 20, 25, 30, 35, 40, or 45 residues, which are inserted in the membrane. The membrane sequence can optionally span the membrane. Membrane sequences are rich in hydrophobic residues, and typically have an alpha-helical structure. In a preferred embodiment, at least 50%, e.g., at least 60%, 70%, 80%, 90%, 95% or even all of the amino acids of a membrane domain are hydrophobic, e.g., leucines, isoleucines, tyrosines, or tryptophans. Membrane domains are described in, for example, Zagotta et al. (1996) Annual Rev. Neurosci. 19: 235–263. The membrane sequence can correspond to all or a portion of the membrane domain of a naturally occurring protein, e.g., a human protein, e.g., the membrane domain of the transferrin receptor. A "portion of a membrane domain" means a sequence of consecutive amino acids contained in the membrane domain of a naturally occurring protein, wherein the portion retains the ability to maintain the polypeptide of which it is a component anchored in or associated with the cell membrane. Alternatively, the membrane sequence can be a variant of a naturally occurring membrane domain (i.e., with one or more substituted residues) or portion thereof, or can be a completely artificial amino acid sequence.

Polypeptides including an α-MSH concatamer can optionally contain a stretch of hydrophobic amino acids at its amino terminus that functions as an uncleaved signal for translocation into the endoplasmic reticulum and anchoring of the protein in the membrane, e.g., the hydrophobic transmembrane domains of type II transmembrane proteins such as the invariant chain (Ii), Ly-49, CD23, CD69, hepatic lectins, influenza virus neuraminidase, and intestinal isomaltase.

When inserted into the plasma membrane, the α-MSH concatamer can be oriented either extracellularly or intracellularly. Alternatively, the polypeptide can include one or more α-MSH units on either side of the membrane domain, so that the resultant polypeptide can have extracellular and intracellular α-MSH units.

The polypeptide can include a linker sequence between the membrane sequence and an α-MSH unit, a linker sequence between α-MSH units, or both. A linker sequence can include an amino acid sequence that functions as a protease cleavage site, as described herein. Alternatively, the linker sequence can be designed to orient the α-MSH units in a manner that promotes their biological activity.

Polypeptides including an α-MSH concatamer linked to a membrane sequence can further include a cytoplasmic domain. A "cytoplasmic domain" refers to a portion of a polypeptide described herein that is located in the cytoplasm when the polypeptide is inserted in a membrane, e.g., a plasma membrane. The cytoplasmic domain can be of any length and can be derived from a naturally occurring protein or can be an artificial sequence. A cytoplasmic domain can control the regulation or sorting of the polypeptide. For example, the cytoplasmic domain of the invariant chain (Ii) contains sequences that cause sorting of Ii to an endosome. Other cytoplasmic domains can participate in cell signaling processes.

A polypeptide containing an α-MSH concatamer can further include a glycosylphosphatidylinositol (GPI) attachment signal peptide. A "GPI attachment signal peptide" refers to an amino acid sequence that directs replacement of itself by a preassembled GPI in the ER. The GPI attachment signal peptide at the carboxy terminus of a GPI-linked protein is replaced by a preassembled GPI in the ER by a transamidation reaction, through the formation of a carbonyl intermediate. Many eukaryotic cell surface proteins are anchored to the cell membrane via a GPI linkage. The GPI attachment signal peptides of Thy-1 (see GenBank™ Accession Number P04216) and CD24 (see GenBank™ Accession Number A48996) are examples of GPI attachment signal peptides that may optionally be linked to the α-MSH concatamer described herein.

Anchoring a polypeptide to the membrane via linkage to GPI permits cleavage of the polypeptide from the membrane by phosphatidylinositol-specific phospholipases. For example, when a cell containing, attached to its plasma membrane, an α-MSH concatamer fused to a GPI moiety is treated with phosphatidylinositol-specific phospholipase C (PI-PLC), cleavage and release of the α-MSH concatamer will occur. The polypeptide can also contain a linker sequence between α-MSH units of the concatamer and/or between the GPI moiety and the α-MSH concatamer. A linker sequence can include an amino acid sequence that functions as a protease cleavage site, as described herein. For example, a polypeptide can include five α-MSH units linked to each other by a linker comprising a protease cleavage site, wherein the carboxy terminal α-MSH unit is fused to a GPI attachment signal peptide.

In another aspect of the invention, a polypeptide can include α-MSH fused to a membrane sequence. This polypeptide can include a single α-MSH, rather than the multiple units contained in the α-MSH concatamer described above. This polypeptide can for example have a length of less than 45 amino acids (e.g., less than 40, 35, 30, 25, or 20). This α-MSH-membrane sequence fusion can have any of the properties described above for the fusion of an α-MSH concatamer and a membrane sequence. For example, the α-MSH membrane sequence fusion polypeptide can further include a signal sequence or other trafficking sequence. Additionally, the fusion polypeptide can include a linker sequence, e.g., located between the membrane sequence and α-MSH. This linker sequence can include an amino acid sequence that can function as a protease cleavage site.

In another aspect of the invention, a polypeptide can also include α-MSH and a trafficking sequence. This polypeptide can include a single α-MSH, rather than the multiple units contained in the α-MSH concatamer described above. This trafficking sequence can have any of the properties described above for the fusion of an α-MSH concatamer and a trafficking sequence. In one example, the trafficking sequence is not the POMC signal sequence. If the trafficking sequence is the POMC signal sequence, then the fusion polypeptide preferably does not include the entire POMC sequence, and most preferably contains (a) the POMC signal sequence, (b) the POMC sorting sequence, (c) an α-MSH containing peptide, and (d) optionally a partial junction peptide of POMC containing protease digestion sites. Examples of such a fusion polypeptide include:

MPRSCCSRSGALLLALLLQASMEVRGWCLESSQCQD (SEQ ID NO:42)
LTTESNLLECIRACKPREGKRSYSMEHFRWGKPV;

MPRSCCSRSGALLLALLLQASMEVRGWCLESSQCQD (SEQ ID NO:47)
LTTESNLLECIRACKPREGKRSYSMEHFRWGKPVG;

MPRSCCSRSGALLLALLLQASMEVRGWCLESSQCQD (SEQ ID NO:49)
LTTESNLLECIRACKPREGKRSYSMEHFRWGKPVGK;

MPRSCCSRSGALLLALLLQASMEVRGWCLESSQCQD (SEQ ID NO:51)
LTTESNLLECIRACKPREGKRSYSMEHFRWGKPVGKKR; and MPRSCCSRSGALLLALLLQASMEVRGWCLESSQCQD (SEQ ID NO:78)
LTTESNLLECIRACKPREGKRSYSMEHFRWGKPVRSKR.

The trafficking sequence, e.g., a signal sequence, can correspond to the sequence of a secreted peptide, e.g., serum albumin, e.g., human or murine serum albumin, or a portion thereof that directs secretion of the polypeptide. The fusion polypeptide can have a length of less than 100 amino acids, such as less than 90, 80, 70, 60, 50, 40, 30, or 20 amino acids. The fusion polypeptide can include a linker sequence, e.g., located between the trafficking sequence and α-MSH. In one example, a fusion polypeptide contains an albumin sequence or a portion thereof that promotes secretion of the polypeptide, a linker sequence, e.g., GGVGG (SEQ ID NO:44) or GGYGG (SEQ ID NO:57), and an α-MSH containing peptide, e.g., SYSMEHFRWGKPV (SEQ ID NO:1), SYSMEHFRWGKPVG (SEQ ID NO:62), SYSMEHFRWGKPVGKK (SEQ ID NO:63), SYSMEHFRWGKPVGKKR (SEQ ID NO:64), or SYSMEHFRWGKPVRSKR (SEQ ID NO:69). A linker sequence can optionally include an amino acid sequence that can function as a protease cleavage site. In one example, the fusion polypeptide contains: (a) mouse serum albumin signal peptide; (b) mouse serum albumin signal propeptide; (c) mouse serum albumin; (d) an α-MSH containing peptide; and (e) optionally an amino acid sequence that functions as linker and protease cleavage sites between (c) and (d) The protease cleavage site can be a furin cleavage site. In addition, human serum albumin signal peptide, human serum albumin signal propeptide, and human serum albumin can be used.

In a polypeptide that includes a trafficking sequence, e.g., a signal sequence, and α-MSH, the α-MSH need not be directly linked to the trafficking sequence. As described above, the trafficking sequence and the α-MSH can be separated by a linker. Additionally, the α-MSH can be inserted, e.g., by recombinant DNA technology, within all or a portion of the amino acid sequence of a secreted protein, e.g., a secreted protein having a signal sequence. Preferably, the α-MSH is positioned in the fusion polypeptide in what corresponds to an exposed portion of the secreted protein, such as a solvent accessible loop of the secreted protein, e.g., the α-MSH is not inserted in a portion of the amino acid sequence of the secreted protein that is buried such as an α helix or a β pleated sheet. The fusion polypeptide can optionally include protease cleavage sites that flank the α-MSH peptide to promote cleavage of α-MSH from the fusion polypeptide.

Many fusion polypeptides can be made between a serum albumin or a fragment thereof and an α-MSH peptide. For example, α-MSH can be fused to the carboxy terminus of murine or human serum albumin. A linker can be included between the serum albumin sequence and the α-MSH sequence. The linker can include a protease recognition site such as a furin cleavage site. In another example, α-MSH can be inserted in a solvent accessible loop of albumin, e.g., human or murine serum albumin. The three-dimensional structure of serum albumin demonstrates that the protein contains at least four solvent accessible loops. α-MSH sequences could be placed in one, two, three, or four of these loops. The resulting fusion polypeptide can be used as a source of biologically active α-MSH. The fusion polypeptide can optionally include protease cleavage sites that flank the α-MSH sequences. In this way, a single fusion protein can be used to enhance the number of α-MSH molecules that can be produced.

In another aspect of the invention, a polypeptide can also include α-MSH fused to a GPI attachment signal peptide. This polypeptide can include a single α-MSH, rather than the multiple units contained in the α-MSH concatamer described above. The GPI attachment signal peptide can have any of the properties describe above for the fusion of an α-MSH concatamer and a GPI attachment signal peptide. The polypeptide can include a linker sequence, e.g., a sequence comprising a protease cleavage site, between α-MSH and the GPI attachment signal peptide. Alternatively, the polypeptide can include a linker without a protease cleavage site or no linker at all between α-MSH and the GPI attachment signal peptide. In this embodiment, α-MSH can be cleaved from the cell membrane by the action of, e.g., PI-PLC.

The α-MSH containing compositions described herein can include a therapeutic compound. A "therapeutic compound" is a compound that is causally associated with the occurrence of an immunologic reaction, e.g., inflammation or autoimmunity, and/or a neural condition in a mammal. A therapeutic compound can be a "therapeutic polypeptide," defined herein as a polypeptide or fragment thereof that is causally associated with occurrence of an immunologic reaction, e.g., inflammation or autoimmunity, and/or a neural condition in a mammal. Additionally, the therapeutic compound can be a non-peptide compound, e.g., single or double stranded DNA (dsDNA), a lipid, single or double stranded RNA (dsRNA), a carbohydrate, or a small molecule.

A composition containing a therapeutic compound (or a nucleic acid encoding a therapeutic compound) includes either an α-MSH-containing polypeptide or a nucleic acid encoding an α-MSH-containing polypeptide. A therapeutic compound can either be physically associated with an α-MSH-containing polypeptide, e.g., fused or conjugated as described herein, or a therapeutic compound and an α-MSH-containing polypeptide can be contained within the same container, though not physically associated.

A compound can be designated a "therapeutic compound" on the basis of its causing an adverse immunologic reaction when administered to an individual. For example, interferon beta (e.g., interferon beta-1a or interferon beta-1b)-containing compositions can cause adverse local reactions, e.g., skin reactions, when administered to an individual having multiple sclerosis. Therefore, an interferon beta-containing composition contains a therapeutic compound, as the term is used herein. A composition of the invention can thus include: (1) an α-MSH-containing polypeptide or a nucleic acid encoding an α-MSH-containing polypeptide; and (2) an interferon beta-containing composition.

A therapeutic polypeptide can include a peptide epitope that can be presented by a MHC class I or class II molecule of the mammal that exhibits the inflammation and/or autoimmunity. The therapeutic polypeptide can be self or nonself. For example, the therapeutic polypeptide can be an "autoantigen," defined herein a self polypeptide or antigenic fragment thereof that is causally associated with occurrence of an autoimmune disease in a mammal that produces the self polypeptide. An autoantigen can include a peptide epitope that can be presented by a MHC class I or class II molecule of the mammal that exhibits the autoimmunity.

A therapeutic compound can be fused to any of the α-MSH polypeptides of the invention. The therapeutic compound can be fused to an α-MSH polypeptide either by recombinant DNA techniques, chemical coupling, or chemical synthesis. For example, a polypeptide can include a signal sequence, α-MSH or an α-MSH concatamer, and a therapeutic compound. Optionally, a linker, e.g., a linker including a protease cleavage site, can separate the therapeutic compound and α-MSH. The therapeutic compound-α-MSH fusion can include any of the other polypeptide features described herein: a membrane sequence, a signal sequence, a linker, and/or a GPI attachment signal peptide.

Examples of therapeutic compounds that can be used are listed in Table 1. When α-MSH is produced within an animal by expression of a nucleic acid described herein, the polypeptide can trigger IL-10 production and thereby activate regulatory T cells. The production of both α-MSH and a therapeutic polypeptide in the cell of a mammal, e.g., an antigen presenting cell (APC), are expected to generate regulatory T cells specific for the expressed therapeutic polypeptide (see, e.g., Nishida and Taylor (1999) Invest. Opthamol. Vis. Sci. 40:2268–74). These regulatory T cells would then home to the site of antigen expression in the periphery (e.g., the pancreas for diabetes or the joint for arthritis) and modulate the activity of the disease-inducing T cell population, to prevent or improve the disease symptoms.

A therapeutic polypeptide can include an MHC-binding peptide. The MHC-binding peptide can affect T cell function by tolerizing or anergizing a T cell. Alternatively, the MHC-binding peptide could be designed to modulate T cell function by altering cytokine secretion profiles following recognition of the MHC/peptide complex. Peptides recognized by T cells can induce secretion of cytokines that (a) cause B cells to produce antibodies of a particular class, (b) induce inflammation, and (c) further promote host T cell responses.

Examples of therapeutic polypeptides include fragments of myelin basic protein (MBP), proteolipid protein (PLP), GAD65, islet cell antigen, collagen, desmoglein, α-crystallin, or β-crystallin, wherein the fragment can bind an MHC class I or II molecule. Table 1 lists many therapeutic compounds that are thought to be involved in autoimmune disease, such as multiple sclerosis, diabetes, uveitis, rheumatoid arthritis, and myasthenia gravis. Fragments of protein antigens can be essentially identical to any of the peptides listed in Table 2, such as MBP residues 80–102 (SEQ ID NO:8) or PLP residues 170–191 (SEQ ID NO:9).

TABLE 1

Therapeutic Compounds

| Disease | Associated Antigen | References |
|---|---|---|
| Coeliac disease | α-Gliadin | a |
| Goodpasture's syndrome | Basement membrane collagen | a |
| Graves' disease | Thyroid Stimulating Hormone (TSH) receptor | a |
| Hashimoto's disease | Thyroglobulin | a |
| Isaac's syndrome | Voltage-gated potassium channels | b |
| Insulin-dependent diabetes | Glutamic acid decarboxylase (GAD) | a |
| | Insulin receptor | a |
| | Insulin associated antigen (IA-w) | a |
| | Heat shock protein (Hsp) | b |
| Lambert-Eaton myasthenic syndrome (LEMS) | Synaptogamin in voltage-gated calcium channels | b |
| Multiple sclerosis | Myelin basic protein (MBP) | a |
| | Proteolipid protein (PLP) | a |

TABLE 1-continued

Therapeutic Compounds

| Disease | Associated Antigen | References |
|---|---|---|
| | Myelin oligodendrocyte-associated protein (MOG) | a |
| | αB-crystallin | a |
| Myasthenia Gravis | Acetyl choline receptor (AchR) | a |
| Paraneoplastic encephalitis | RNA-binding protein HuD | b |
| Pemphigus vulgaris | "PeV antigen complex" | a |
| | Desmoglein (DG) | c |
| Primary Biliary cirrhosis | Dihydrolipoamide acetyltransferase | b |
| | Pyruvate dehydrogenase complex 2 (PDC-E2) | d |
| Progressive systemic sclerosis | DNA topoisomerase | a |
| | RNA polymerase | a |
| Rheumatoid arthritis | Immunoglobulin Fc | a |
| | Collagen | |
| Scleroderma | Topoisomerase I | b |
| Stiff-man syndrome | Glutamic acid decarboxylase (GAD) | a |
| Systemic lupus erythematosus | ds-DNA | a |
| Uveitis | Interphotoreceptor retinoid-binding protein | b |
| | S antigen (rod out segment) | b |

References:
a) HLA and Autoimmune Disease, R. Heard, pg. 123–151 in HLA & Disease, Academic Press, New York, 1994 (R. Lechler, ed.)
b) Steinman (1995) Cell 80: 7–10
c) Amagai et al. (1991) Cell 67: 869–877
d) Shimoda et al. (1995) J. Exp. Med. 181: 1835–1845

TABLE 2

Class II Associated Peptides

| Peptide | Source Protein | SEQ ID NO: |
|---|---|---|
| GRTQDENPVVHFFKNIVTPRTPP | MBP 80–102 | 8 |
| AVYVYIYFNTWTTCQFIAFPFK | PLP 170–191 | 9 |
| TTNVRLKQQWVDYNLKW | AChR α 32–67 | 10 |
| QIVTTNVRLKQQWVDYNLKW | AChR α 48–67 | 11 |
| QWVDYNL | AChR α 59–65 | 12 |
| GGVKKIHIPSEKIWRPDL | AChR α 73–90 | 13 |
| AIVKFTKVLLQY | AChR α 101–112 | 14 |
| WTPPAIFKSYCEIIVYTHFPF | AChR α 118–137 | 15 |
| MKLGTWTYDGSVV | AChR α 144–156 | 16 |
| MKLGIWTYDGSVV | AChR α 144–157 analog (I-148) | 17 |
| WTYDGSVVA | AChR α 149–157 | 18 |
| SCCPDTPYLDITYHFVM | AChR α 191–207 | 19 |
| DTPYLDITYHFVMQRLPL | AChR α 195–212 | 20 |
| FIVNVIIPCLLFSFLTGLVFY | AChR α 214–234 | 21 |
| LLVIVELIPSTSS | AChR α 257–269 | 22 |
| STHVMPNWVRKVFIDTIPN | AChR α 304–322 | 23 |
| NWVRKVFIDTIPNNIMFFS | AChR α 310–327 | 24 |
| IPNIMFFSTMKRPSREKQ | AChR α 320–337 | 25 |
| AAAEWKYVAMVMDHIL | AChR α 395–310 | 26 |
| IIGTLAVFAGRLIELNQQG | AChR α 419–437 | 27 |
| GQTIEWIFIDPEAFTENGEW | AChR γ 165–184 | 28 |
| MAHYNRVPALPFPGDPRPYL | AChR γ 476–495 | 29 |
| LNSKIAFKIVSQEPA | desmoglein 3 190–204 | 30 |
| TPMFLLSRNTGEVRT | desmoglein 3 206–220 | 31 |
| SQRHGSKYLATASTMDHARHG | MBP 7–27 | 32 |
| RDTGILDSIGRFFGGDRGAP | MBP 33–52 | 33 |
| QKSHGRTQDENPVVHFFKNI | MBP 74–93 | 34 |
| DENPVVHFFKNIVT | MBP 84–97 | 35 |
| ENPVVHFFKNIVTPR | MBP 85–99 | 36 |
| HFFKNIVTPRTPP | MBP 90–102 | 37 |
| KGFKGVDAQGTLSK | MBP 139–152 | 38 |
| VDAQGTLSKIFKLGGRDSRS | MBP 144–163 | 39 |

Nucleic Acids

The fusion polypeptides of the invention can be produced by recombinant DNA technology. Nucleic acids of the invention encode either a single α-MSH containing peptide (e.g., SYSMEHFRWGKPV (SEQ ID NO:1), SYSMEHFR-WGKPVG (SEQ ID NO:62), SYSMEHFRWGKPVGKK (SEQ ID NO:63), SYSMEHFRWGKPVGKKR (SEQ ID NO:64), or SYSMEHFRWGKPVRSKR (SEQ ID NO:69))

or an α-MSH containing peptide fused to additional amino acid sequences, such as an additional α-MSH containing peptide or peptides or any other sequences as described herein.

The nucleic acids may be cloned into an expression vector, i.e., a vector in which the coding sequence is operably linked to expression control sequences. The need for, and identity of, expression control sequences will vary according to the type of cell in which the DNA is to be expressed. Generally, expression control sequences include a transcriptional promoter, enhancer, suitable mRNA ribosomal binding sites, translation start site, and sequences that terminate transcription and translation, including polyadenylation and possibly translational control sequences. Suitable expression control sequences can be selected by one of ordinary skill in the art. The nucleic acids encoding the polypeptides described herein can encode a methionine residue at the amino terminus of the polypeptide. Standard methods can be used by the skilled person to construct expression vectors. See generally, Sambrook et al., 1989, *Molecular Cloning: A Laboratory Manual* (2nd Edition), Cold Spring Harbor Press, N.Y. Vectors useful in this invention include linear nucleic acid fragments or circular DNAs, plasmid vectors, viral vectors, fungal vectors, and bacterial vectors. A "plasmid" is an autonomous, self-replicating, extrachromosomal, circular DNA. Preferred viral vectors are those derived from retroviruses, adenovirus, adeno-associated virus, pox viruses, SV40 virus, alpha viruses or herpes viruses.

An example of an expression vector useful in the invention is one in which a transcription sequence comprises: (a) a promoter sequence, operably linked to; (b) a sequence encoding the first 52 amino acids (MPRSCCSRSGALLLA-LLLQASMEVRGWCLESSQCQDLTTESN-LLECIRACKP; SEQ ID NO:40) of the human POMC molecule, comprising a signal sequence encoded by amino acids 1–26 and sorting signal encoded by amino acids 27–52 of POMC; (c) a sequence encoding a joining peptide of POMC or portion of a joining peptide which encodes the natural protease cleavage site (KR) for α-MSH cleavage; (d) an α-MSH containing peptide; and (e) a stop codon. Examples of fusion polypeptides encoded by such a vector include:

```
MPRSCCSRSGALLLALLLQASMEVRGWCLESSQCQD (SEQ ID NO:42)
LTTESNLLECIRACKPREGKRSYSMEHFRWGKPV;

MPRSCCSRSGALLLALLLQASMEVRGWCLESSQCQD (SEQ ID NO:47)
LTTESNLLECIRACKPREGKRSYSMEHFRWGKPVG;

MRPSCCSRSGALLLALLLQASMEVRGWCLESSQCQD (SEQ ID NO:49)
LTTESNLLECIRACKPREGKRSYSMEHFRWGKPVGK
K;

MRPSCCSRSGALLLALLLQASMEVRGWCLESSQCQD (SEQ ID NO:51)
LTTESNLLECIRACKPREGKRSYSMEHFRWGKPVGK
KR; and MRPSCCSRSGALLLALLLWASMEVRGWCLESSQCQD (SEQ ID NO:78)
LTTESNLLECIRACKPREGKRSYSMEHFRWGKPVRS
KR.
```

Additionally, an α-MSH expression vector can contain IRES (internal ribosome entry sites) sequences located between nucleic acids encoding polypeptides described herein. For example, a vector can contain IRES sequences between repeats of the transcription sequence described in the paragraph above or between a sequence encoding an α-MSH containing peptide and a sequence encoding a therapeutic polypeptide. For a description of IRES sequences and their use, see e.g., U.S. Pat. No. 6,087,129.

A nucleic acid can encode two separate polypeptides. The first translational product of the nucleic acid can be any of the α-MSH containing polypeptides described herein. The second translational product of the nucleic acid can be, e.g., a therapeutic polypeptide, a polypeptide that promotes the processing of an α-MSH containing polypeptide, e.g., prohormone convertase 1 (PC1; Li et al. (1999) Mol. Cell. Endocrinol. 158:143), or a selection marker, e.g., a drug resistance gene or a fluorescent protein.

In one example, a nucleic acid vector has two promoters, e.g., one promoter that drives expression of a sequence encoding an α-MSH containing polypeptide, e.g., SEQ ID NO:42, and one promoter that drives expression of a second polypeptide, e.g., PC1. In another example, a nucleic acid contains IRES sequences located between two coding sequences, e.g., between nucleic acid sequences encoding the polypeptide of SEQ ID NO:42 and PC 1. The IRES sequences cause the ribosome to attach to the initiator codon of the downstream translational unit and translate a second protein from a single polycistronic mRNA.

In another example, a composition can include a first and a second nucleic acid, wherein the first nucleic acid encodes an α-MSH containing peptide and the second nucleic acid encodes a second polypeptide, e.g., a therapeutic polypeptide. These nucleic acids can be administered to an individual simultaneously or at different times and can be contained in the same or different delivery vehicles.

Nucleic acids can be used for the in vitro production of the polypeptides of the invention. For example, a cell or cell line can be transfected, transformed, or infected with a nucleic acid, e.g., an expression vector, described herein. After an incubation period that permits expression of a polypeptide encoded by the nucleic acid, the polypeptide can be purified from the cell culture media, if secreted, or from a lysate of the cells expressing the polypeptide.

Conjugates

The fusion polypeptides of the invention can be created by a chemical coupling of a polypeptide including α-MSH to another compound, e.g., a therapeutic compound, to form a conjugate. A "conjugate" is a non-naturally occurring substance comprising an α-MSH containing polypeptide that has been linked, covalently or noncovalently, to a heterologous compound via the action of a coupling agent. The link between two components may be direct, e.g., where an α-MSH containing peptide is linked directly to a heterologous compound, or indirect, e.g., where an α-MSH containing peptide is linked to an intermediate, e.g., a backbone, and that intermediate is also linked to the heterologous compound. A coupling agent should function under conditions of temperature, pH, salt, solvent system, and other reactants that substantially retain the chemical stability of the α-MSH containing peptide, the backbone (if present), and the heterologous compound.

A coupling agent can link components without the inclusion of the coupling agent in the resulting fusion polypeptide. Other coupling agents do result in the inclusion of the coupling agent in the resulting fusion polypeptide. For example, coupling agents can be cross-linking agents that are homo- or hetero-bifunctional, and wherein one or more atomic components of the agent are retained in the composition. A coupling agent that is not a cross-linking agent can be removed entirely following the coupling reaction, so that the molecular product is composed entirely of the α-MSHcontaining polypeptide, the heterologous compound, and a backbone moiety (if present).

Many coupling agents react with an amine and a carboxylate to form an amide, or with an alcohol and a carboxylate to form an ester. Coupling agents are known in the art, see, e.g., Greene and Wuts (1991) "Protective Groups in Organic Synthesis," 2nd Ed., John Wiley, N.Y. Coupling agents should link component moieties stably, but such that there is minimal or no denaturation or deactivation of the α-MSH containing polypeptide or the heterologous compound.

The conjugates of the invention can be prepared by coupling an α-MSH containing polypeptide to a heterologous compound using methods known in the art. A variety of coupling agents, including cross-linking agents, can be used for covalent conjugation. Examples of cross-linking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl) cyclohexane-1-carboxylate (sulfo-SMCC). See, e.g., Karpovsky et al. (1984) *J. Exp. Med.* 160:1686 and Liu et al. (1985) *Proc. Natl. Acad. Sci. USA* 82:8648. Other methods include those described by Paulus (1985) *Behring Ins. Mitt.* 78:118–132; Brennan et al. (1985) *Science* 229:81–83; and Glennie et al. (1987) *J. Immunol.* 139: 2367–2375. A large number of coupling agents for peptides and proteins, along with buffers, solvents, and methods of use, are described in the Pierce Chemical Co. catalog, pages T-155–T-200, 1994 (3747 N. Meridian Rd., Rockford Ill., 61105, U.S.A.; Pierce Europe B.V., P.O. Box 1512, 3260 BA Oud Beijerland, The Netherlands), which catalog is hereby incorporated by reference.

DCC is a useful coupling agent (Pierce #20320; Rockford, Ill.). It promotes coupling of the alcohol NHS in DMSO (Pierce #20684), forming an activated ester which can be cross-linked to polylysine. DCC (N,N'-dicyclohexylcarbodiimide) is a carboxy-reactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4 and a spacer arm length of 6.8 angstroms, is reactive to NHS-esters and pyridyldithio groups, and produces cleavable cross-linking such that upon further reaction, the agent is eliminated so the α-MSH containing polypeptide can be linked directly to a backbone or heterologous compound. Other useful conjugating agents are SATA (Pierce#26102) for introduction of blocked SH groups for two-step cross-linking, which are deblocked with hydroxylamine-HCl (Pierce #26103), and sulfo-SMCC (Pierce#22322), reactive towards amines and sulfhydryls. Other cross-linking and coupling agents are also available from Pierce Chemical Co. (Rockford, Ill.). Additional compounds and processes, particularly those involving a Schiff base as an intermediate, for conjugation of proteins to other proteins or to other compositions, for example to reporter groups or to chelators for metal ion labeling of a protein, are disclosed in EP 243,929 A2 (published Nov. 4, 1987).

α-MSH Analogs

Any biologically active analog of α-MSH can be used in place of α-MSH in the compositions and methods described herein. By "biologically active" is meant possessing the ability to bind to a melanocortin receptor. Preferably, a biologically active analog of α-MSH can bind to a melanocortin receptor with an affinity, e.g., a mM, µM, or nM affinity, sufficient to induce a biological response, e.g., melanin synthesis, in a cell expressing a melanocortin receptor. Preferably, a biologically analog of α-MSH possesses one or more of the biological activities described herein for an α-MSH peptide. For example, a biologically analog of α-MSH may bind to a melanocortin receptor, e.g., MC1-R, with a binding affinity of at least 50% of that possessed by the SYSMEHFRWGKPV (SEQ ID NO:1) peptide.

An α-MSH analog can be linked to an additional amino acid sequence or a therapeutic compound, as described herein with respect to an α-MSH peptide. An α-MSH analog consisting of naturally occurring amino acids can be encoded by a nucleic acid and can be optionally linked to other amino acid sequences in the form of a fusion protein.

An α-MSH analog can have either the same or a different receptor specificity as compared to a naturally occurring α-MSH, e.g., the SYSMEHFRWGKPV (SEQ ID NO:1) peptide. For example, an α-MSH analog may bind to or activate a single specific melanocortin receptor subtype, e.g. MC1-R, or to a subset of melanocortin receptor subtypes, e.g., MC1-R and MC5-R. An α-MSH analog can be used that does not bind to specific subtypes of melanocortin receptors, e.g., receptors expressed in brain tissue such as MC3-R and/or MC4-R.

The amino acid residues at particular positions may include analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject peptide can include an amino acid analog such as β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Analogs of α-MSH can be generated by mutagenesis, such as by discrete point mutation(s), or by truncation. For instance, mutation can give rise to analogs which retain substantially the same, or merely a subset, of the biological activity of the polypeptide from which it was derived.

The polypeptides that can be utilized in the present invention also include analogs of α-MSH that are resistant to proteolytic cleavage such as those that, due to mutations, alter ubiquitination or other enzymatic targeting associated with the protein.

Polypeptide analogs may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation in vivo), or post-translational modifications (e.g., to alter the phosphorylation pattern of the polypeptide). Such modified peptides, when designed to retain at least one activity of a naturally-occurring form of α-MSH, are considered functional equivalents of the polypeptides described herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally grouped separately as aliphatic-hydroxyl; (4) aromatic=phenylalanine, tyrosine, tryptophan; (5) amide=asparagine, glutamine; and (6) sulfur-containing=cysteine and methionine (see, e.g., Biochemistry, 2nd ed., Ed. by L. Stryer, W H Freeman and Co.: 1981). Whether a change in the amino acid sequence of a peptide results in a functional analog (e.g., functional in the sense that the resulting peptide mimics a function of a peptide containing the sequence of SYSMEHFRWGKPV (SEQ ID NO:1)) can be readily determined by assessing the ability of the variant peptide to produce a response in cells in a fashion similar to an α-MSH peptide. Polypeptides in which more than one replacement has taken place can readily be tested in the same manner.

As set forth above, alterations in primary sequence include genetic variations, both natural and induced. Also included are analogs that include residues other than naturally occurring L-amino acids, e.g., D-amino acids or non-naturally occurring or synthetic amino acids, e.g., β or δ amino acids. Alternatively, increased stability or solubility may be conferred by cyclizing the peptide molecule.

Nonsequence modifications include in vivo or in vitro chemical derivatization of polypeptides, e.g., acetylation, methylation, phosphorylation, carboxylation, or glycosylation. Glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes. Phosphorylation can be modified by exposing the polypeptide to phosphorylation-altering enzymes, e.g., kinases or phosphatases.

It will be appreciated by those of skill in the art that a peptide mimic may serve equally well as a peptide for the purpose of providing the specific backbone conformation required for binding to melanocortin receptors and eliciting appropriate biological responses, e.g., the generation of regulatory T cells. Accordingly, it is contemplated as being within the scope of the present invention to produce α-MSH analogs through the use of naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or sometimes as an "isosteric peptidomimetic" to designate substitutions or derivations of peptide-based α-MSH analogs that possess the same backbone conformational features and/or other functionalities.

The use of isosteric peptidomimetics for the development of high-affinity and/or selective peptide analogs is well known in the art. Of particular relevance to the present invention, mimics of peptide backbone structures, such as α-helicies, β-turns and β sheets, have been developed. For example, Kemp et al. (1988) Tetrahedron Lett. 29:5057 disclose derivatives of dilactams of L-α, δ-diaminobutyric acid and D-glutamic acid as a constrained β-turn template, particularly for the selective stabilization of type II β-turns. Kahn et al. (1988) J. Amer. Chem. Soc. 110:1638 disclose a non-peptide mimetic of β-turns produced by oxidative intramolecular cycloaddition of an azodicarbonyl system. As another example, Olson et al. (1990) J. Amer. Chem. Soc. 112:323 disclose a model tetrapeptide mimetic of a type II' β-turn produced from a 9-membered ring lactam system. Numerous other peptide mimetic structures useful for the practice of the present invention are available and will be apparent to those of skill in the art (see, e.g., Peptides: Chemistry, Structure and Biology (1990), J. E. Rivier & G. R. Marshall, eds., ESCOM Publishers, Leiden, Netherlands). Assuming rotational constraints similar to those of amino acid residues within a peptide, analogs comprising non-amino acid moieties may be analyzed, and their conformational motifs verified, by means of the Ramachandran plot.

Examples of α-MSH analogs that can be used in the compositions and methods of the present invention are described in U.S. Pat. No. 4,866,038, U.S. Pat. No. 5,830,994, U.S. Pat. No. 5,157,023, WO 96/41815, Brandenburger et al. (1999) J. Recept. Signal. Transduct. Res. 19:467, Giblin et al. (1998) Proc. Natl. Acad. Sci. USA 95:12814, and Hruby et al. (1995) J. Med. Chem. 38:3454. The content of each of these references is hereby incorporated by reference.

Delivery Systems

The invention encompasses systems and methods for the in vitro, in vivo, and ex vivo delivery of the nucleic acids, polypeptides, and analogs of the invention. A variety of methods of delivering the compositions described herein are well know to those of skill in the art.

The polypeptides, analogs, or nucleic acids, can be administered using standard methods, e.g., those described in Donnelly et al. (1994) J. Imm. Methods 176:145, and Vitiello et al. (1995) J. Clin. Invest. 95:341. Polypeptides, analogs, and nucleic acids of the invention can be injected into subjects in any manner known in the art, e.g., intramuscularly, intravenously, intraarterially, intradermally, intraperitoneally, intranasally, intravaginally, intrarectally or subcutaneously, or they can be introduced into the gastrointestinal tract, the mucosa, or the respiratory tract, e.g., by inhalation of a solution or powder containing the polypeptides or nucleic acids. Alternately, the polypeptides, analogs, or nucleic acids of the invention may be applied to the skin, or electroporated into the cells or tissue. Alternately, the polypeptides, analogs, or nucleic acids of the invention may be treated with ultrasound to cause entry into the cells or tissue. Long lasting continuous release of the polypeptides, analogs or nucleic acids of the invention can also be obtained, for example, through the use of osmotic pumps.

The polypeptides, analogs, and nucleic acids encoding polypeptides can be delivered in a pharmaceutically acceptable carrier such as saline. The nucleic acid can be naked or associated or complexed with a delivery vehicle. For a description of the use of naked DNA, see e.g., U.S. Pat. No. 5,693,622. Nucleic acids and polypeptides can be delivered using delivery vehicles known in the art, such as lipids, depot systems, hydrogel networks, particulates, liposomes, ISCOMS, microspheres or nanospheres, microcapsules, microparticles, gold particles, virus-like particles, nanoparticles, polymers, condensing agents, polysaccharides, polyamino acids, dendrimers, saponins, adsorption enhancing materials, colloidal suspensions, dispersions, powders, or fatty acids.

Viral particles can also be used, e.g., retroviruses, adenovirus, adeno-associated virus, pox viruses, SV40 virus, alpha virus or herpes viruses.

It is expected that a dosage of approximately 0.1 to 100 μmoles of the polypeptide, or of about 1 to 200 μg of DNA, would be administered per kg of body weight per dose. As is well known in the medical arts, dosage for any given patient depends upon many factors, including the patient's size, body surface area, age, the particular compound to be administered, sex, time and route of administration, general health, and other drugs being administered concurrently. Determination of optimal dosage is well within the abilities of a pharmacologist of ordinary skill.

Other standard delivery methods, e.g., biolistic transfer, or ex vivo treatment, can also be used. In ex vivo treatment, cells, e.g., APCs, dendritic cells, peripheral blood mononuclear cells, or bone marrow cells, can be obtained from a patient or an appropriate donor and treated ex vivo with a composition of the invention, and then returned to the patient.

Microparticles or nanoparticles, including those described in U.S. Pat. No. 5,783,567 and U.S. Ser. No. 60/208,830, filed Jun. 2, 2000, can be used as vehicles for delivering macromolecules such as DNA, RNA, or polypeptides into cells. The microparticles can contain macromolecules embedded in a polymeric matrix or enclosed in a shell of polymer. Microparticles act to maintain the integrity of the macromolecule, e.g., by maintaining the DNA in a nondegraded state. Microparticles can also be used for pulsed delivery of the macromolecule, and for delivery at a specific site or to a specific cell or target cell population.

The polymeric matrix can be a synthetic or natural biodegradable co-polymer such as poly-lactic-co-glycolic acid, starch, gelatin, or chitin. Microparticles that are less than 10 μM in diameter can be used in particular to maximize delivery of DNA molecules into a subject's phagocytotic cells. Alternatively, microparticles that are greater than 10 μM in diameter can be injected or implanted in a tissue, where they form a deposit. As the deposit breaks down, the nucleic acid or polypeptide is released gradually over time and taken up by neighboring cells.

The microparticles can be delivered directly into an individual's bloodstream (e.g., by intravenous or intraarterial injection or infusion) preferably if uptake by the phagocytic cells, e.g., phagocytic cells of the reticuloendothelial system (RES), is desired. Additionally, microparticles can be targeted, via subcutaneous injection, for uptake by the phagocytic cells of the draining lymph nodes. The microparticles can also be introduced intradermally, e.g., to the APCs of the skin, such as dendritic cells and Langerhans cells. Another useful route of delivery, particularly for DNAs encoding tolerance-inducing polypeptides, is via the gastrointestinal tract, e.g., orally. Additionally, microparticles can be introduced into the lung, e.g., by inhalation of powdered microparticles or of a nebulized or aerosolized solution containing the microparticles, where the particles can be taken up by alveolar macrophages. Once a phagocytic cell phagocytoses a microparticle, the nucleic acid is released into the interior of the cell. Upon release, the nucleic acid expresses the encoded polypeptide, using the cellular transcription and translation machinery.

The polypeptides, analogs, and nucleic acids of the invention can be administered into subjects via lipids, dendrimers, microspheres, colloids, suspensions, emulsions, depot systems, hydrogel networks, liposomes, or electroporation using techniques that are well known in the art. For example, liposomes carrying polypeptides or nucleic acids encoding polypeptides can be delivered as described in Reddy et al. (1992) J. Immunol. 148:1585; Collins et al. (1992) J. Immunol. 148:3336–3341; Fries et al. (1992) Proc. Natl. Acad. Sci. USA 89:358; and Nabel et al. (1992) Proc. Nat. Acad. Sci. USA 89:5157. Examples of hydrogel networks are described in U.S. Ser. No. 60/270,256, filed Feb. 20, 2001.

The peptides, analogs, and nucleic acids of the invention can be administered by using ISCOMS, which are negatively charged, cage-like structures of 30–40 nm in size formed spontaneously on mixing cholesterol and Quil A (saponin), or saponin alone. A peptide (or analog) and nucleic acid of the invention can be co-administered with an ISCOM, or the peptide (or analog) and nucleic acid can be administered separately. The peptides, analogs, and nucleic acids of the invention may also be electroporated into cells or tissues of a recipient. Electroporation may occur ex vivo or in vivo.

Methods of Use

The nucleic acid compositions of the invention can be used to produce recombinant α-MSH containing peptides in cells. For example, an expression vector encoding an α-MSH-containing polypeptide can be transfected into a cell, e.g., bacteria or mammalian cells such as yeast cells, and an α-MSH containing peptide can be purified from the culture medium. The compositions of the invention may be used to produce α-MSH containing peptides in cells that either normally express or do not express α-MSH. Expression may be controlled via a specific promoter or regulatory sequence in the nucleic acid or recombinant α-MSH protein. Expression of the recombinant α-MSH containing peptide may induce expression of the cellular α-MSH by the transfected cell or other cells.

As described in the Examples, the transfection of a cell with a nucleic acid encoding an α-MSH containing peptide induces melanin synthesis in the transfected cell and/or in another cell exposed to the supernatant of a transfected cell. Melanin synthesis is associated with increased cellular pigmentation, a phenomenon which can be readily detected by using assays such as those described in the Examples. Because the nucleic acids described herein produce a polypeptide that induces a readily detectable color change in a transfected cell (or in a cell exposed to the supernatant of a transfected cell), the nucleic acids can be used in a variety of reporter assays. In one example, a nucleic acid construct encoding an α-MSH containing peptide can be used to evaluate promoter activity. In such a method, a promoter sequence or a candidate promoter sequence is operatively linked to the nucleic acid construct, and the induction of melanin synthesis following transfection of a cell with the construct is evaluated. According to this method, a change in coloration following transfection is indicative of promoter activity. This method can optionally include evaluating the ability of a test compound to modulate (increase or decrease) expression regulated by the promoter or candidate promoter sequence. In a similar fashion, a nucleic acid construct encoding an α-MSH containing peptide can be used as a reporter to evaluate an expression vector for its ability to produce a gene product. In a second example, a nucleic acid construct encoding an α-MSH containing peptide can be used to evaluate the efficiency of gene transfer methods. In one method, a transfection protocol can be optimized by transfecting cells under a variety of conditions with a nucleic acid described herein, wherein the efficiency of the gene transfer under each of the conditions is determined by measuring melanin synthesis.

The compositions of the invention can also be used to effect a wide variety of immunomodulatory functions, e.g., anti-inflammatory functions, in vitro and in vivo. For example, the α-MSH compositions can be used to inhibit the activity of various cells and/or molecules of the immune system. In some cases, the α-MSH compositions can inhibit one or more of the following: histamine release from mast cells; neutrophil chemotaxis and/or migration to an inflamed site; macrophage activation; the expression of costimulatory factors, e.g., CD86 and/or CD40, by APCs; or the secretion of cytokines such as IL-12, IFN-λ and TNF-α. In some cases, the α-MSH compositions can promote secretion of TGFβ and/or IL-10.

The compositions of the invention, e.g., nucleic acids, polypeptide, conjugates, and analogs, can also be used to induce tolerance and/or to induce a regulatory T cell response, either in vitro or in vivo. For example, a regulatory T cell response can be induced by administration of an α-MSH-containing polypeptide or by co-administration of an α-MSH-containing polypeptide and a therapeutic polypeptide.

An α-MSH composition can also be used to alter the activity of macrophages, monocytes, dendritic cells, or other phagocytic cells. In addition, an α-MSH composition can be used to elicit anti-inflammatory activities in vitro or in vivo. Examples of anti-inflammatory activities include: (1) inhibition of hepatic nitric oxide and leukocyte infiltration in mice pretreated with *Corynebacterium parvum* followed by an acute injection of lipopolysaccharide; (2) inhibition of the development of chronic inflammation in mycobacterium-induced rats; (3) inhibition of the colonic and intestinal tract inflammation that ensues in mice following intra-rectal treatment with TNBS in ethanol; (4) improvements of aspects of systemic inflammatory-response syndrome; (5) decreased histamine release by mast cells; (6) decreased neutrophil migration; (7) decreased macrophage activation as demonstrated by reduction of IL-12, IFN-γ or TNFα production and/or a change in cell surface markers; (8) decreased dendritic cell activation measured by altered cytokine production or changes in cell surface expressed activation marker; (9) decrease in the number and/or size of plaques in the brain of mammals with Alzheimer's or a related disease; and (10) decreased production of immunoglobulin. The compositions of the invention, e.g., nucleic acids, polypeptide, conjugates, and analogs, can be used to stimulate cellular production of various molecules, e.g. IL-10, TGF-β, endogenous α-MSH, or melanin (for example by melanocytes). Alternatively, the compositions can be used to reduce cellular production of various molecules, e.g., IL-1, TNF-α, IFN-γ, IL-12, and/or endogenous α-MSH. Furthermore, because an α-MSH composition can reduce NF-κB activation by a cell, the compositions can be useful for treating conditions associated with NF-κB activation, such as inflammatory disorders, cell proliferation and cancer.

Nucleic acids, polypeptides, and/or analogs of the invention can be used to treat disorders such as inflammatory disorders, autoimmunity, or neurological disorders, e.g., neuro-inflammatory disorders. Examples of disorders that can be treated include rheumatoid arthritis, asthma, rhinitis, sepsis, interstitial cystitis, cystitis, Alzheimer's disease, symptoms associated with chronic dialysis, erectile dysfunction, obesity, experimental autoimmune encephalitis, cirrhosis, dermatitis, psoriasis, contact hypersensitivity, inflammatory bowel disease, spinal cord injury, diabetes, multiple sclerosis, lupus, uveitis, and coleiac disease. These disorders can be treated by delivering to an individual a nucleic acid, a polypeptide, an analog, or a combination thereof, e.g., a nucleic acid encoding α-MSH and a therapeutic polypeptide, or a nucleic acid encoding an α-MSH analog and a nucleic acid encoding a therapeutic polypeptide.

A nucleic acid encoding an α-MSH polypeptide of the invention can be used to treat an inflammatory disorder. The delivery of a nucleic acid to a target cell and the expression of α-MSH therein can result in an inhibition of the secretion of interferon (IFN)-gamma by T cells (e.g., autoreactive T cells) and decrease the effects of other mediators of inflammation as well. This inhibition of immune activity is expected to ameliorate the inflammatory condition.

Compositions described herein can be used to generate regulatory T cells, either in vitro or in vivo. For example, a population of T cells can be contacted in vitro with a therapeutic compound, e.g., an autoantigen, and an α-MSH polypeptide or an α-MSH analog. Regulatory T cells generated in vitro by this method can then be introduced into a subject. The regulatory T cells generated and administered in this method can be either autologous, allogeneic, or xenogeneic. The regulatory T cells can be used to ameliorate one or more symptoms of a condition such as autoimmunity or inflammation when introduced into the subject.

In addition to the in vitro stimulation methods, a therapeutic compound and an α-MSH polypeptide or an α-MSH analog can be delivered directly to an individual. The compositions can optionally be delivered via a delivery vehicle as described herein. This in vivo delivery method can be used to generate regulatory T cells, or to reduce the symptoms of autoimmunity or inflammation.

In one example, rheumatoid arthritis is treated by delivery of an α-MSH containing peptide to an arthritic joint, e.g., by injection of a nucleic acid such as a recombinant adenovirus encoding α-MSH. The recombinant adenovirus infects cells in the joint, resulting in expression and secretion of the α-MSH containing peptide by the infected cells. The local production of an α-MSH containing peptide is expected to result in a decreased production of inflammatory mediators and a decreased production of IL-1 and TNF-α by immune cells that are present in or migrate to the inflamed joint.

In another example, asthma is treated by, for example, aerosolizing liposomes (or powdered liposomes) containing plasmid DNA encoding an α-MSH containing peptide and delivering the aerosol to the lung by methods known in the art. Cells of the lung, e.g., epithelial cells, take up the liposomes, express the α-MSH containing peptide, and result in suppression of the inflammation associated with asthma, e.g., by decreasing neutrophilia and production of TNF-α and NO. In this example, long term (e.g., months) production of α-MSH is not required. The delivery of a plasmid encoding the peptide provides for localized, short term (e.g., days or weeks) activity of the peptide and thus would be more potent than a single dose delivery of the peptide alone.

In another example, cirrhosis is treated, for example, by injecting microspheres containing DNA encoding an α-MSH containing peptide into an individual by a route that favors delivery of the particles to the liver, e.g., intravenous or intra-hepatic artery injection. Localized production of the α-MSH containing peptide by cells, e.g., hepatocytes or Kupfer cells, is expected to reduce inflammation and result in an improvement of cirrhosis.

In another example, a skin disorder is treated, for example, by targeting a plasmid encoding an α-MSH containing peptide to the skin by complexation of the plasmid with gold particles and delivery through a gene gun. For a description of gene transfer using a gene gun, see, e.g., U.S. Pat. No. 5,865,796. Expression of an α-MSH containing peptide by keratinocytes and Langerhans cells is expected to result in improvement of conditions such as dermatitis, psoriasis, and/or contact hypersensitivity.

In another aspect, a nucleic acid encoding an α-MSH containing peptide and an autoantigen can be used to treat an inflammatory disorder or an autoimmune disease. In this method, DNA encoding an α-MSH containing peptide and the autoantigen are delivered to and expressed in a target organ or tissue. This delivery and expression may occur at a disease site (e.g., an arthritic joint, colon, brain) or in the periphery (e.g., muscle, GALT, skin, lymph node, or spleen). α-MSH prevents TNF-α and IL-1 production and causes APCs to produce IL-10 (and possibly others) (Luger et al. (1997) J Investig Dermatol Symp Proc 2:87). Because IL-10 production by APCs can induce regulatory T cells that decrease the severity of autoimmune disease (Constant et al. (1997) Ann Rev Immunol 15:297), the production of an α-MSH containing peptide and an autoantigen in the periphery should generate regulatory T cells specific for the expressed autoantigen. The induced regulatory T cells are expected to home to the site of antigen expression in the periphery (e.g., the pancreas for diabetes) and to modulate the activity of the disease-inducing T cell population so as to prevent or improve the disease symptoms.

In another aspect, an α-MSH-containing polypeptide (or a nucleic acid encoding an α-MSH-containing polypeptide) can be administered to an individual together with a therapeutic compound (or a nucleic acid encoding a therapeutic compound), as the term is used herein. The α-MSH-containing polypeptide and therapeutic compound can either be physically associated, e.g., fused or conjugated, or contained within the same vessel but not physically associated. Alternatively, the α-MSH-containing polypeptide and the therapeutic compound can be contained within separate containers.

An example of a therapeutic compound that can be administered according to this method is an interferon beta (e.g., interferon beta-1 such as interferon beta-1a or interferon beta-1b)-containing composition. Interferon beta-containing compositions can cause adverse skin reactions when administered to an individual having multiple sclerosis (see, e.g., Walther et al. (1999) Neurology 53:1622–27). Although interferon beta-containing compositions can be beneficial in reducing the symptoms of multiple sclerosis or slowing disease progression, the side effects of their administration can be undesirable. By co-administration of an α-MSH-composition together with an interferon beta-containing composition, the α-MSH-composition can reduce or eliminate one or more of the adverse immunologic reactions associated with interferon beta administration.

In one example, multiple sclerosis is treated, for example, by feeding to a mammal microspheres containing DNA encoding an α-MSH containing peptide and MBP. APCs phagocytose the microspheres and express the α-MSH containing peptide and MBP peptides. The MBP is processed and presented by the APC to activate T cells. The APC also produces α-MSH that causes the APC and/or surrounding APCs to secrete IL-10. In the presence of IL-10, the MBP-specific T cells become regulatory T cells, which then target disease sites. Once at the disease site (e.g., the brain or central nervous system) the regulatory T cells downregulate the activity of the disease-inducing T cells.

In another example, diabetes is treated using a liposome/plasmid complex to deliver DNA to the spleen or lymph nodes of an individual. In this example, the plasmid (or plasmids) encode an α-MSH containing peptide and insulin.

In another example, autoimmune encephalitis is treated or prevented by delivering nucleic acids or microparticles containing nucleic acids of the invention to a mammal. Plasmid DNA constructs that express an α-MSH containing peptide may reduce the occurrence and severity of the disease.

In another example, coeliac disease is treated, for example, by feeding to a mammal microspheres containing plasmid DNA encoding an α-MSH containing peptide and glutenin.

In another example, rheumatoid arthritis is treated, for example, by targeting a plasmid encoding an α-MSH containing peptide and collagen to the skin by complexation with gold particles and delivery through a gene gun.

In another example, an allergic condition is treated by targeting a plasmid encoding an α-MSH containing peptide and a therapeutic polypeptide to the site of an allergic reaction.

In another example, a composition of the invention is delivered to an individual to reduce fever in the individual.

In another example, a composition of the invention is delivered to an individual to induce melanin production in the individual.

In another example, the compositions of the invention are used to reduce obesity, reduce weight gain and/or cause weight reduction in a subject, e.g., a POMC or leptin deficient mammal. POMC deficient mice and humans have an obese phenotype (see, e.g., Krude et al. (1998) Nat. Genet. 19:155–157 and Yaswen et al. (1999) Nat. Med. 5:1066–1070, herein incorporated by reference). Treatment of POMC deficient mice with an α-MSH peptide analog has been found to lead to weight reduction. However, the treatment required daily injections into the peritoneal cavity of a large amount of peptide analog (Yaswen et al. supra). Providing a subject with a nucleic acid encoding an α-MSH containing peptide described herein would elicit a beneficial effect with fewer administrations and reduce the need for daily treatments of the subject, e.g., permitting weekly, monthly or yearly treatments.

The following are examples of the practice of the invention. They are not to be construed as limiting the scope of the invention in any way.

EXAMPLES

Example 1

Construction of Expression Vectors

Figure 1B:
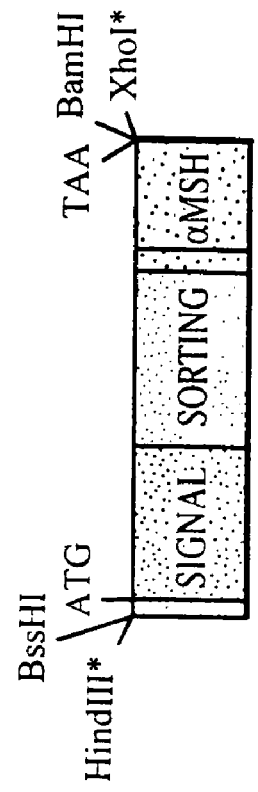
FIG. 1B depicts the structure of the miniPOMC polypeptide.

The structure of the POMC polypeptide is depicted in FIG. 1A. The location of various regions and features of POMC are indicated by reference to specific amino acid residues indicated below the depiction of the polypeptide. A polypeptide consisting of POMC amino acid sequences 1–26, 27–52, 138–150, and a linker sequence is depicted in FIG. 1B. This polypeptide has been designated miniPOMC. The construction and activity of nucleic acids encoding miniPOMC, as well as nucleic acids encoding other fusion polypeptides, is described in this and the following examples.

Oligonucleotides encoding the human POMC signal peptide, the human POMC sorting peptide, a partial junction peptide, and the sequence SYSMEHFRWGKPV (SEQ ID NO:1) were synthesized in vitro. The POMC oligonucleotides were constructed based upon the human POMC cDNA sequence (GenBank™ Accession NM_000939). The synthesized oligonucleotides were annealed and subcloned into HindIII and XhoI sites of pCMV-Script (Stratagene, San Diego) to generate the plasmid pCMV-miniPOMC. The following restriction enzyme sites were incorporated into the cDNA construct via oligonucleotide synthesis: HindIII and BssHII sites were placed upstream of the start codon; and BamHI and XhoI sites were placed downstream of the stop codon. Both the nucleotide (SEQ ID NO:43) and amino acid (SEQ ID NO:42) sequences of the miniPOMC construct are depicted in FIG. 2A.

Four additional oligonucleotides were synthesized encoding polypeptides containing the fusion polypeptide sequence of FIG. 2A, plus an additional one, three, or four amino acids at the carboxy end of the polypeptide. These constructs were designated ACTH(1-14), ACTH(1-16), ACTH(1-17), and α-MSH-f. FIG. 2B depicts the nucleotide (SEQ ID NO:46) and amino acid (SEQ ID NO:47) sequences of ACTH(1-14). FIG. 2C depicts the nucleotide (SEQ ID NO:48) and amino acid (SEQ ID NO:49) sequences of ACTH (1-16). FIG. 2D depicts the nucleotide (SEQ ID NO:50) and amino acid (SEQ ID NO:51) sequences of ACTH(1-17). FIG. 2E depicts the nucleotide (SEQ ID NO:79) and amino acid (SEQ ID NO:78) sequences of α-MSH-f. As compared to the miniPOMC polypeptide of FIG. 2A, ACTH(1-14) contains an additional G at its carboxy terminus, ACTH(1-16) contains an additional GKK at its carboxy terminus, ACTH (1-17) contains an additional GKKR (SEQ ID NO:45) at its carboxy terminus, and α-MSH-f contains an additional RSKR (SEQ ID NO:80) at its carboxy terminus. The sequence of GKK comprises and amidation signal. The nucleic acid constructs were subcloned in to the vector pCMV-Script, as described above.

Figure 3:
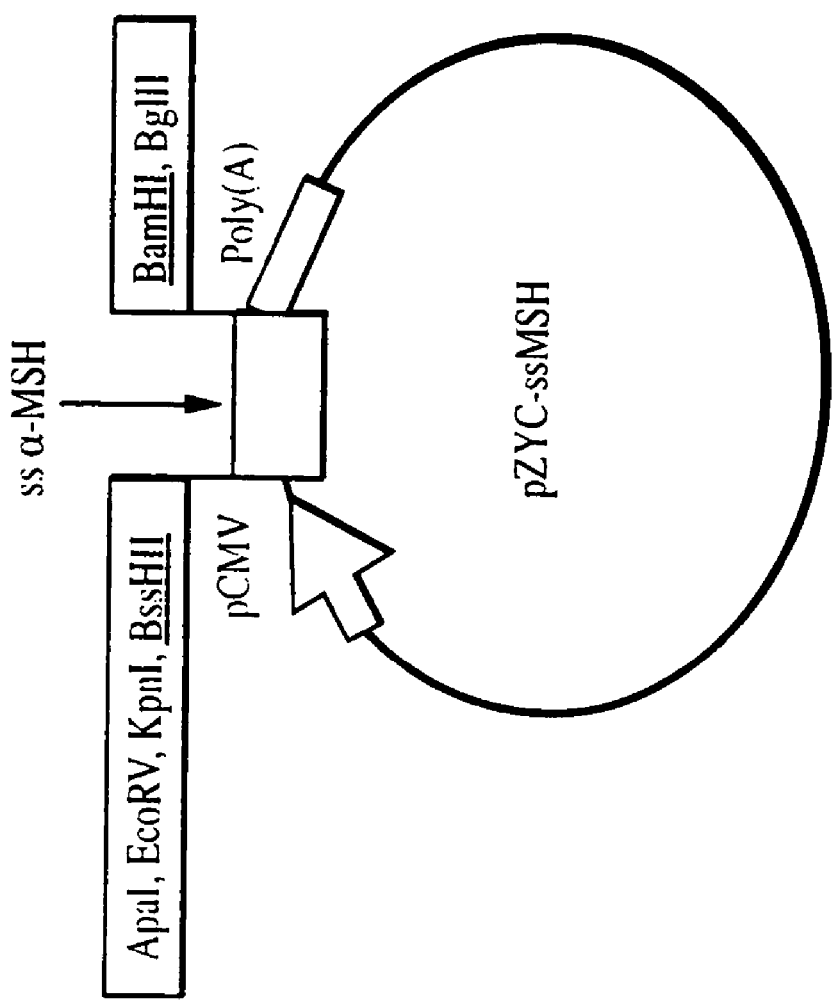
FIG. 3 depicts the expression vector pZYC-ssMSH.

The miniPOMC construct (FIG. 2A) was excised from pCMV-miniPOMC, by a BssHII and BamHI digest, and subcloned into the BssHII and BamHI sites of the expression vector pZYC to generate pZYC-miniPOMC (FIG. 3). pZYC is a modification of the pBIOTOPE plasmid described in U.S. Pat. No. 6,013,258.

Two copies of the miniPOMC construct (FIG. 2A) were subcloned into the vector pIRES (Clontech, Calif.) at multiple cloning sites A and B to generate the vector pIRES-2X miniPOMC. The pIRES-2X miniPOMC expression vector was generated as follows. pIRES was digested with NheI and the ends were blunted using the large (Klenow) fragment of DNA Polymerase I (BioLabs, MA). The resulting vector was further digested with XhoI. A miniPOMC fragment was excised from pCMV-miniPOMC by EcoRV (blunt) and XhoI digests. This fragment was then cloned into the blunt-XhoI pIRES vector to generate pIRES-miniPOMC. pIRES-miniPOMC was then digested with NotI, treated with Klenow to create a blunt end, and then further digested with XmaI. A miniPOMC fragment was removed from pCMV-miniPOMC, digested with XhoI, blunted with Klenow, and then further digested with XmaI. The XhoI-XmaI miniPOMC fragment was then cloned into the blunt-XmaI pIRES-miniPOMC vector to generate pIRES-2X miniPOMC.

Example 2

Construction of α-MSH/Serum Albumin Fusion Polypeptides

Figure 4:
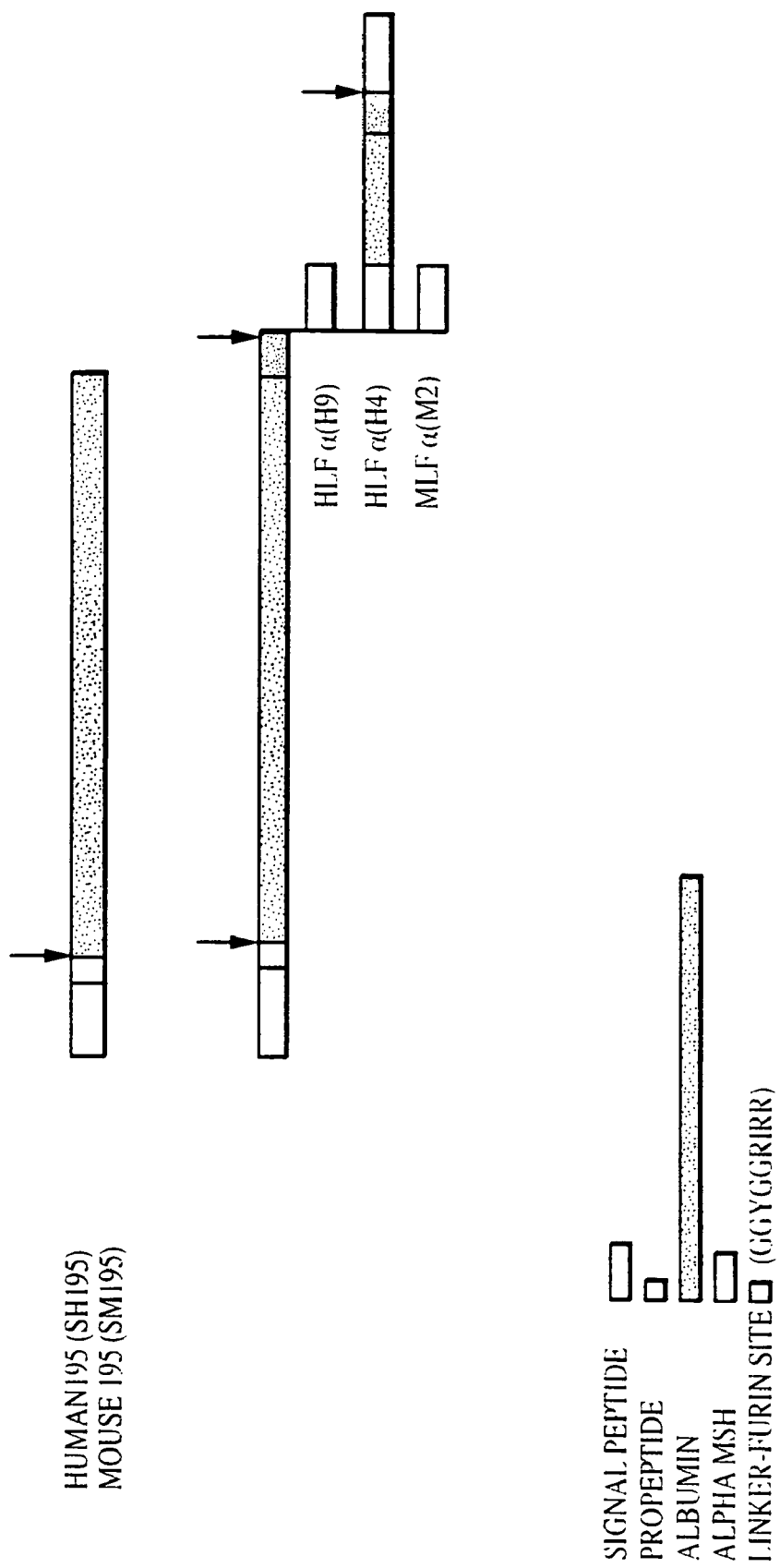
FIG. 4 depicts the structure of α-MSH/serum albumin fusion polypeptides. The arrows indicate sites of the polypeptide subject to cleavage by a protease.

Three α-MSH/serum albumin fusion polypeptides are depicted in FIG. 4. The polypeptides contain: (a) mouse serum albumin signal peptide (MKWVTFLLLLFVSG-SAFS; SEQ ID NO:52) or human serum albumin signal peptide (MKWVTFISLLFLFSSAYS; SEQ ID NO:53); (b) mouse or human serum albumin propeptide (RGVFRR; SEQ ID NO:54); (c) the first 195 amino acids of mouse serum albumin (EAHKSEIAHRYNDLGEQHFKGLV-LIAFSQYLQKCSYDEHAKLVQEVTD FAKTCVADE-SAANCDKSLHTLFGDKLCAIPNL-RENYGELADCCTKQEPERNECF LQHKDDNPSLPPFERPEAEAMCTS-FKENPTTFMGHYLHEVARRHPYFYAPELLY YAEQY-NEILTQCCAEADKESCLTPKLDGVKEKALVSSVR; SEQ ID NO:55) or human serum albumin (DAHKSE-VAHRFKDLGEENFKALVLIAFAQYLQQCPFEDH VKLVNEVTEFAKTCVADESAENCDK-SLHTLFGDKLCTVATLRETYGEMADCCA KQEP-ERNECFLQHKDDNPNLPRLVRPEVDVM-CTAFHDNEETFLKKYLYEIARRH PYFYAPELLFFAKRYKAAFTECCQAAD-KAACLLPKLDELRDEGKASSAK; SEQ ID NO:56); (d) a linker (GGYGG; SEQ ID NO:57); (e) a furin site (RIRR; SEQ ID NO:58); and (f) an α-MSH sequence SYSMEH-FRWGKPV (SEQ ID NO:1).

The linker and furin site sequences are introduced by PCR-based site-directed mutagenesis into the previously constructed serum albumin-α-MSH constructs. Two homologous long primers are designed, with the sequences for the linker and the furin site at the center, flanked by at least 25 bases homologous to the human or mouse serum albumin and α-MSH. During the PCR reaction, the primers anneal to the circular plasmid (at the homologous flanking sequences), while the non-homologous (linker and furin) sequences loop out. The PCR reaction is then digested with DpnI, a restriction enzyme that recognizes a four base pair consensus sequence on a methylated template.

Therefore, only the PCR product is left intact, and it is subsequently transformed into competent bacteria (DH5α cells). Colonies are picked for DNA preparation. Because a new restriction site is engineered in the primer, clones can be chosen after digest with that restriction enzyme (e.g., BamHI). The DNA is then sequenced for final confirmation.

The amino acid sequences of three constructs depicted in FIG. 4 are as follows:

```
HLFα(H9):
                                              (SEQ ID NO:59)
MKWVTFISLLFLFSSAYSRGVFRRDAHKSEVAHRFKDLGEENFKALVIAF
AQYLQQCPFEDHVKLVNEVTEFAKTCVADESAENCDKSLHTLFGDKLCTV
ATLRETYGEMADCCAKQEPERNECFLQHKDDNPNLPRLVRPEVDVMCTAF
HDNEETFLKKYLYEIARRHPYFYAPELLFFAKRYKAAFTECCQAADKACC
LLPKLDELRDEGKASSAKGGYGGRIRRSYSMEHFRWGKPV;

HLFα(H4):
                                              (SEQ ID NO:60)
MKWVTFISLLFLFSSAYSRGVFRRDAHKSEVAHRFKDLGEENFKALVLIA
FAQYLQQCPFEDHVKLVNEVTEFAKTCVADESAENCDKSLHTLFGKDLCT
```

-continued
VATLRETYGEMADCCAKQEPERNECFLQHKDDNPNLPRLVRPEVDVMCTA
FHDNEETFLKKYLYEIARRHPYFYAPELLFFAKRYKAAFTECCQAADKAA
CLLPKLDELRDEGKASSAKGGYGGRIRRSYSMEHFRWDGEKASSAKGGYG
GRIRRSYSMEHFRWGKPV;

MLFα(M2):

(SEQ ID NO:61)
MKWVTFLLLLFVSGSAFSRGVFRREAHKSEIAHRYNDLGEQHFKGLVLIA
FSQYLQKCSYDEHAKLVQEVTDFAKCVADESAANCDKSLHTLFGDKLCAI
PNLRENYGELADCCTKQEPERNECFLQHKDDNPSLPPFERPEAEMCTSFK
ENPTTFMGHYLHEVARRHPYFYAPELLYYAEQYNEILTQCCAEADKESCL
TPKLDGVKEKALVSSVRGGYGGRIRRSYSMEHFRWGKPV.

Constructs similar to those depicted in FIG. 4 can be prepared, wherein the α-MSH containing sequence SYSMEHFRWGKPV (SEQ ID NO:1) is replaced with another α-MSH containing sequence described herein, e.g., ACTH (1-14) (SEQ ID NO:62), ACTH(1-16) (SEQ ID NO:63), ACTH(1-17) (SEQ ID NO:64), or SYSMEHFRWGKPVRSKR (SEQ ID NO:69).

Nucleic acid constructs were also prepared encoding fusion polypeptides containing a serum albumin signal peptide (mouse or human), a serum albumin propeptide (mouse or human), the first 195 amino acids of serum albumin (mouse or human), a thrombin cleavage site (LAPR; SEQ ID NO:81), and an α-MSH sequence SYSMEHFRWGKPV (SEQ ID NO:1). The nucleic acid constructs were subcloned into the expression vector pZYC. The sequences of the encoded polypeptides were as follows.

H195T: MKWVTFISLLFLFSSAYSRGVFRRDAHKSEVAHRFKDLGEENFK ALVLIAFAQYLQQCPFEDHVKLVNEVTEFAKTCVADESAENCDKSLHTLFGDKLCTVATLRETYGEMADCCAKQEPERNECFLQHKDDNPNLPRLVRPEVDVMCTAF HDNEETFLKKYLYEIARRHPYFYAPELLFFAKRYKAAFTECCQAADKAACLLPKLDELRDEGKASSAKLAPRSYSMEHFRWGKPV (SEQ ID NO:82; human albumin-thrombin-α-MSH).

Mo195T: MKWVTFLLLLFVSGSAFSRGVFRREAHKSEIAHRYNDLGEQHF KGLVLIAFSQYLQKCSYDEHAKLVQEVTDFAKTCVADESAANCDKSLHTLFGDKLCAIPNLRENYGELADCCTKQEPERNECFLQHKDDNPSLPPFERPEAEAMCTSFK ENPTTFMGHYLHEVARRHPYFYAPELLYYAEQYNEILTQCCAEADKESCLTPKLDGVKEKALVSSVRLAPRSYSMEHFRWGKPV (SEQ ID NO:83; mouse albumin-thrombin-α-MSH).

Example 3

In Vitro Production of Alpha-MSH

The mouse melanoma cell line B 16/F10 (ATCC, Manassas, Va.) was grown in Iscove's Modified Dulbecco's Medium with 10% Fetal Bovine Serum (JRH Biosciences, KS) and was maintained at 37° C. in humidified 5% $CO_2$ incubator. Cells were seeded in six-well plates at $1×10^5$ cells/ml at a volume of 2 ml/well and incubated overnight. Cells were transfected with 3 μg of pCMV-miniPOMC, pIRES-2X miniPOMC, pZYC-miniPOMC, pCMV empty vector, or pZYC empty vector or were mock transfected using LipofectAMINE (Life Technologies, MD). The supernatants of the transfected cells were collected 48 hours post-transfection and used in a melanin assay.

Untransfected B16/F10 cells were seeded in 96-well pates at $2.5×10^4$ cells/ml, at 100 μl/well, and were incubated overnight in a 37° C. incubator. The next day, 100 μl of supernatant collected from transfected or mock-transfected cells (see above) was added to appropriate wells. Cells were then cultured for an additional four days before melanin synthesis was evaluated.

Melanin synthesis was measured in two ways, both of which measure the dark pigmentation that results from the stimulation of melanin synthesis. In the first method, the pigmentation of cells was evaluated by visual inspection (both by pelleting transfected cells and by examining a well of a 96 well plate containing transfected cells). These experiments demonstrated that cells transfected with miniPOMC-encoding expression vectors became dark as compared to cells transfected with an empty vector or mock transfected cells.

Figure 5:
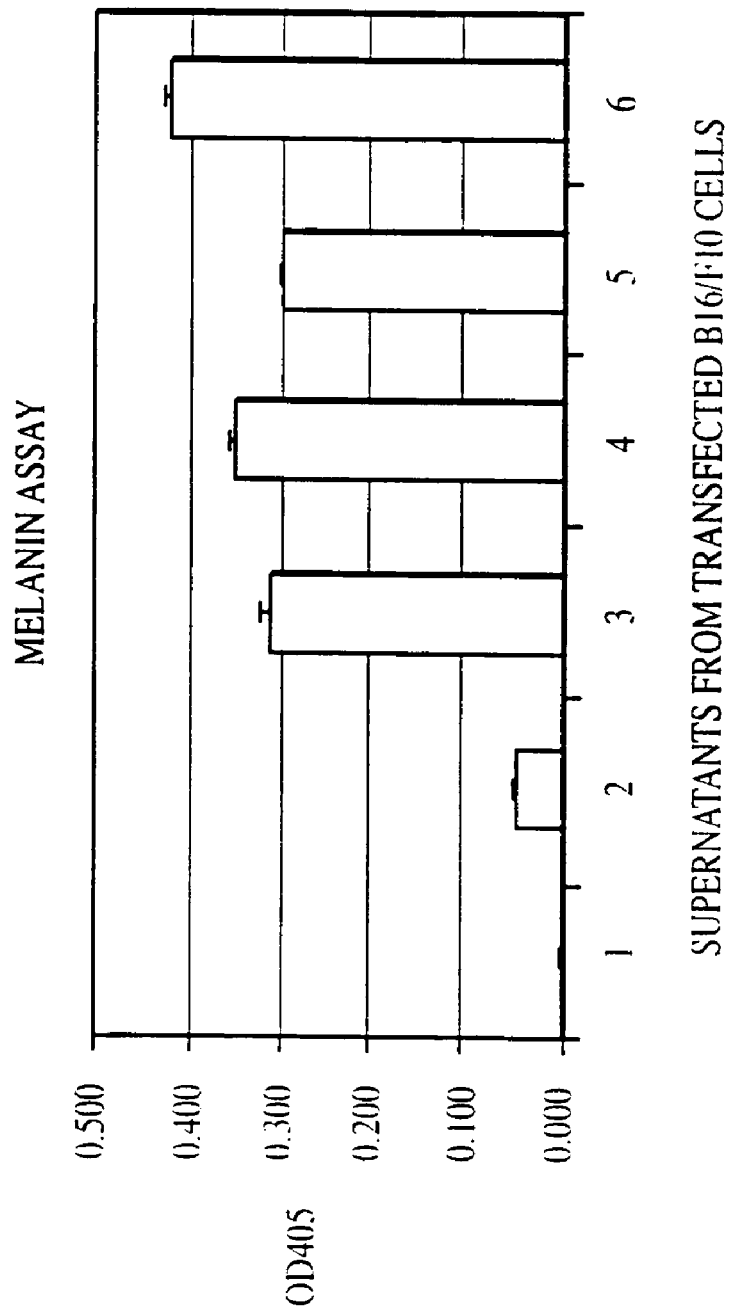
FIG. 5 depicts melanin synthesis, as measured by absorbance readings at 405 nm, by untransfected B16/F10 cells treated with supernatant produced by B16/F10 cells transfected with: (1) mock transfection (no vector); (2) pCMV-Script control vector; (3) pCMV-miniPOMC; (4) pZYC-miniPOMC; (5) pCMV-miniPOMC; or (6) pIRES-2X miniPOMC.
Figure 6:
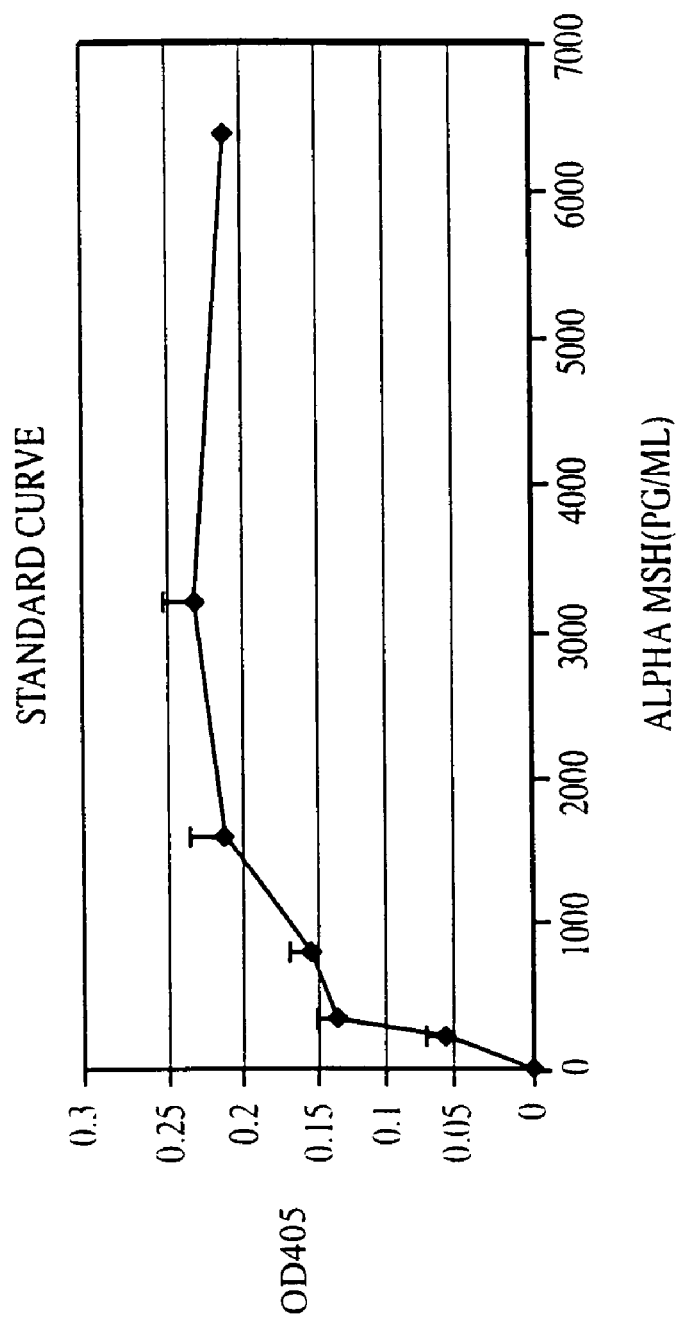
FIG. 6 depicts melanin synthesis, as measured by absorbance readings at 405 nm, by B16/F10 cells to which various concentrations of alpha-MSH peptide have been added.

In the second method, pigmentation was measured by taking absorbance readings of untransfected cells following the treatments described above. FIG. 5 shows melanin synthesis induced by the various miniPOMC-encoding constructs and controls. Melanogeneis-associated pigmentation was determined by taking absorbance readings of the wells of a 96 well plate at 405 nm using a plate reader. The samples depicted in FIG. 5 are as follows: (1) mock transfected cells; (2) pCMV-Script vector control; (3) pCMV-miniPOMC; (4) pZYC-miniPOMC; (5) pCMV-miniPOMC; and (6) pIRES-2X miniPOMC. In determining the absorbance readings presented for each bar in FIG. 5, 100 μl of supernatant from each of the six transfectants (or mock transfectants) above was transferred to a well of a 96 well plate containing 100 μl of media, but no cells. The absorbance reading taken from this control well was subtracted from that of its corresponding well containing untransfected cells (to determine the melanin produced by the untransfected cells). Commercially obtained alpha-MSH peptides (Peninsula Laboratories, CA) were used to generate standard curves for melanin synthesis at various alpha MSH concentrations (FIG. 6).

Figure 7:
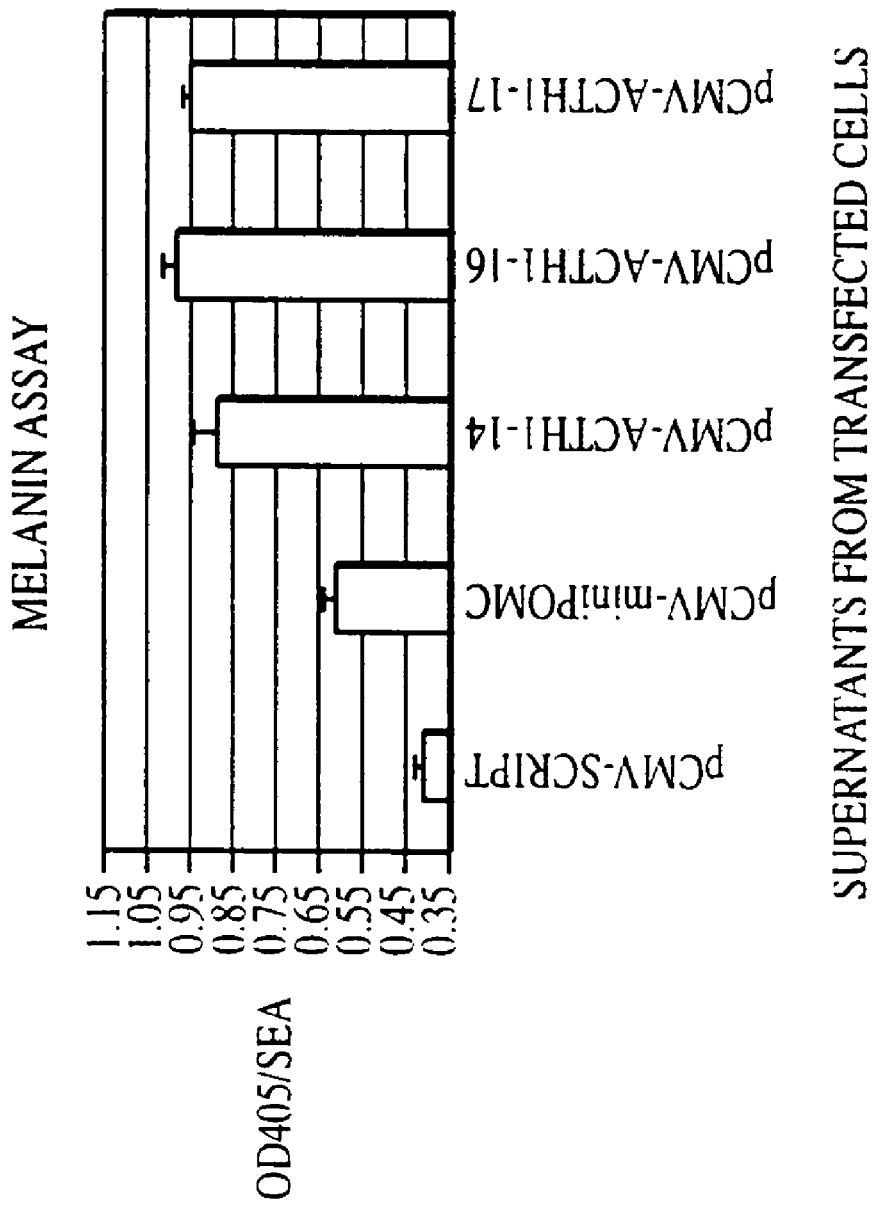
FIG. 7 depicts melanin synthesis, as measured by absorbance readings at 405 nm, by untransfected B16/F10 cells treated with supernatant produced by B16/F10 cells transfected with: (1) pCMV-Script control vector; (2) pCMV-miniPOMC; (3) pCMV-ACTH(1-14); (4) pCMV-ACTH(1-16); or (5) pCMV-ACTH(1-17).

The constructs depicted in FIGS. 2A–2B were also tested for their ability to induce pigmentation in B16/F10cells in the assay described above. As shown in FIG. 7, the following constructs were evaluated: (1) pCMV-Script vector control; (2) pCMV-miniPOMC; (3) pCMV-ACTH(1-14); (4) pCMV-ACTH(1-16); and (5) pCMV-ACTH(1-17). Absorbance readings were taken as described above. The readings were normalized to secretory alkaline phosphatase (SEAP) transfected cells, which corrects for variability in transfection.

Figure 8A:
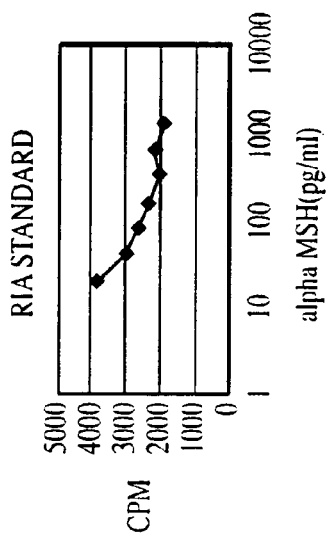
FIG. 8 depicts the results of a radioimmunoassay (RIA) that detects α-MSH in the supernatant of cells transfected with the following constructs: (1) mock transfected cells; (2) pCMV-Script control vector; (3) pCMV-miniPOMC; (4) pCMV-ACTH(1-14); (5) pCMV-ACTH(1-16); or (6) pCMV-ACTH(1-17).
Figure 8B:
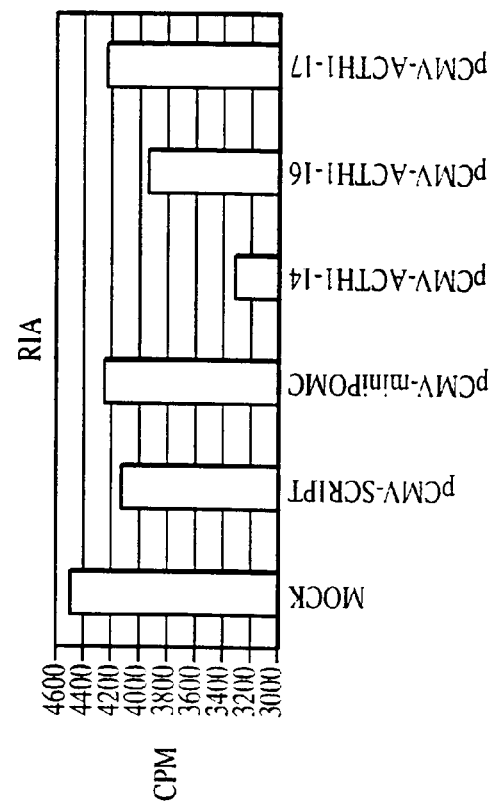

FIG. 8 depicts the results of a radio-immunoassay (RIA) which measured standard alpha MSH and supernatants from cells transfected with various constructs described herein. The samples depicted in FIG. 8 are as follows: (1) mock transfected cells; (2) pCMV-Script vector control; (3) pCMV-miniPOMC; (4) pCMV-ACTH(1-14); (5) pCMV-ACTH(1-16); and (6) pCMV-ACTH(1-17). Because the assay is competitive, a lower CPM reading indicates higher levels of alpha MSH in the sample.

In a RIA, a standard peptide at serial dilutions or samples that contain target peptides are added together. A primary rabbit polyclonal antibody to the target peptide is added, followed by overnight incubation at 4° C. Following incubation, a target peptide labeled with $I^{125}$ is added, followed by another overnight incubation at 4° C. Following incubation, goat anti-rabbit IgG serum and normal rabbit serum are added and samples are incubated at room temperature for 90 minutes. Samples are then centrifuged at 3,000 rpm for 20 minutes. The pellets are re-suspended in PBS buffer and transferred to scintillation vials where CPM is measured by a scintillation counter.

FIG. 9 depicts the levels of α-MSH produced in various cell types trasnfected with constructs described herein. The expression constructs used were as follows: (1) pCMV-ssMSH; (2) pZYC-ssMSH; and (3) pIRES-2XssMSH. Production of α-MSH was evaluated in B16/F10mouse melanoma cells, GH3 rat pituitary cells, RAW mouse macrophage cells, 293 T human kidney cells, and 3T3 mouse fibroblast cells.

FIG. 10 depicts amounts of melanin synthesized by untransfected B16/F10 cells treated with supernatant produced by B16/F10 cells transfected with α-MSH/Serum Albumin Fusion Polypeptides described in Example 2 or negative controls. Negative control constructs SH195 and SM195 were constructed by placing a stop codon after the nucleotide sequence encoding the 195 amino acid human serum albumin protein or mouse serum albumin protein, as described in Example 2. The results for samples depicted in FIG. 10 are as follows: (1) SH195 (human serum albumin fusion polypeptide); (2) SM195 (mouse serum albumin fusion polypeptide); (3) HLFα(H9); and (4)MLFα(M2).

Example 4

In Vivo Production of Alpha-MSH

Figure 11A:
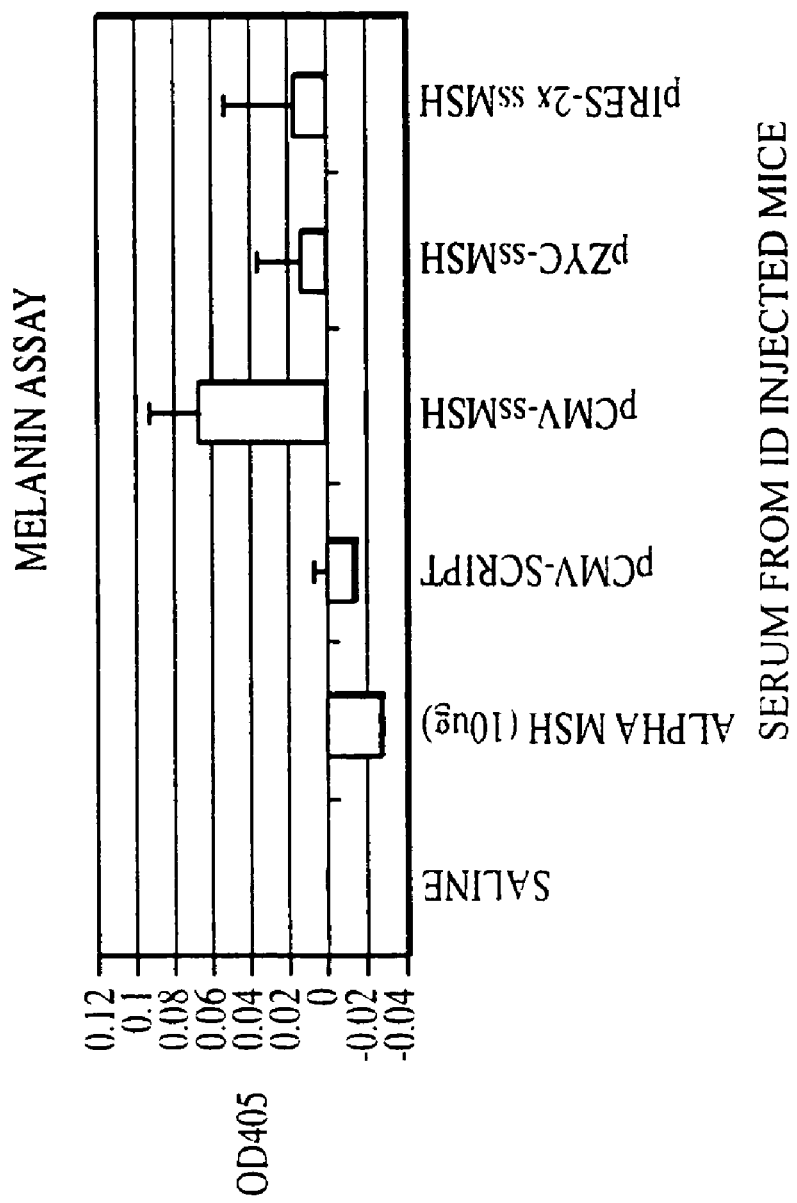
FIGS. 11A and 11B depict melanin synthesis, as measured by absorbance readings at 405 nm, by untransfected B16/F10 cells treated with sera from mice injected intradermally (FIG. 11A) or intravenously (FIG. 11B) with miniPOMC-encoding expression vectors.
Figure 11B:
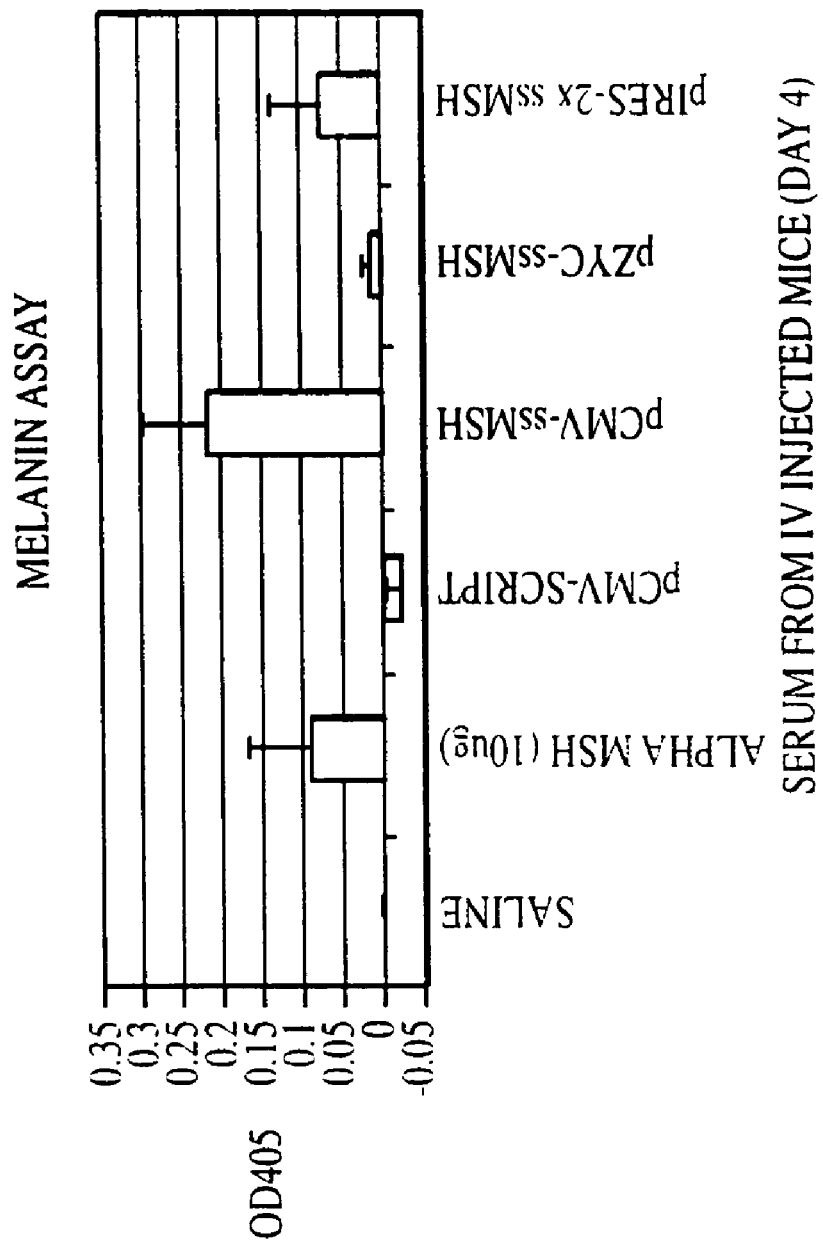

The ability of the expression vectors described in Example 1 to cause the production of alpha-MSH in vivo was evaluated as follows. Six groups of mice, with three animals per group, were set up and each group was injected with one of the following: (1) saline; (2) 10 µg alpha MSH Peptide; (3) 100 µg pCMV-Script; (4) 100 µg pCMV-miniPOMC; (5) 100 µg pZYC-miniPOMC; or (6) 100 µg pIRES-2X miniPOMC. The injections were either intradermal or intravenous. Mice were bled (intraorbital) at 30 minutes and on day 1, day 4, day 7, day 11, and day 15 post injection. One hundred µl of blood was collected and sera was stored at −80° C. until tested in the in vitro melanin bioassay described in Example 3. To carry out the melanin assay, 10 µl of sera was added to 90 µl of media, and this 100 µl sample was added to a well containing untransfected B16/F10 cells in 100 µl as described above. FIGS. 11A and 11B show the in vivo secretion of alpha-MSH four days following intradermal (FIG. 11A) and intravenous (FIG. 11B) injections.

Example 5

Assays to Detect NF-kB Activation

One mechanism by which α-MSH may function is through the inhibition of NF-KB activation. Specifically, the binding of α-MSH to an MCR receptor can prevent the phosphorylation of the IKb subunit of the NF-kB-I-kB complex and thereby inhibit NF-kB activation.

An assay using a luciferase reporter construct was used to assess the NF-kB state (active or inactive) when cells transfected with various α-MSH expressing plasmids were stimulated to induce NF-kB activation. Cells were transfected with pNF-kB-Luc, an α-MSH vector, and a SEAP expression vector (to correct for variability in transfection). Cells were then treated with either TNF-α or LPS to induce NF-kB activation and thus the expression of luciferase. Media was collected and an assay was performed to measure SEAP levels (using a kit provided by TROPIX, PE Biosystems). Cells were then lysed and luciferase activity was measured in the cell lysate. To normalize luciferase activity to the SEAP level, the luciferase count (cps) was divided by the SEAP count (cps). The fold induction of luciferase activity was then calculated by dividing the normalized luciferase cps of the treated sample by the normalized luciferase cps of the untreated sample.

Figure 12:
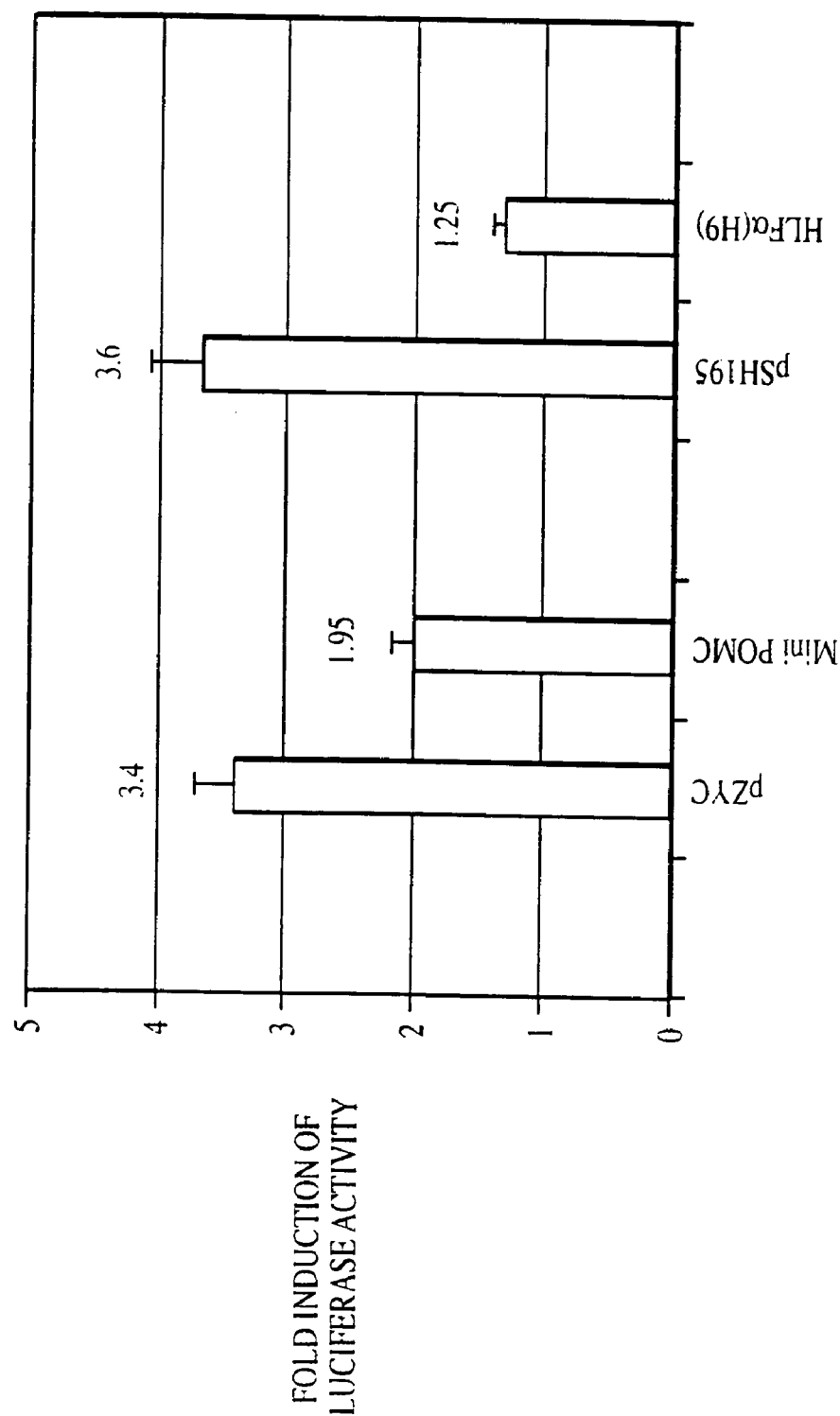
FIG. 12 depicts the activity level of NF-kB in HeLa cells transfected with α-MSH expressing constructs. For each construct, luciferase activity was measured relative to vector controls.

FIG. 12 depicts the activation of NF-kB in HeLa cells treated with TNF-α and transfected with either an α-MSH expressing construct or a control construct. Cells were transfected with: (1) pZYC empty vector, (2) pZYC-miniPOMC; (3) pSH195 empty vector; or (4) HLFα(H9).

Figure 13A:
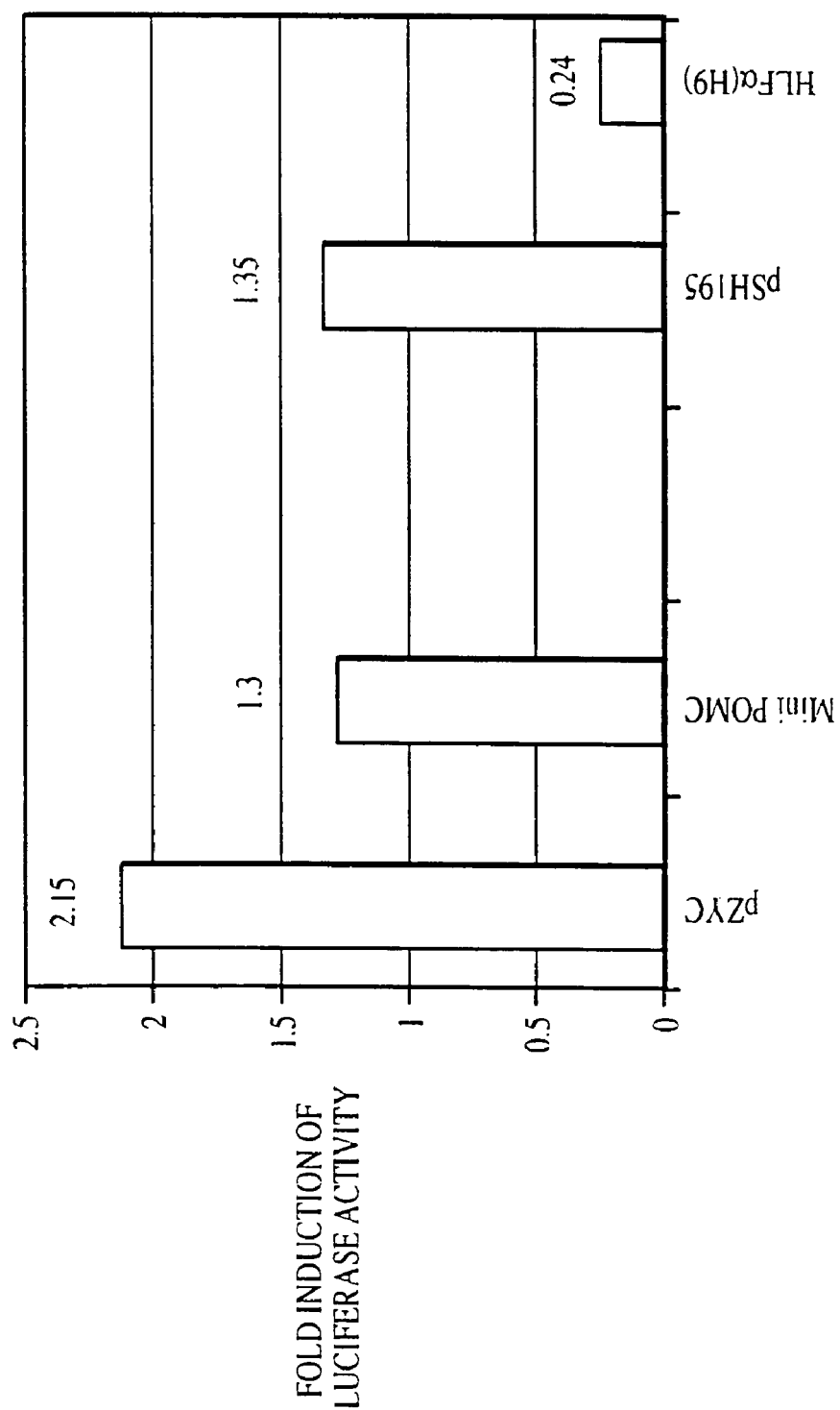
FIGS. 13A and 13B depict the activity level of NF-kB in RAW 264.7 mouse macrophage cells transfected with α-MSH expressing constructs. For each construct, luciferase activity was measured relative to vector controls.

FIG. 13A depicts the activation of NF-KB in RAW 264.7 mouse macrophage cells treated with 10 µg/ml LPS and transfected with either an α-MSH expressing construct or a control construct. Cells were transfected with: (1) pZYC empty vector, (2) pZYC-miniPOMC; (3) pSH195 empty vector; or (4) HLFα(H9). In addition to RAW 264.7 cells, inhibition of NF-kB activation was also detected in Sol8 muscle cells treated with 1 or 10 µg/ml LPS and transfected with a HLFα(H9)-encoding nucleic acid construct (not shown).

Figure 13B:
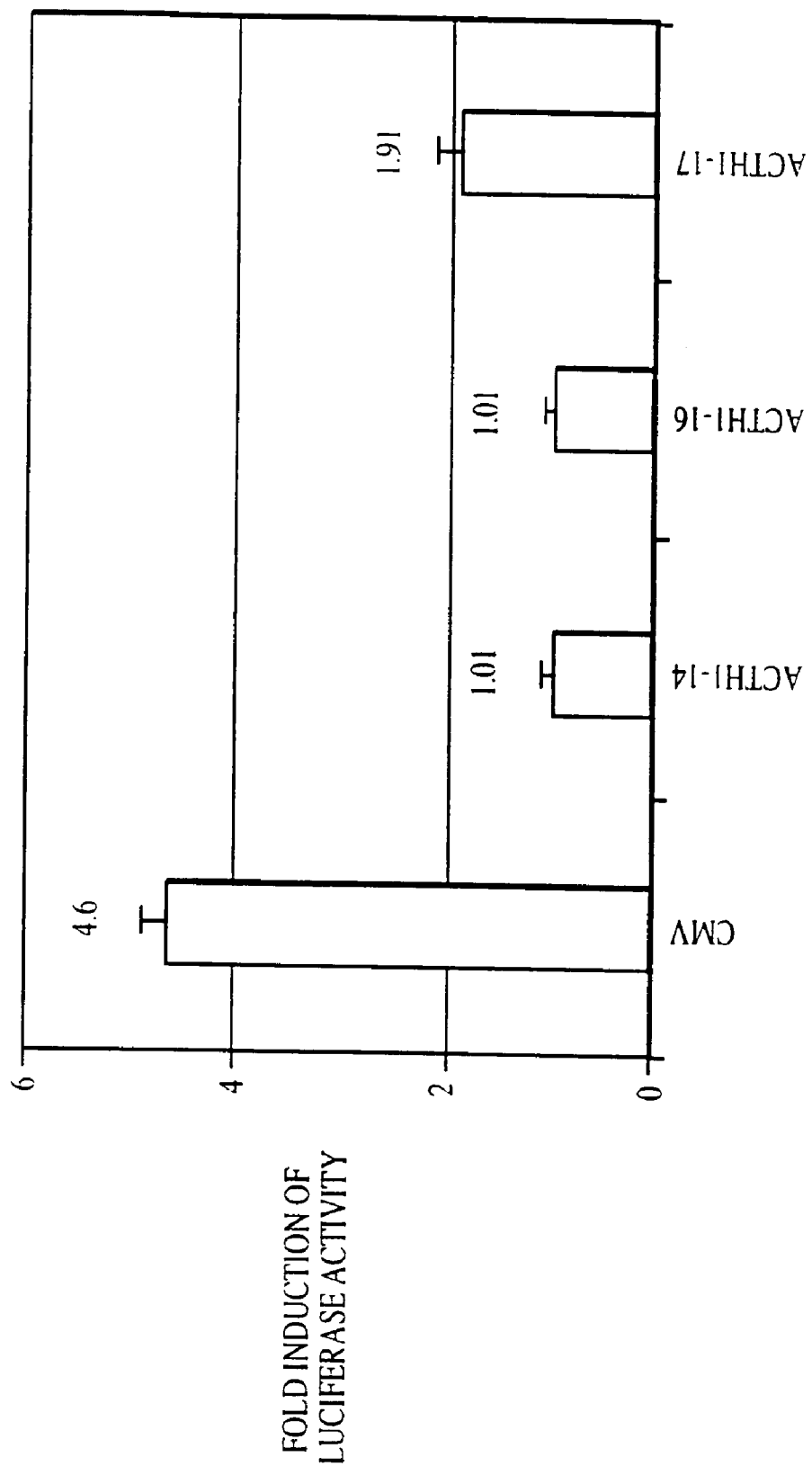

FIG. 13B depicts the activation of NF-KB in RAW 264.7 mouse macrophage cells treated with 10 µg/ml LPS and transfected with either an α-MSH expressing construct or a control construct. Cells were transfected with: (1) pCMV empty vector, (2) pCMV-ACTH(1-14); (3) pCMV-ACTH (1-16); or (4) pCMV-ACTH(1-17).

Figure 14:
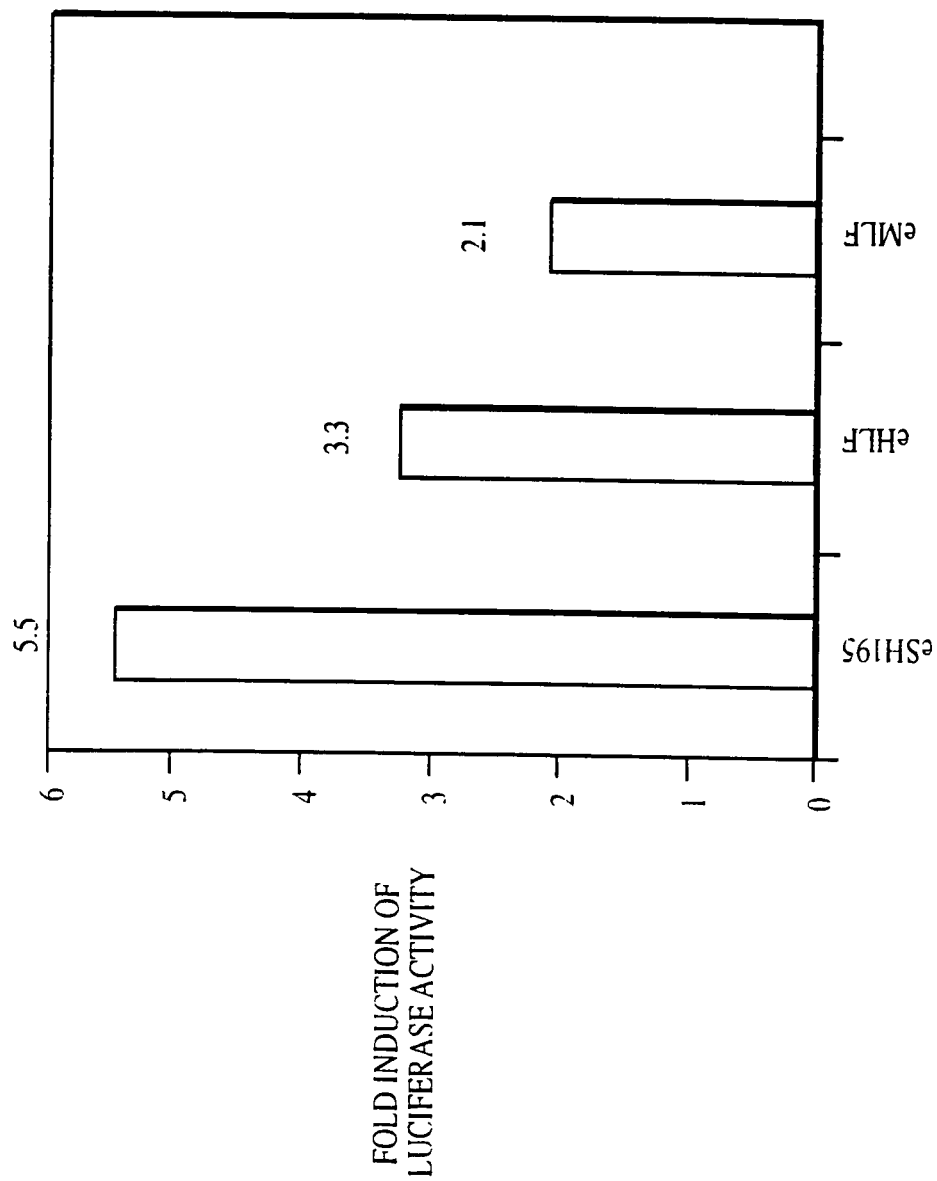
FIG. 14 depicts the activation of NF-kB in Sol8 mouse muscle cells transfected with α-MSH expressing constructs. For each construct, luciferase activity was measured relative to vector controls.

FIG. 14 depicts the activation of NF-kB in Sol8 mouse muscle cells treated with TNF-α and transfected with either an α-MSH expressing construct or a control construct. Cells were transfected with: (1) peSH195; (2) eHLFα(H9); or (3) eMLFα(M2). The expression vectors peSH195, eHLFα (H9), and eMLFα(M2) encode the polypeptides depicted in FIG. 4 (Example 2) and contain the human elongation factor 1-α promoter in place of the CMV promoter.

In a second assay, direct binding ELISA was used to detect NF-kB activation. Cells were transfected with an α-MSH vector and treated with TNF-α or LPS to induce NF-kB activation. After cell lysis, the lysate was added to 96-well plates coated with an NF-kB-binding oligonucleotide. An anti-NF-kB antibody was then added to the wells. Following incubation with an anti-IgG horse radish peroxidase conjugate, color was developed and the optical density was determined at 450 nm. The Trans-AM™ NF-kB binding assay from Active Motif (Carlsbad, Calif.) was used to detect NF-kB activation by this method.

Figure 15A:
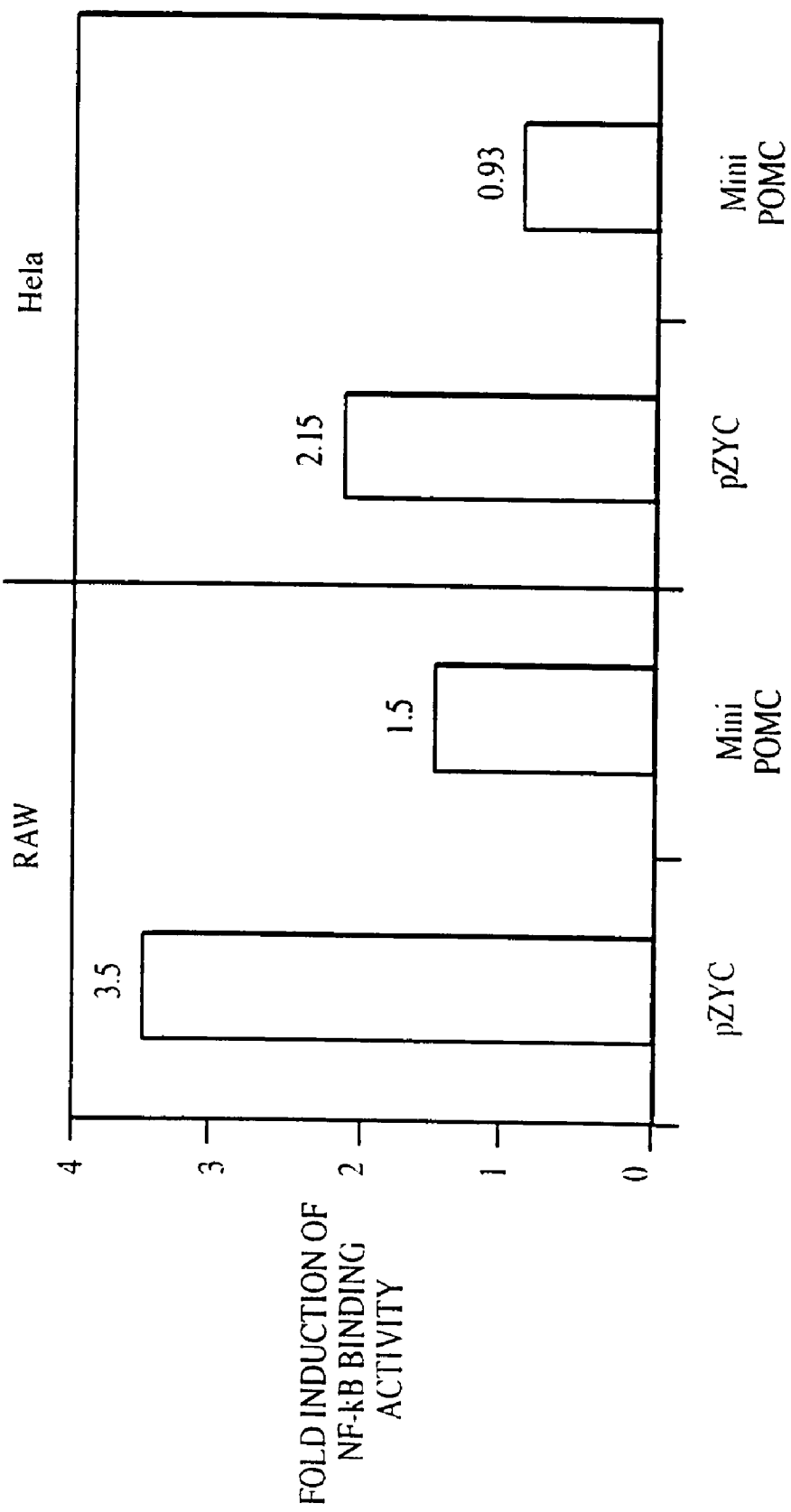
FIG. 15A depicts the results of a direct binding assay used to detect NF-kB activation in RAW 264.7 mouse macrophage and HeLa cells transfected with pZYC-ssMSH as compared to a control vector.
Figure 15B:
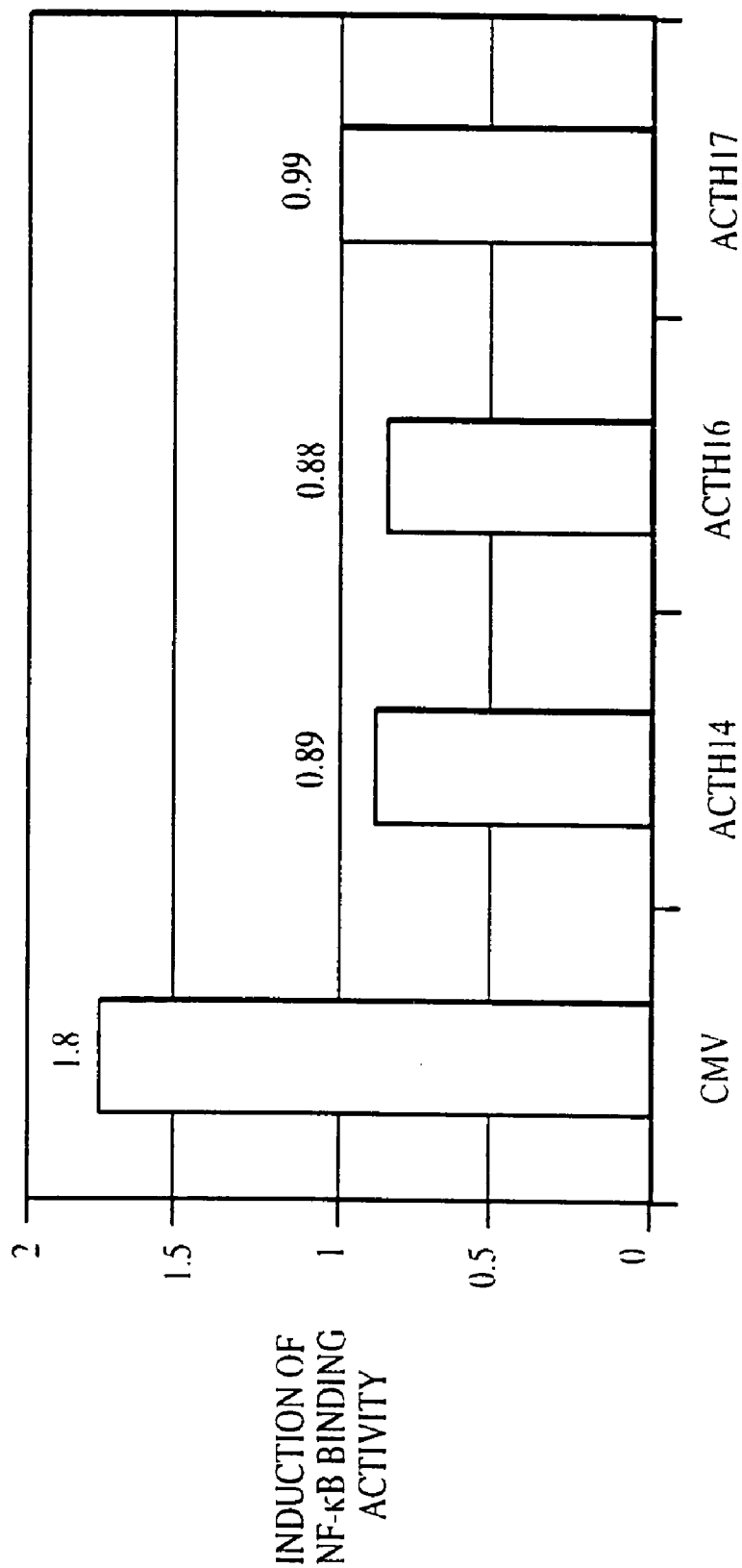
FIG. 15B depicts the results of a direct binding assay used to detect NF-kB activation in RAW 264.7 mouse macrophage transfected with pCMV empty vector, pCMV-ACTH(1-14), pCMV-ACTH(1-16), or pCMV-ACTH(1-17).

FIG. 15A depicts the activation of NF-kB, as measured by the Trans-AM™ NF-kB binding assay, in RAW and HeLa cells that have been transfected with either: (1) pZYC empty vector; or (2) pZYC-miniPOMC. FIG. 15B depicts the activation of NF-kB, as measured by the Trans-AM™ NF-kB binding assay, in RAW cells that have been transfected with: (1) pCMV empty vector, (2) pCMV-ACTH(1-14); (3) pCMV-ACTH(1-16); or (4) pCMV-ACTH(1-17).

Example 6

Use of an Alpha-MSH Analog and an Alpha-MSH Encoding Nucleic Acid to Reduce Severity of Experimental Autoimmune Encephalitis (EAE)

The ability of an α-MSH analog to reduce the severity of EAE was evaluated as follows. Groups of 10 mice each were induced with disease by the following protocol. On day 0, each mouse was administered subcutaneously at the base of the tail 300 µg of Myelin Basic Protein (Sigma) emulsified in Freunds adjuvant (Sigma) containing 2 mg/ml H37RA (Gibco). The mice also received three intra-peritoneal injections containing 400 ng of pertussis toxin (List Biologicals)

on days 0, 2, and 7. The animals were monitored for disease daily starting on day 7. Symptoms were monitored visually and each mouse was given a daily score according to the following scale:

| Score | Symptoms |
|---|---|
| 0 | normal mouse; no overt signs of disease |
| 1 | limp tail or hind limp weakness but not both |
| 2 | limp tail and hind leg weakness |
| 3 | partial hind leg paralysis |
| 4 | complete hind limp paralysis |
| 5 | moribund state |

Figure 16A:
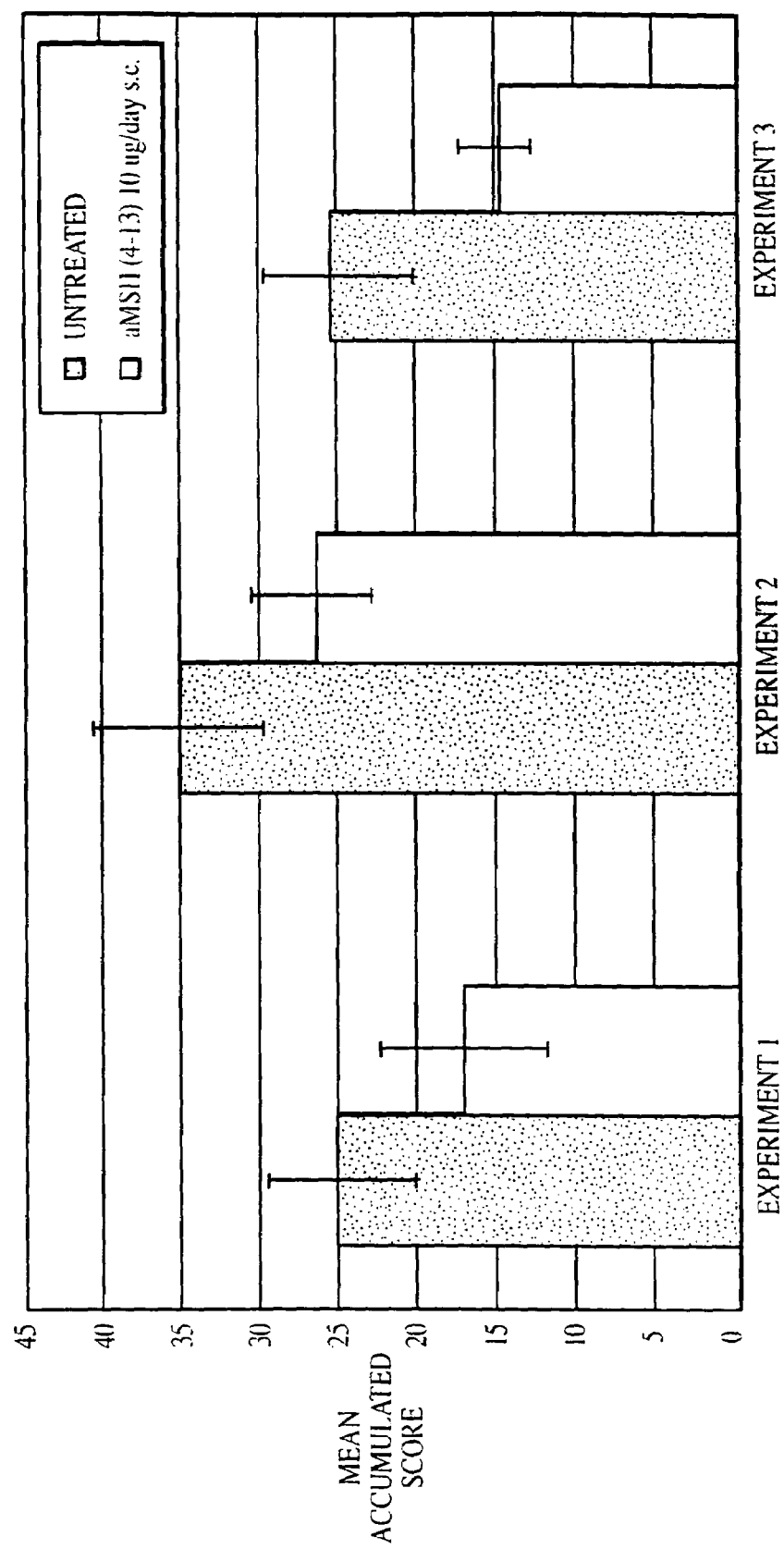
FIG. 16A depicts the results of three separate experiments in which an α-MSH peptide was used to treat Experimental Autoimmune Encephalitis (EAE).

Beginning on the day that symptoms first appeared, 10 μg/day of α-MSH analog was administered subcutaneously each day for a minimum of 14 days. The α-MSH (4-13) analog used had the structure Ac-Cys-Glu-His-DPhe-Arg-Trp-Cys-Lys-Pro-Val-NH$_2$, with a disulfide bridge between Cys1 and Cys7. This α-MSH analog was obtained from Peninsula Laboratories, Inc. (San Carlos, Calif.). This analog was described in Cody et al. (1985) J. Med. Chem. 28:583–588. FIG. 16 shows the results of three separate experiments (10 mice were evaluated in each experiment). The score for each mouse was totaled at the end of the study and the average accumulated score for each group of mice is shown in FIG. 16A.

Figure 16B:
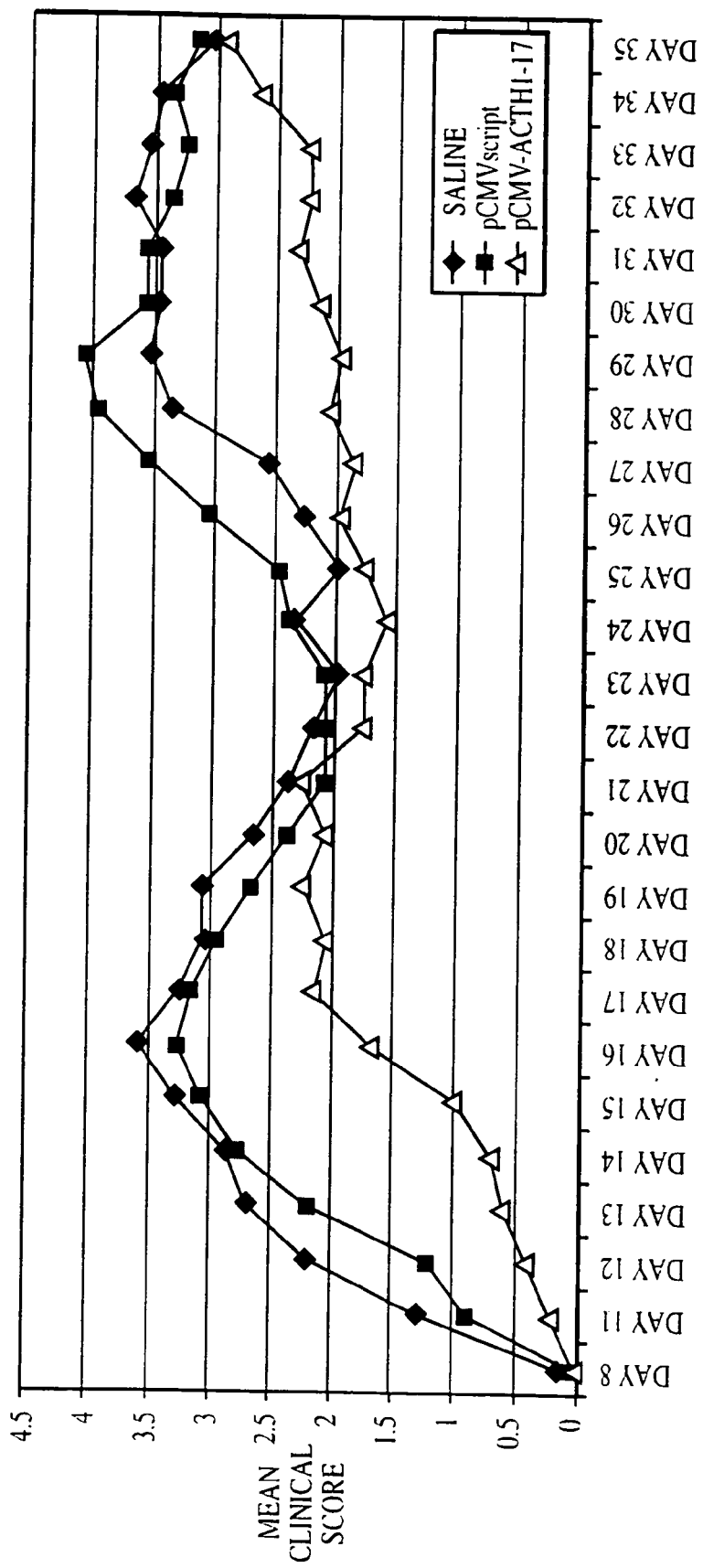
FIG. 16B depicts the depicts the mean accumulated EAE clinical score in mice treated with an α-MSH encoding nucleic acid.
Figure 16C:
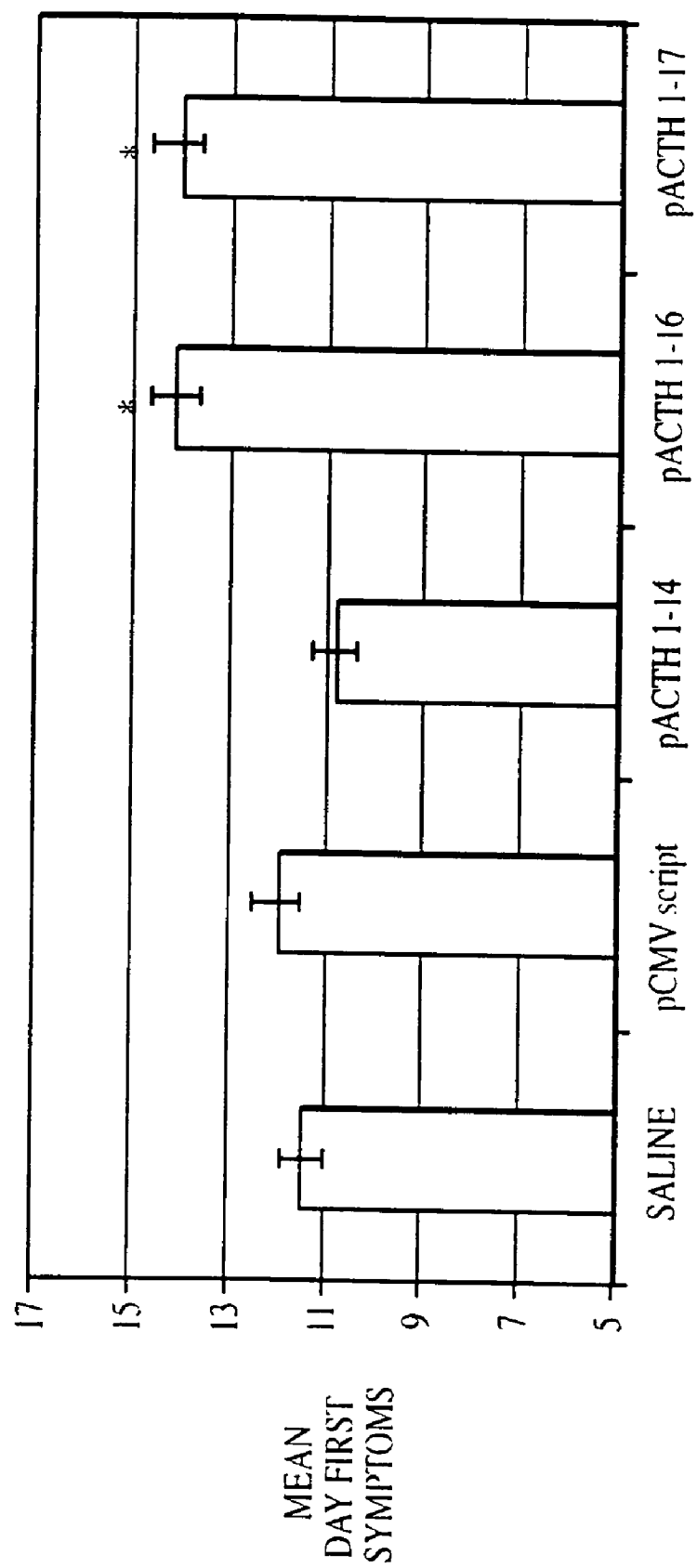
FIG. 16C depicts the mean day of the onset of EAE clinical symptoms in mice treated with an α-MSH encoding nucleic acid.

In a separate set of experiments, EAE was induced as described above and mice were treated with an α-MSH encoding nucleic acid. 100 μg of an α-MSH encoding plasmid, an empty vector, or a saline control were injected intra-muscularly on days 0, 7, 14, 21, and 28. FIG. 16B depicts the mean accumulated clinical score for each group of mice treated with either saline, pCMVscript, or pCMV-ACTH(1-17). FIG. 16C depicts the mean day of the onset of clinical symptoms in mice treated with: (1) saline; (2) pCMV empty vector, (3) pCMV-ACTH(1-14); (4) pCMV-ACTH(1-16); or (5) pCMV-ACTH(1-17).

Example 7

Use of an Alpha-MSH Analog and an Alpha-MSH Encoding Nucleic Acid in a Murine Model of Inflammatory Bowel Disease Inflammatory Bowel Disease (IBD) was induced in mice by the administration of trinitrobenzenesulphonic acid (TNBS), in 40% EtOH, to the mice. The loose stool associated with the IBD induced in this model resulted in a detectable weight loss in the TNBS-treated mice. The IBD model is described in, for example, Keates et al. (2000) Gastroenterology 119:972–82.

Figure 17A:
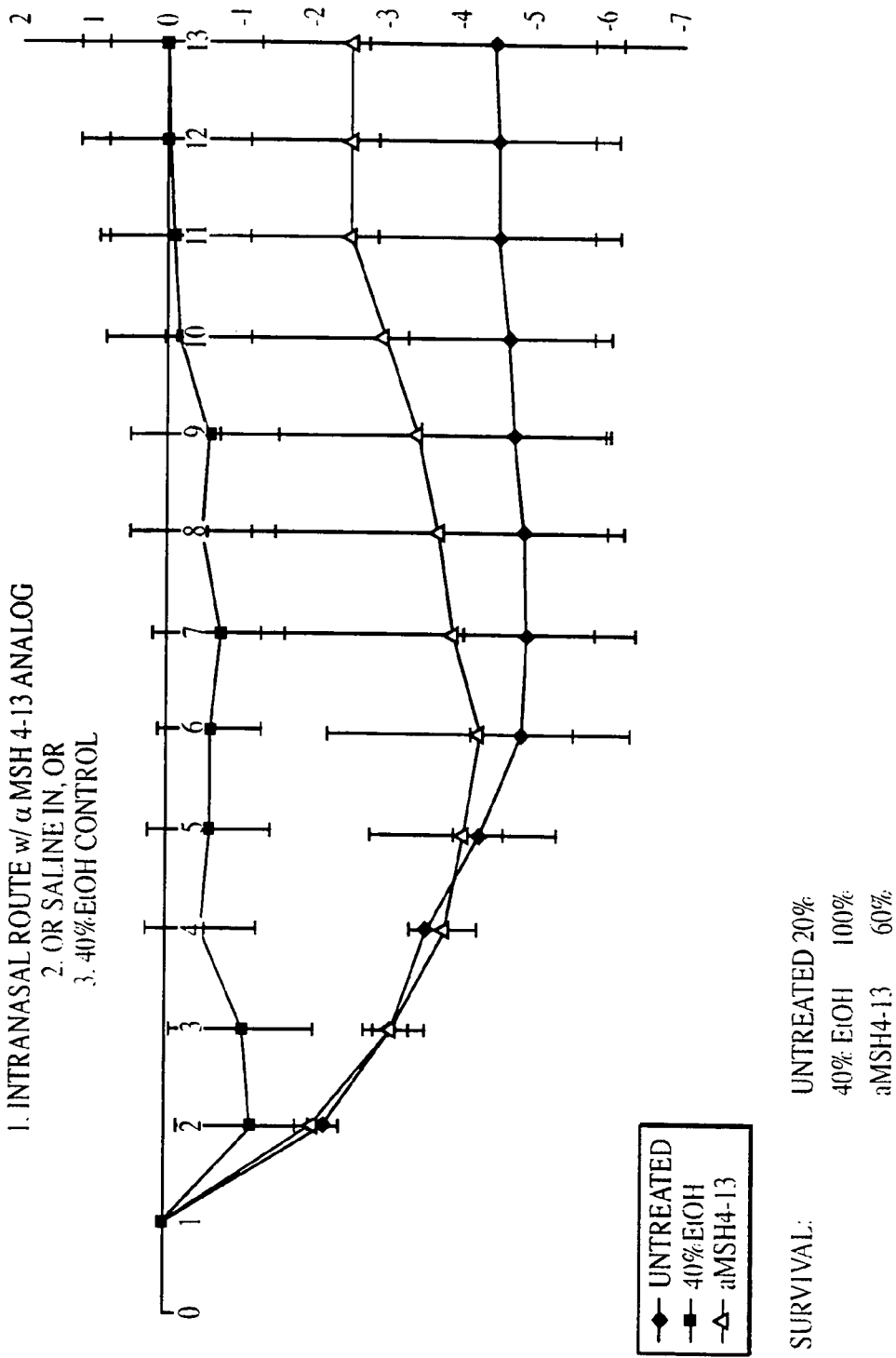
FIG. 17A depicts the results of an experiment in which an α-MSH analog was used to treat Inflammatory Bowel Disease (IBD).

As shown in FIG. 17A, an α-MSH(4-13) analog (described in Example 6) decreased the weight loss induced in the IBD model. The administration of EtOH alone (no TNBS) caused no weight loss in the animals. The "untreated" mice were given only the TNBS administration. The aMSH(4-13) mice were given an administration of TNBS, together with an intranasal administration of the aMSH(4-13) analog, which reduced the severity of the TNBS-induced weight loss. The aMSH(4-13) analog also increased the survival of the TNBS-treated animals.

Figure 17B:
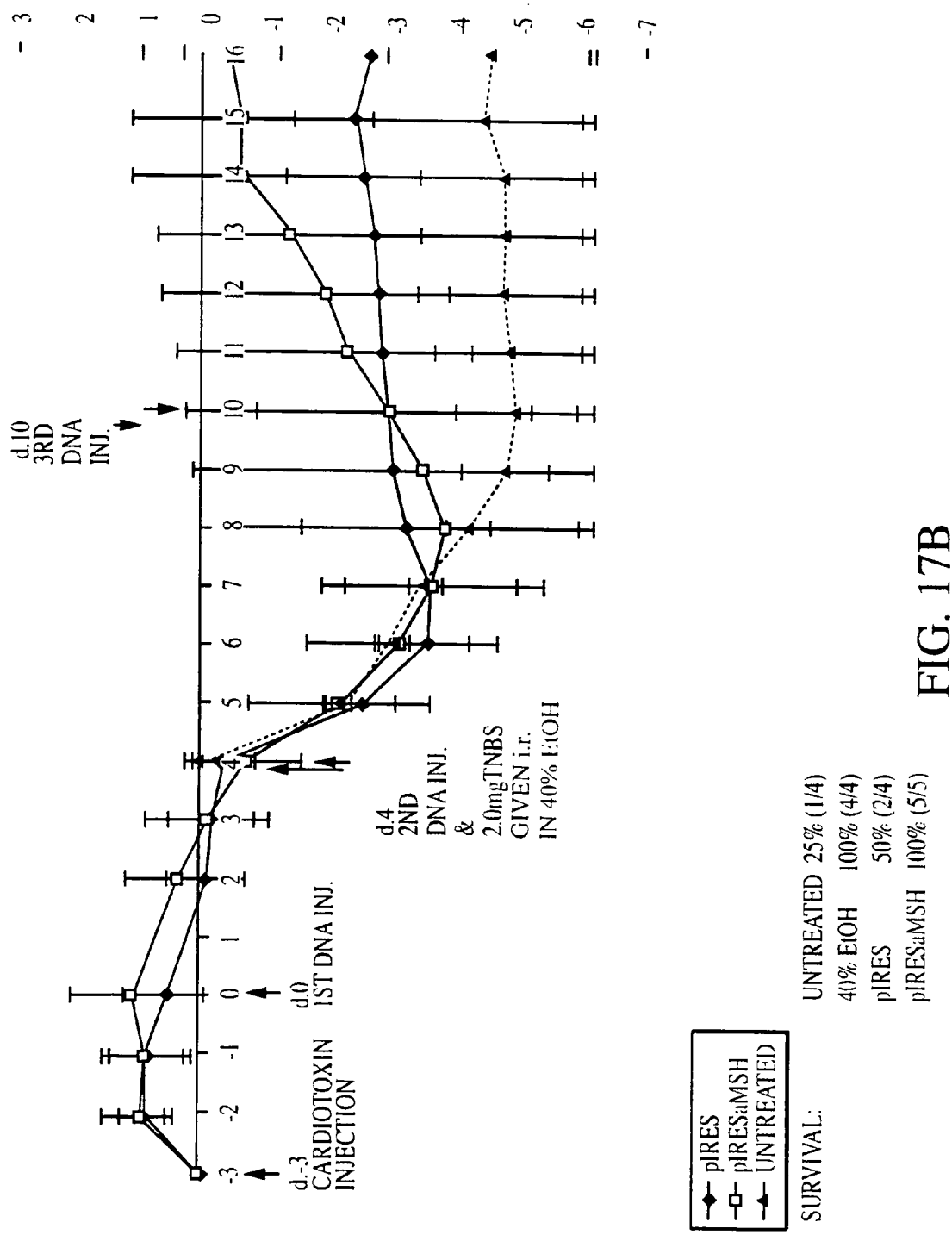
FIG. 17B depicts the results of an experiment in which a miniPOMC vector was used to treat IBD.

As shown in FIG. 17B, administration of the pIRES-miniPOMC vector also reduced the severity of weight loss induced in the IBD model. The vector was administered by intramuscular injections at the timepoints indicated in the figure. Administration of the pIRES-miniPOMC vector also improved the survival of the TNBS-treated animals.

Example 8

Figure 18A:
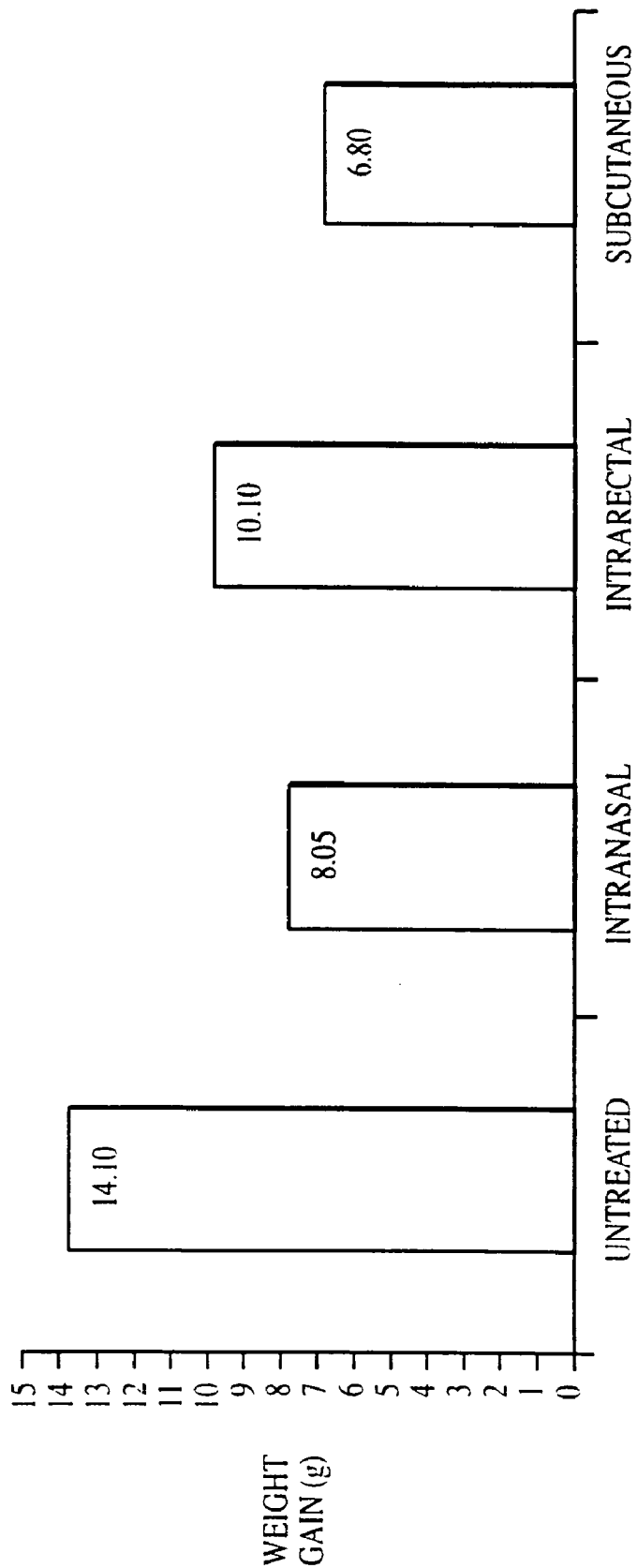
FIG. 18A depicts the results of an experiment in which an α-MSH analog was used to treat obesity.
Figure 18B:
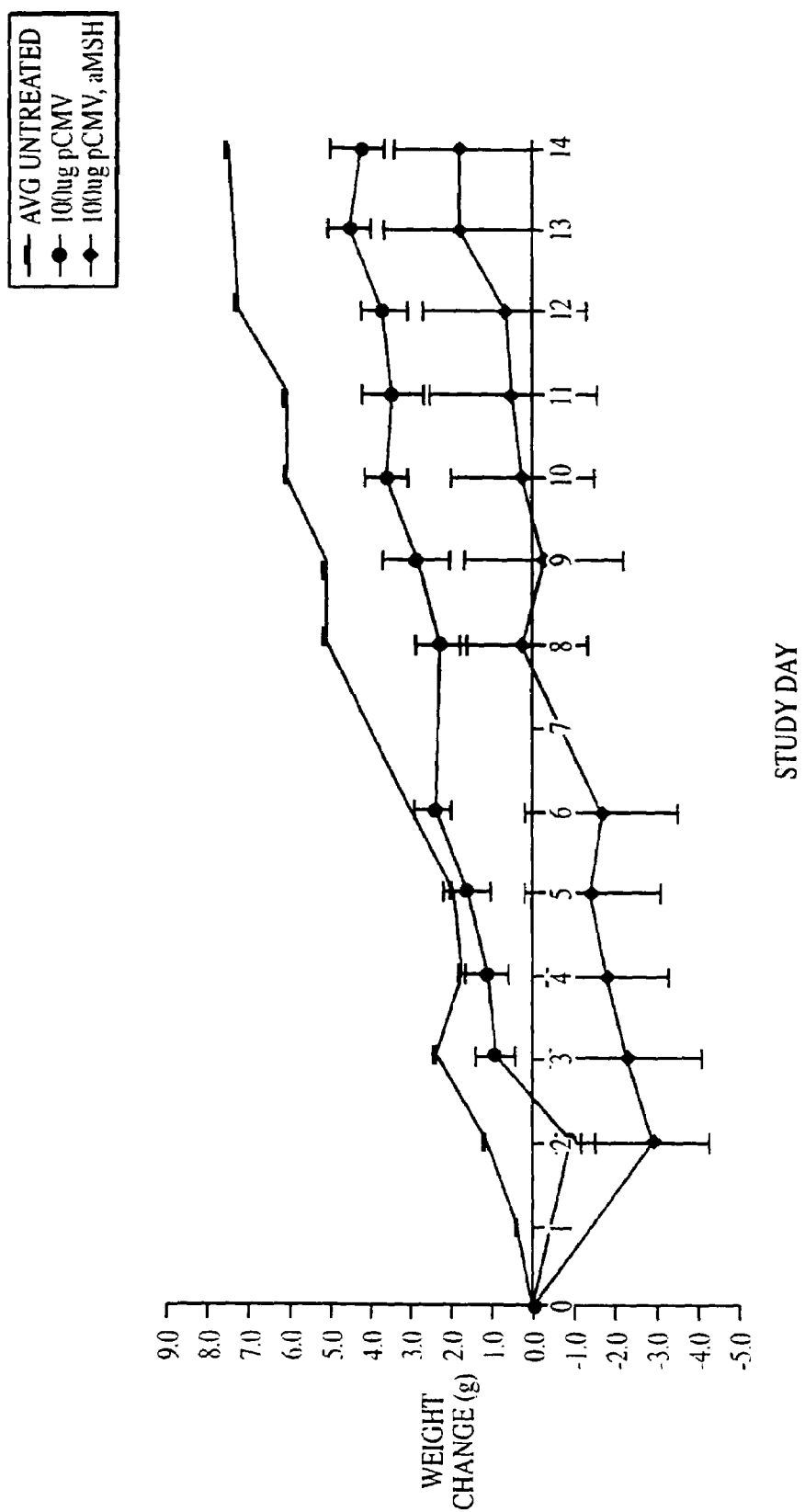
FIG. 18B depicts the results of an experiment in which a miniPOMC vector was used to treat obesity.

Use of an Alpha-MSH Analog and an Alpha-MSH Encoding Nucleic Acid in a Murine Model of Obesity Leptin –/– mice were used as a model of mammalian obesity to evaluate the effectiveness of an α-MSH analog and an α-MSH encoding nucleic acid to treat the condition. As shown in FIG. 18A, leptin –/– mice treated with an α-MSH(4-13) analog (as described in Example 6) showed a decrease in weight gain, as compared to untreated mice. Leptin –/– obese mice were administered (either intranasally, intrarectally, or subcutaneously) with 1 μg of the α-MSH(4-13) analog daily for three weeks. As shown in FIG. 18B, a reduction in weight gain was also seen in leptin –/– mice that were provided intranasal administrations of 100 μg of the pCMV-miniPOMC expression vector at six day intervals.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A nucleic acid comprising a nucleotide sequence encoding a fusion polypeptide comprising the amino acid sequence MPRSCCSRSGALLLALLLQASMEVRG-WCLESSQCQDLTTESNLLECIRACKPR EGKRSYSME-HFRWGKPV (SEQ ID NO:42).

2. A nucleic acid comprising a nucleotide sequence encoding a fusion polypeptide comprising the amino acid sequence MPRSCCSRSGALLLALLLQASMEVRG-WCLESSQCQDLTTESNLLECIRACKPR EGKRSYSME-HFRWGKPVG (SEQ ID NO:47).

3. A nucleic acid comprising a nucleotide sequence encoding a fusion polypeptide comprising the amino acid sequence MPRSCCSRSGALLLALLLQASMEVRG-WCLESSQCQDLTTESNLLECIRACKPR EGKRSYSME-HFRWGKPVGKK (SEQ ID NO:49).

4. A nucleic acid comprising a nucleotide sequence encoding a fusion polypeptide comprising the amino acid sequence MPRSCCSRSGALLLALLLQASMEVRG-WCLESSQCQDLTTESNLLECIRACKPR EGKRSYSME-HFRWGKPVGKKR (SEQ ID NO:51).

5. An expression vector comprising the nucleic acid of claim 1.

6. An expression vector comprising the nucleic acid of claim 2.

7. An expression vector comprising the nucleic acid of claim 3.

8. An expression vector comprising the nucleic acid of claim 4.

9. A fusion polypeptide comprising the amino acid sequence MPRSCCSRSGALLLALLLQASMEVRGWCLESSQCQDLTTESNLLECIRACKPREGKRSY SMEHFRWGKPV (SEQ ID NO:42).

10. A fusion polypeptide comprising the amino acid sequence MPRSCCSRSGALLLALLLQASMEVRGWCLESSQCQDLTTESNLLECIRACKPREGKRSY SMEHFRWGKPVG (SEQ ID NO:47).

11. A fusion polypeptide comprising the amino acid sequence MPRSCCSRSGALLLALLLQASMEVRGWCLESSQCQDLTTESNLLECIRACKPREGKRSY SMEHFRWGKPVGKK (SEQ ID NO:49).

12. A fusion polypeptide comprising the amino acid sequence MPRSCCSRSGALLLALLLQASMEVRGWCLESSQCQDLTTESNLLECIRACKPREGKRSY SMEHFRWGKPVGKKR (SEQ ID NO:51).

* * * * *

SEQUENCE LISTING

<160> NUMBER OF SEQ ID NOS: 83

<210> SEQ ID NO 1
<211> LENGTH: 13
<212> TYPE: PRT
<213> ORGANISM: Homo sapiens

<400> SEQUENCE: 1

Ser Tyr Ser Met Glu His Phe Arg Trp Gly Lys Pro Val
 1               5                   10

<210> SEQ ID NO 2

```
<211> LENGTH: 3
<212> TYPE: PRT
<213> ORGANISM: Homo sapiens

<400> SEQUENCE: 2

Lys Pro Val
 1

<210> SEQ ID NO 3
<211> LENGTH: 26
<212> TYPE: PRT
<213> ORGANISM: Homo sapiens

<400> SEQUENCE: 3

Met Pro Arg Ser Cys Cys Ser Arg Ser Gly Ala Leu Leu Leu Ala Leu
 1               5                  10                  15

Leu Leu Gln Ala Ser Met Glu Val Arg Gly
            20                  25

<210> SEQ ID NO 4
<211> LENGTH: 25
<212> TYPE: PRT
<213> ORGANISM: Homo sapiens

<400> SEQUENCE: 4

Met Ala Ile Ser Gly Val Pro Val Leu Gly Phe Phe Ile Ile Ala Val
 1               5                  10                  15

Leu Met Ser Ala Gln Glu Ser Trp Ala
            20                  25

<210> SEQ ID NO 5
<211> LENGTH: 26
<212> TYPE: PRT
<213> ORGANISM: Homo sapiens

<400> SEQUENCE: 5

Trp Cys Leu Glu Ser Ser Gln Cys Gln Asp Leu Thr Thr Glu Ser Asn
 1               5                  10                  15

Leu Leu Glu Cys Ile Arg Ala Cys Lys Pro
            20                  25

<210> SEQ ID NO 6
<211> LENGTH: 5
<212> TYPE: PRT
<213> ORGANISM: Homo sapiens

<400> SEQUENCE: 6

Lys Phe Glu Arg Gln
 1               5

<210> SEQ ID NO 7
<211> LENGTH: 5
<212> TYPE: PRT
<213> ORGANISM: Homo sapiens

<400> SEQUENCE: 7

Gln Arg Glu Phe Lys
 1               5

<210> SEQ ID NO 8
<211> LENGTH: 23
<212> TYPE: PRT
<213> ORGANISM: Homo sapiens
```

-continued

```
<400> SEQUENCE: 8

Gly Arg Thr Gln Asp Glu Asn Pro Val Val His Phe Phe Lys Asn Ile
1               5                   10                  15

Val Thr Pro Arg Thr Pro Pro
            20

<210> SEQ ID NO 9
<211> LENGTH: 22
<212> TYPE: PRT
<213> ORGANISM: Homo sapiens

<400> SEQUENCE: 9

Ala Val Tyr Val Tyr Ile Tyr Phe Asn Thr Trp Thr Thr Cys Gln Phe
1               5                   10                  15

Ile Ala Phe Pro Phe Lys
            20

<210> SEQ ID NO 10
<211> LENGTH: 17
<212> TYPE: PRT
<213> ORGANISM: Homo sapiens

<400> SEQUENCE: 10

Thr Thr Asn Val Arg Leu Lys Gln Gln Trp Val Asp Tyr Asn Leu Lys
1               5                   10                  15

Trp

<210> SEQ ID NO 11
<211> LENGTH: 20
<212> TYPE: PRT
<213> ORGANISM: Homo sapiens

<400> SEQUENCE: 11

Gln Ile Val Thr Thr Asn Val Arg Leu Lys Gln Gln Trp Val Asp Tyr
1               5                   10                  15

Asn Leu Lys Trp
            20

<210> SEQ ID NO 12
<211> LENGTH: 7
<212> TYPE: PRT
<213> ORGANISM: Homo sapiens

<400> SEQUENCE: 12

Gln Trp Val Asp Tyr Asn Leu
1               5

<210> SEQ ID NO 13
<211> LENGTH: 18
<212> TYPE: PRT
<213> ORGANISM: Homo sapiens

<400> SEQUENCE: 13

Gly Gly Val Lys Lys Ile His Ile Pro Ser Glu Lys Ile Trp Arg Pro
1               5                   10                  15

Asp Leu

<210> SEQ ID NO 14
<211> LENGTH: 12
<212> TYPE: PRT
<213> ORGANISM: Homo sapiens
```

-continued

```
<400> SEQUENCE: 14

Ala Ile Val Lys Phe Thr Lys Val Leu Leu Gln Tyr
 1               5                  10

<210> SEQ ID NO 15
<211> LENGTH: 20
<212> TYPE: PRT
<213> ORGANISM: Homo sapiens

<400> SEQUENCE: 15

Trp Thr Pro Pro Ala Ile Phe Lys Ser Tyr Cys Glu Ile Ile Val Thr
 1               5                  10                  15

His Phe Pro Phe
            20

<210> SEQ ID NO 16
<211> LENGTH: 13
<212> TYPE: PRT
<213> ORGANISM: Homo sapiens

<400> SEQUENCE: 16

Met Lys Leu Gly Thr Trp Thr Tyr Asp Gly Ser Val Val
 1               5                  10

<210> SEQ ID NO 17
<211> LENGTH: 13
<212> TYPE: PRT
<213> ORGANISM: Homo sapiens

<400> SEQUENCE: 17

Met Lys Leu Gly Ile Trp Thr Tyr Asp Gly Ser Val Val
 1               5                  10

<210> SEQ ID NO 18
<211> LENGTH: 9
<212> TYPE: PRT
<213> ORGANISM: Homo sapiens

<400> SEQUENCE: 18

Trp Thr Tyr Asp Gly Ser Val Val Ala
 1               5

<210> SEQ ID NO 19
<211> LENGTH: 17
<212> TYPE: PRT
<213> ORGANISM: Homo sapiens

<400> SEQUENCE: 19

Ser Cys Cys Pro Asp Thr Pro Tyr Leu Asp Ile Thr Tyr His Phe Val
 1               5                  10                  15

Met

<210> SEQ ID NO 20
<211> LENGTH: 18
<212> TYPE: PRT
<213> ORGANISM: Homo sapiens

<400> SEQUENCE: 20

Asp Thr Pro Tyr Leu Asp Ile Thr Tyr His Phe Val Met Gln Arg Leu
 1               5                  10                  15

Pro Leu
```

```
<210> SEQ ID NO 21
<211> LENGTH: 21
<212> TYPE: PRT
<213> ORGANISM: Homo sapiens

<400> SEQUENCE: 21

Phe Ile Val Asn Val Ile Ile Pro Cys Leu Leu Phe Ser Phe Leu Thr
1               5                   10                  15

Gly Leu Val Phe Tyr
            20

<210> SEQ ID NO 22
<211> LENGTH: 13
<212> TYPE: PRT
<213> ORGANISM: Homo sapiens

<400> SEQUENCE: 22

Leu Leu Val Ile Val Glu Leu Ile Pro Ser Thr Ser Ser
1               5                   10

<210> SEQ ID NO 23
<211> LENGTH: 19
<212> TYPE: PRT
<213> ORGANISM: Homo sapiens

<400> SEQUENCE: 23

Ser Thr His Val Met Pro Asn Trp Val Arg Lys Val Phe Ile Asp Thr
1               5                   10                  15

Ile Pro Asn

<210> SEQ ID NO 24
<211> LENGTH: 18
<212> TYPE: PRT
<213> ORGANISM: Homo sapiens

<400> SEQUENCE: 24

Asn Trp Val Arg Lys Val Phe Ile Asp Thr Ile Pro Asn Ile Met Phe
1               5                   10                  15

Phe Ser

<210> SEQ ID NO 25
<211> LENGTH: 18
<212> TYPE: PRT
<213> ORGANISM: Homo sapiens

<400> SEQUENCE: 25

Ile Pro Asn Ile Met Phe Phe Ser Thr Met Lys Arg Pro Ser Arg Glu
1               5                   10                  15

Lys Gln

<210> SEQ ID NO 26
<211> LENGTH: 16
<212> TYPE: PRT
<213> ORGANISM: Homo sapiens

<400> SEQUENCE: 26

Ala Ala Ala Glu Trp Lys Tyr Val Ala Met Val Met Asp His Ile Leu
1               5                   10                  15

<210> SEQ ID NO 27
<211> LENGTH: 19
<212> TYPE: PRT
<213> ORGANISM: Homo sapiens
```

```
<400> SEQUENCE: 27

Ile Ile Gly Thr Leu Ala Val Phe Ala Gly Arg Leu Ile Glu Leu Asn
1               5                   10                  15

Gln Gln Gly

<210> SEQ ID NO 28
<211> LENGTH: 20
<212> TYPE: PRT
<213> ORGANISM: Homo sapiens

<400> SEQUENCE: 28

Gly Gln Thr Ile Glu Trp Ile Phe Ile Asp Pro Glu Ala Phe Thr Glu
1               5                   10                  15

Asn Gly Glu Trp
            20

<210> SEQ ID NO 29
<211> LENGTH: 20
<212> TYPE: PRT
<213> ORGANISM: Homo sapiens

<400> SEQUENCE: 29

Met Ala His Tyr Asn Arg Val Pro Ala Leu Pro Phe Pro Gly Asp Pro
1               5                   10                  15

Arg Pro Tyr Leu
            20

<210> SEQ ID NO 30
<211> LENGTH: 15
<212> TYPE: PRT
<213> ORGANISM: Homo sapiens

<400> SEQUENCE: 30

Leu Asn Ser Lys Ile Ala Phe Lys Ile Val Ser Gln Glu Pro Ala
1               5                   10                  15

<210> SEQ ID NO 31
<211> LENGTH: 15
<212> TYPE: PRT
<213> ORGANISM: Homo sapiens

<400> SEQUENCE: 31

Thr Pro Met Phe Leu Leu Ser Arg Asn Thr Gly Glu Val Arg Thr
1               5                   10                  15

<210> SEQ ID NO 32
<211> LENGTH: 21
<212> TYPE: PRT
<213> ORGANISM: Homo sapiens

<400> SEQUENCE: 32

Ser Gln Arg His Gly Ser Lys Tyr Leu Ala Thr Ala Ser Thr Met Asp
1               5                   10                  15

His Ala Arg His Gly
            20

<210> SEQ ID NO 33
<211> LENGTH: 20
<212> TYPE: PRT
<213> ORGANISM: Homo sapiens

<400> SEQUENCE: 33
```

```
Arg Asp Thr Gly Ile Leu Asp Ser Ile Gly Arg Phe Phe Gly Asp
 1               5                  10                  15

Arg Gly Ala Pro
            20

<210> SEQ ID NO 34
<211> LENGTH: 20
<212> TYPE: PRT
<213> ORGANISM: Homo sapiens

<400> SEQUENCE: 34

Gln Lys Ser His Gly Arg Thr Gln Asp Glu Asn Pro Val Val His Phe
 1               5                  10                  15

Phe Lys Asn Ile
            20

<210> SEQ ID NO 35
<211> LENGTH: 14
<212> TYPE: PRT
<213> ORGANISM: Homo sapiens

<400> SEQUENCE: 35

Asp Glu Asn Pro Val Val His Phe Phe Lys Asn Ile Val Thr
 1               5                  10

<210> SEQ ID NO 36
<211> LENGTH: 15
<212> TYPE: PRT
<213> ORGANISM: Homo sapiens

<400> SEQUENCE: 36

Glu Asn Pro Val Val His Phe Phe Lys Asn Ile Val Thr Pro Arg
 1               5                  10                  15

<210> SEQ ID NO 37
<211> LENGTH: 13
<212> TYPE: PRT
<213> ORGANISM: Homo sapiens

<400> SEQUENCE: 37

His Phe Phe Lys Asn Ile Val Thr Pro Arg Thr Pro Pro
 1               5                  10

<210> SEQ ID NO 38
<211> LENGTH: 14
<212> TYPE: PRT
<213> ORGANISM: Homo sapiens

<400> SEQUENCE: 38

Lys Gly Phe Lys Gly Val Asp Ala Gln Gly Thr Leu Ser Lys
 1               5                  10

<210> SEQ ID NO 39
<211> LENGTH: 20
<212> TYPE: PRT
<213> ORGANISM: Homo sapiens

<400> SEQUENCE: 39

Val Asp Ala Gln Gly Thr Leu Ser Lys Ile Phe Lys Leu Gly Gly Arg
 1               5                  10                  15

Asp Ser Arg Ser
            20
```

```
<210> SEQ ID NO 40
<211> LENGTH: 52
<212> TYPE: PRT
<213> ORGANISM: Homo sapiens

<400> SEQUENCE: 40

Met Pro Arg Ser Cys Cys Ser Arg Ser Gly Ala Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro
    50

<210> SEQ ID NO 41
<211> LENGTH: 5
<212> TYPE: PRT
<213> ORGANISM: Homo sapiens

<400> SEQUENCE: 41

Glu His Phe Arg Trp
1               5

<210> SEQ ID NO 42
<211> LENGTH: 70
<212> TYPE: PRT
<213> ORGANISM: Homo sapiens

<400> SEQUENCE: 42

Met Pro Arg Ser Cys Cys Ser Arg Ser Gly Ala Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro Arg Glu Gly Lys Arg Ser Tyr Ser Met Glu His Phe
    50                  55                  60

Arg Trp Gly Lys Pro Val
65                  70

<210> SEQ ID NO 43
<211> LENGTH: 245
<212> TYPE: DNA
<213> ORGANISM: Homo sapiens
<220> FEATURE:
<221> NAME/KEY: CDS
<222> LOCATION: (21)...(230)

<400> SEQUENCE: 43
aagcttgcgc tgcctggaag atg ccg aga tcg tgc tgc agc cgc tcg ggg gcc      53
                     Met Pro Arg Ser Cys Cys Ser Arg Ser Gly Ala
                     1               5                   10 ctg ttg ctg gcc ttg ctg ctt cag gcc tcc atg gaa gtg cgt ggc tgg       101
Leu Leu Leu Ala Leu Leu Leu Gln Ala Ser Met Glu Val Arg Gly Trp
            15                  20                  25 tgc ctg gag agc agc cag tgt cag gac ctc acc acg gaa agc aac ctg       149
Cys Leu Glu Ser Ser Gln Cys Gln Asp Leu Thr Thr Glu Ser Asn Leu
            30                  35                  40 ctg gag tgc atc cgg gcc tgc aag ccc cgc gag ggc aag cgc tcc tac       197
Leu Glu Cys Ile Arg Ala Cys Lys Pro Arg Glu Gly Lys Arg Ser Tyr
```

```
                    45                  50                  55
tcc atg gag cac ttc cgc tgg ggc aag ccg gtg taaggatccc tcgag         245
Ser Met Glu His Phe Arg Trp Gly Lys Pro Val
 60                  65                  70

<210> SEQ ID NO 44
<211> LENGTH: 5
<212> TYPE: PRT
<213> ORGANISM: Artificial Sequence
<220> FEATURE:
<223> OTHER INFORMATION: linker sequence

<400> SEQUENCE: 44

Gly Gly Val Gly Gly
 1               5

<210> SEQ ID NO 45
<211> LENGTH: 4
<212> TYPE: PRT
<213> ORGANISM: Homo sapiens

<400> SEQUENCE: 45

Gly Lys Lys Arg
 1

<210> SEQ ID NO 46
<211> LENGTH: 250
<212> TYPE: DNA
<213> ORGANISM: Homo sapiens
<220> FEATURE:
<221> NAME/KEY: CDS
<222> LOCATION: (23)...(235)

<400> SEQUENCE: 46
aagcttgcgc gctgcctgga ag atg ccg aga tcg tgc tgc agc cgc tcg ggg    52
                         Met Pro Arg Ser Cys Cys Ser Arg Ser Gly
                          1               5                  10 gcc ctg ttg ctg gcc ttg ctg ctt cag gcc tcc atg gaa gtg cgt ggc    100
Ala Leu Leu Leu Ala Leu Leu Leu Gln Ala Ser Met Glu Val Arg Gly
             15                  20                  25 tgg tgc ctg gag agc agc cag tgt cag gac ctc acc acg gaa agc aac    148
Trp Cys Leu Glu Ser Ser Gln Cys Gln Asp Leu Thr Thr Glu Ser Asn
         30                  35                  40 ctg ctg gag tgc atc cgg gcc tgc aag ccc cgc gag ggc aag cgc tcc    196
Leu Leu Glu Cys Ile Arg Ala Cys Lys Pro Arg Glu Gly Lys Arg Ser
     45                  50                  55 tac tcc atg gag cac ttc cgc tgg ggc aag ccg gtg ggc taaggatccc    245
Tyr Ser Met Glu His Phe Arg Trp Gly Lys Pro Val Gly
 60                  65                  70 tcgag                                                              250

<210> SEQ ID NO 47
<211> LENGTH: 71
<212> TYPE: PRT
<213> ORGANISM: Homo sapiens

<400> SEQUENCE: 47

Met Pro Arg Ser Cys Cys Ser Arg Ser Gly Ala Leu Leu Leu Ala Leu
 1               5                  10                  15

Leu Leu Gln Ala Ser Met Glu Val Arg Gly Trp Cys Leu Glu Ser Ser
             20                  25                  30

Gln Cys Gln Asp Leu Thr Thr Glu Ser Asn Leu Leu Glu Cys Ile Arg
         35                  40                  45
```

```
Ala Cys Lys Pro Arg Glu Gly Lys Arg Ser Tyr Ser Met Glu His Phe
 50                  55                  60

Arg Trp Gly Lys Pro Val Gly
 65                  70

<210> SEQ ID NO 48
<211> LENGTH: 256
<212> TYPE: DNA
<213> ORGANISM: Homo sapiens
<220> FEATURE:
<221> NAME/KEY: CDS
<222> LOCATION: (23)...(241)

<400> SEQUENCE: 48
aagcttgcgc gctgcctgga ag atg ccg aga tcg tgc tgc agc cgc tcg ggg        52
                        Met Pro Arg Ser Cys Cys Ser Arg Ser Gly
                         1               5                  10 gcc ctg ttg ctg gcc ttg ctg ctt cag gcc tcc atg gaa gtg cgt ggc        100
Ala Leu Leu Leu Ala Leu Leu Leu Gln Ala Ser Met Glu Val Arg Gly
             15                  20                  25 tgg tgc ctg gag agc agc cag tgt cag gac ctc acc acg gaa agc aac        148
Trp Cys Leu Glu Ser Ser Gln Cys Gln Asp Leu Thr Thr Glu Ser Asn
         30                  35                  40 ctg ctg gag tgc atc cgg gcc tgc aag ccc cgc gag ggc aag cgc tcc        196
Leu Leu Glu Cys Ile Arg Ala Cys Lys Pro Arg Glu Gly Lys Arg Ser
     45                  50                  55 tac tcc atg gag cac ttc cgc tgg ggc aag ccg gtg ggc aag aag            241
Tyr Ser Met Glu His Phe Arg Trp Gly Lys Pro Val Gly Lys Lys
 60                  65                  70 taaggatccc tcgag                                                       256

<210> SEQ ID NO 49
<211> LENGTH: 73
<212> TYPE: PRT
<213> ORGANISM: Homo sapiens

<400> SEQUENCE: 49

Met Pro Arg Ser Cys Cys Ser Arg Ser Gly Ala Leu Leu Leu Ala Leu
 1               5                  10                  15

Leu Leu Gln Ala Ser Met Glu Val Arg Gly Trp Cys Leu Glu Ser Ser
             20                  25                  30

Gln Cys Gln Asp Leu Thr Thr Glu Ser Asn Leu Leu Glu Cys Ile Arg
         35                  40                  45

Ala Cys Lys Pro Arg Glu Gly Lys Arg Ser Tyr Ser Met Glu His Phe
     50                  55                  60

Arg Trp Gly Lys Pro Val Gly Lys Lys
 65                  70

<210> SEQ ID NO 50
<211> LENGTH: 259
<212> TYPE: DNA
<213> ORGANISM: Homo sapiens
<220> FEATURE:
<221> NAME/KEY: CDS
<222> LOCATION: (23)...(244)

<400> SEQUENCE: 50
aagcttgcgc gctgcctgga ag atg ccg aga tcg tgc tgc agc cgc tcg ggg        52
                        Met Pro Arg Ser Cys Cys Ser Arg Ser Gly
                         1               5                  10 gcc ctg ttg ctg gcc ttg ctg ctt cag gcc tcc atg gaa gtg cgt ggc        100
```

```
                                                                                       -continued Ala Leu Leu Leu Ala Leu Leu Leu Gln Ala Ser Met Glu Val Arg Gly
                15                  20                  25 tgg tgc ctg gag agc agc cag tgt cag gac ctc acc acg gaa agc aac        148
Trp Cys Leu Glu Ser Ser Gln Cys Gln Asp Leu Thr Thr Glu Ser Asn
             30                  35                  40 ctg ctg gag tgc atc cgg gcc tgc aag ccc cgc gag ggc aag cgc tcc        196
Leu Leu Glu Cys Ile Arg Ala Cys Lys Pro Arg Glu Gly Lys Arg Ser
     45                  50                  55 tac tcc atg gag cac ttc cgc tgg ggc aag ccg gtg ggc aag aag cgg        244
Tyr Ser Met Glu His Phe Arg Trp Gly Lys Pro Val Gly Lys Lys Arg
 60                  65                  70 taaggatccc tcgag                                                        259

<210> SEQ ID NO 51
<211> LENGTH: 74
<212> TYPE: PRT
<213> ORGANISM: Homo sapiens

<400> SEQUENCE: 51

Met Pro Arg Ser Cys Cys Ser Arg Ser Gly Ala Leu Leu Leu Ala Leu
 1               5                  10                  15

Leu Leu Gln Ala Ser Met Glu Val Arg Gly Trp Cys Leu Glu Ser Ser
                20                  25                  30

Gln Cys Gln Asp Leu Thr Thr Glu Ser Asn Leu Leu Glu Cys Ile Arg
         35                  40                  45

Ala Cys Lys Pro Arg Glu Gly Lys Arg Ser Tyr Ser Met Glu His Phe
     50                  55                  60

Arg Trp Gly Lys Pro Val Gly Lys Lys Arg
 65                  70

<210> SEQ ID NO 52
<211> LENGTH: 18
<212> TYPE: PRT
<213> ORGANISM: Mus musculus

<400> SEQUENCE: 52

Met Lys Trp Val Thr Phe Leu Leu Leu Leu Phe Val Ser Gly Ser Ala
 1               5                  10                  15

Phe Ser

<210> SEQ ID NO 53
<211> LENGTH: 18
<212> TYPE: PRT
<213> ORGANISM: Homo sapiens

<400> SEQUENCE: 53

Met Lys Trp Val Thr Phe Ile Ser Leu Leu Phe Leu Phe Ser Ser Ala
 1               5                  10                  15

Tyr Ser

<210> SEQ ID NO 54
<211> LENGTH: 6
<212> TYPE: PRT
<213> ORGANISM: Homo sapiens

<400> SEQUENCE: 54

Arg Gly Val Phe Arg Arg
 1               5

<210> SEQ ID NO 55
```

```
<211> LENGTH: 195
<212> TYPE: PRT
<213> ORGANISM: Mus musculus

<400> SEQUENCE: 55

Glu Ala His Lys Ser Glu Ile Ala His Arg Tyr Asn Asp Leu Gly Glu
  1               5                  10                  15

Gln His Phe Lys Gly Leu Val Leu Ile Ala Phe Ser Gln Tyr Leu Gln
             20                  25                  30

Lys Cys Ser Tyr Asp Glu His Ala Lys Leu Val Gln Glu Val Thr Asp
         35                  40                  45

Phe Ala Lys Thr Cys Val Ala Asp Glu Ser Ala Ala Asn Cys Asp Lys
     50                  55                  60

Ser Leu His Thr Leu Phe Gly Asp Lys Leu Cys Ala Ile Pro Asn Leu
 65                  70                  75                  80

Arg Glu Asn Tyr Gly Glu Leu Ala Asp Cys Cys Thr Lys Gln Glu Pro
                 85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg
        195

<210> SEQ ID NO 56
<211> LENGTH: 195
<212> TYPE: PRT
<213> ORGANISM: Homo sapiens

<400> SEQUENCE: 56

Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys
        195

<210> SEQ ID NO 57
<211> LENGTH: 5
<212> TYPE: PRT
<213> ORGANISM: Artificial Sequence
<220> FEATURE:
<223> OTHER INFORMATION: linker sequence

<400> SEQUENCE: 57

Gly Gly Tyr Gly Gly
1               5

<210> SEQ ID NO 58
<211> LENGTH: 4
<212> TYPE: PRT
<213> ORGANISM: Artificial Sequence
<220> FEATURE:
<223> OTHER INFORMATION: furin site

<400> SEQUENCE: 58

Arg Ile Arg Arg
1

<210> SEQ ID NO 59
<211> LENGTH: 241
<212> TYPE: PRT
<213> ORGANISM: Homo sapiens

<400> SEQUENCE: 59

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175
```

```
Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gly Gly Tyr Gly Gly
        210                 215                 220

Arg Ile Arg Arg Ser Tyr Ser Met Glu His Phe Arg Trp Gly Lys Pro
225                 230                 235                 240

Val

<210> SEQ ID NO 60
<211> LENGTH: 268
<212> TYPE: PRT
<213> ORGANISM: Homo sapiens

<400> SEQUENCE: 60

Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gly Gly Tyr Gly Gly
    210                 215                 220

Arg Ile Arg Arg Ser Tyr Ser Met Glu His Phe Arg Trp Asp Glu Gly
225                 230                 235                 240

Lys Ala Ser Ser Ala Lys Gly Gly Tyr Gly Gly Arg Ile Arg Arg Ser
                245                 250                 255

Tyr Ser Met Glu His Phe Arg Trp Gly Lys Pro Val
            260                 265

<210> SEQ ID NO 61
<211> LENGTH: 241
<212> TYPE: PRT
<213> ORGANISM: Mus musculus
```

<400> SEQUENCE: 61

```
Met Lys Trp Val Thr Phe Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gly Gly Tyr Gly Gly
210                 215                 220

Arg Ile Arg Arg Ser Tyr Ser Met Glu His Phe Arg Trp Gly Lys Pro
225                 230                 235                 240

Val
```

<210> SEQ ID NO 62
<211> LENGTH: 14
<212> TYPE: PRT
<213> ORGANISM: Homo sapiens

<400> SEQUENCE: 62

```
Ser Tyr Ser Met Glu His Phe Arg Trp Gly Lys Pro Val Gly
1               5                   10
```

<210> SEQ ID NO 63
<211> LENGTH: 16
<212> TYPE: PRT
<213> ORGANISM: Homo sapiens

<400> SEQUENCE: 63

```
Ser Tyr Ser Met Glu His Phe Arg Trp Gly Lys Pro Val Gly Lys Lys
1               5                   10                  15
```

<210> SEQ ID NO 64
<211> LENGTH: 17
<212> TYPE: PRT
<213> ORGANISM: Homo sapiens

<400> SEQUENCE: 64

Ser Tyr Ser Met Glu His Phe Arg Trp Gly Lys Pro Val Gly Lys Lys
1               5                   10                  15

Arg

<210> SEQ ID NO 65
<211> LENGTH: 10
<212> TYPE: PRT
<213> ORGANISM: Homo sapiens

<400> SEQUENCE: 65

Ser Gly Gly Gly Gly Ser Gly Gly Gly Gly
1               5                   10

<210> SEQ ID NO 66
<211> LENGTH: 11
<212> TYPE: PRT
<213> ORGANISM: Homo sapiens

<400> SEQUENCE: 66

Gly Gly Gly Gly Ser Gly Gly Gly Gly Ser
1               5                   10

<210> SEQ ID NO 67
<211> LENGTH: 20
<212> TYPE: PRT
<213> ORGANISM: Homo sapiens

<400> SEQUENCE: 67

Ser Gly Gly Gly Gly Ser Gly Gly Gly Ser Gly Gly Gly Gly Ser
1               5                   10                  15

Gly Gly Gly Gly
            20

<210> SEQ ID NO 68
<211> LENGTH: 17
<212> TYPE: PRT
<213> ORGANISM: Homo sapiens

<400> SEQUENCE: 68

Ser Ser Ser Ser Gly Ser Ser Ser Gly Ser Ser Ser Gly Ser
1               5                   10                  15

Pro

<210> SEQ ID NO 69
<211> LENGTH: 17
<212> TYPE: PRT
<213> ORGANISM: Homo sapiens

<400> SEQUENCE: 69

Ser Tyr Ser Met Glu His Phe Arg Trp Gly Lys Pro Val Arg Ser Lys
1               5                   10                  15

Arg

<210> SEQ ID NO 70
<211> LENGTH: 242
<212> TYPE: PRT
<213> ORGANISM: Homo sapiens

<400> SEQUENCE: 70

Met Lys Trp Val Thr Phe Ile Ser Leu Leu Phe Leu Phe Ser Ser Ala
1               5                   10                  15

-continued

```
Tyr Ser Arg Gly Val Phe Arg Arg Asp Ala His Lys Ser Glu Val Ala
         20                  25                  30

His Arg Phe Lys Asp Leu Gly Glu Glu Asn Phe Lys Ala Leu Val Leu
     35                  40                  45

Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gly Tyr Gly Gly
        210                 215                 220

Arg Ile Arg Arg Ser Tyr Ser Met Glu His Phe Arg Trp Gly Lys Pro
225                 230                 235                 240

Val Gly
```

<210> SEQ ID NO 71
<211> LENGTH: 244
<212> TYPE: PRT
<213> ORGANISM: Homo sapiens

<400> SEQUENCE: 71

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
         20                  25                  30

His Arg Phe Lys Asp Leu Gly Glu Glu Asn Phe Lys Ala Leu Val Leu
     35                  40                  45

Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140
```

```
Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gly Gly Tyr Gly Gly
    210                 215                 220

Arg Ile Arg Arg Ser Tyr Ser Met Glu His Phe Arg Trp Gly Lys Pro
225                 230                 235                 240

Val Gly Lys Lys

<210> SEQ ID NO 72
<211> LENGTH: 245
<212> TYPE: PRT
<213> ORGANISM: Homo sapiens

<400> SEQUENCE: 72

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gly Gly Tyr Gly Gly
    210                 215                 220

Arg Ile Arg Arg Ser Tyr Ser Met Glu His Phe Arg Trp Gly Lys Pro
225                 230                 235                 240

Val Gly Lys Lys Arg
                245

<210> SEQ ID NO 73
<211> LENGTH: 245
```

```
<212> TYPE: PRT
<213> ORGANISM: Homo sapiens

<400> SEQUENCE: 73

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gly Gly Tyr Gly Gly
    210                 215                 220

Arg Ile Arg Arg Ser Tyr Ser Met Glu His Phe Arg Trp Gly Lys Pro
225                 230                 235                 240

Val Arg Ser Lys Arg
                245

<210> SEQ ID NO 74
<211> LENGTH: 242
<212> TYPE: PRT
<213> ORGANISM: Homo sapiens

<400> SEQUENCE: 74

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95
```

```
Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
            115                 120                 125

His Lys Asp Asp Asn Pro Ser Leu Pro Pro Phe Glu Arg Pro Glu Ala
        130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gly Gly Tyr Gly Gly
    210                 215                 220

Arg Ile Arg Arg Ser Tyr Ser Met Glu His Phe Arg Trp Gly Lys Pro
225                 230                 235                 240

Val Gly

<210> SEQ ID NO 75
<211> LENGTH: 244
<212> TYPE: PRT
<213> ORGANISM: Homo sapiens

<400> SEQUENCE: 75

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
                20                  25                  30

His Arg Tyr Asn Asp Leu Gly Glu Gln His Phe Lys Gly Leu Val Leu
            35                  40                  45

Ile Ala Phe Ser Gln Tyr Leu Gln Lys Cys Ser Tyr Asp Glu His Ala
        50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
            115                 120                 125

His Lys Asp Asp Asn Pro Ser Leu Pro Pro Phe Glu Arg Pro Glu Ala
        130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
        195                 200                 205

Val Lys Glu Lys Ala Leu Val Ser Ser Val Arg Gly Gly Tyr Gly Gly
    210                 215                 220
```

```
Arg Ile Arg Arg Ser Tyr Ser Met Glu His Phe Arg Trp Gly Lys Pro
225                 230                 235                 240

Val Gly Lys Lys
```

<210> SEQ ID NO 76
<211> LENGTH: 245
<212> TYPE: PRT
<213> ORGANISM: Homo sapiens

<400> SEQUENCE: 76

```
Met Lys Trp Val Thr Phe Leu Leu Leu Phe Val Ser Gly Ser Ala
1               5                   10                  15

Phe Ser Arg Gly Val Phe Arg Glu Ala His Lys Ser Glu Ile Ala
                20                  25                  30

His Arg Tyr Asn Asp Leu Gly Glu Gln His Phe Lys Gly Leu Val Leu
            35                  40                  45

Ile Ala Phe Ser Gln Tyr Leu Gln Lys Cys Ser Tyr Asp Glu His Ala
50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
                115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
                180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gly Gly Tyr Gly Gly
    210                 215                 220

Arg Ile Arg Arg Ser Tyr Ser Met Glu His Phe Arg Trp Gly Lys Pro
225                 230                 235                 240

Val Gly Lys Lys Arg
                245
```

<210> SEQ ID NO 77
<211> LENGTH: 245
<212> TYPE: PRT
<213> ORGANISM: Homo sapiens

<400> SEQUENCE: 77

```
Met Lys Trp Val Thr Phe Leu Leu Leu Phe Val Ser Gly Ser Ala
1               5                   10                  15

Phe Ser Arg Gly Val Phe Arg Glu Ala His Lys Ser Glu Ile Ala
                20                  25                  30

His Arg Tyr Asn Asp Leu Gly Glu Gln His Phe Lys Gly Leu Val Leu
            35                  40                  45

Ile Ala Phe Ser Gln Tyr Leu Gln Lys Cys Ser Tyr Asp Glu His Ala
```

```
                50                  55                  60
Lys Leu Val Gln Glu Val Thr Asp Phe Ala Lys Thr Cys Val Ala Asp
 65                  70                  75                  80

Glu Ser Ala Ala Asn Cys Asp Lys Ser Leu His Thr Leu Phe Gly Asp
                 85                  90                  95

Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
                115                 120                 125

His Lys Asp Asp Asn Pro Ser Leu Pro Pro Phe Glu Arg Pro Glu Ala
130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
                180                 185                 190

Cys Ala Glu Ala Asp Lys Glu Ser Cys Leu Thr Pro Lys Leu Asp Gly
                195                 200                 205

Val Lys Glu Lys Ala Leu Val Ser Ser Val Arg Gly Gly Tyr Gly Gly
                210                 215                 220

Arg Ile Arg Arg Ser Tyr Ser Met Glu His Phe Arg Trp Gly Lys Pro
225                 230                 235                 240

Val Arg Ser Lys Arg
                245

<210> SEQ ID NO 78
<211> LENGTH: 74
<212> TYPE: PRT
<213> ORGANISM: Homo sapiens

<400> SEQUENCE: 78

Met Pro Arg Ser Cys Cys Ser Arg Ser Gly Ala Leu Leu Leu Ala Leu
  1               5                  10                  15

Leu Leu Gln Ala Ser Met Glu Val Arg Gly Trp Cys Leu Glu Ser Ser
                 20                  25                  30

Gln Cys Gln Asp Leu Thr Thr Glu Ser Asn Leu Leu Glu Cys Ile Arg
                 35                  40                  45

Ala Cys Lys Pro Arg Glu Gly Lys Arg Ser Tyr Ser Met Glu His Phe
 50                  55                  60

Arg Trp Gly Lys Pro Val Arg Ser Lys Arg
 65                  70

<210> SEQ ID NO 79
<211> LENGTH: 259
<212> TYPE: DNA
<213> ORGANISM: Homo sapiens
<220> FEATURE:
<221> NAME/KEY: CDS
<222> LOCATION: (23)...(244)

<400> SEQUENCE: 79
aagcttgcgc gctgcctgga ag atg ccg aga tcg tgc tgc agc cgc tcg ggg      52
                         Met Pro Arg Ser Cys Cys Ser Arg Ser Gly
                           1               5                  10 gcc ctg ttg ctg gcc ttg ctg ctt cag gcc tcc atg gaa gtg cgt ggc     100
Ala Leu Leu Leu Ala Leu Leu Leu Gln Ala Ser Met Glu Val Arg Gly
               15                  20                  25
```

```
tgg tgc ctg gag agc agc cag tgt cag gac ctc acc acg gaa agc aac    148
Trp Cys Leu Glu Ser Ser Gln Cys Gln Asp Leu Thr Thr Glu Ser Asn
            30                  35                  40 ctg ctg gag tgc atc cgg gcc tgc aag ccc cgc gag ggc aag cgc tcc    196
Leu Leu Glu Cys Ile Arg Ala Cys Lys Pro Arg Glu Gly Lys Arg Ser
        45                  50                  55 tac tcc atg gag cac ttc cgc tgg ggc aag ccg gtg cgg tcc aag cgc    244
Tyr Ser Met Glu His Phe Arg Trp Gly Lys Pro Val Arg Ser Lys Arg
    60                  65                  70 taaggatccc tcgag                                                   259
```

<210> SEQ ID NO 80
<211> LENGTH: 4
<212> TYPE: PRT
<213> ORGANISM: Homo sapiens

<400> SEQUENCE: 80

Arg Ser Lys Arg
 1

<210> SEQ ID NO 81
<211> LENGTH: 4
<212> TYPE: PRT
<213> ORGANISM: Homo sapiens

<400> SEQUENCE: 81

Leu Ala Pro Arg
 1

<210> SEQ ID NO 82
<211> LENGTH: 236
<212> TYPE: PRT
<213> ORGANISM: Homo sapiens

<400> SEQUENCE: 82

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
```

-continued

```
              180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Leu Ala Pro Arg Ser
            210                 215                 220
Tyr Ser Met Glu His Phe Arg Trp Gly Lys Pro Val
225                 230                 235

<210> SEQ ID NO 83
<211> LENGTH: 236
<212> TYPE: PRT
<213> ORGANISM: Mus musculus

<400> SEQUENCE: 83

Met Lys Trp Val Thr Phe Leu Leu Leu Leu Phe Val Ser Gly Ser Ala
  1               5                  10                  15
Phe Ser Arg Gly Val Phe Arg Arg Glu Ala His Lys Ser Glu Ile Ala
             20                  25                  30
His Arg Tyr Asn Asp Leu Gly Glu Gln His Phe Lys Gly Leu Val Leu
         35                  40                  45
Ile Ala Phe Ser Gln Tyr Leu Gln Lys Cys Ser Tyr Asp Glu His Ala
 50                  55                  60
Lys Leu Val Gln Glu Val Thr Asp Phe Ala Lys Thr Cys Val Ala Asp
65                  70                  75                  80
Glu Ser Ala Ala Asn Cys Asp Lys Ser Leu His Thr Leu Phe Gly Asp
             85                  90                  95
Lys Leu Cys Ala Ile Pro Asn Leu Arg Glu Asn Tyr Gly Glu Leu Ala
            100                 105                 110
Asp Cys Cys Thr Lys Gln Glu Pro Glu Arg Asn Glu Cys Phe Leu Gln
            115                 120                 125
His Lys Asp Asp Asn Pro Ser Leu Pro Pro Phe Glu Arg Pro Glu Ala
            130                 135                 140
Glu Ala Met Cys Thr Ser Phe Lys Glu Asn Pro Thr Thr Phe Met Gly
145                 150                 155                 160
His Tyr Leu His Glu Val Ala Arg Arg His Pro Tyr Phe Tyr Ala Pro
                165                 170                 175
Glu Leu Leu Tyr Tyr Ala Glu Gln Tyr Asn Glu Ile Leu Thr Gln Cys
            180                 185                 190
Cys Ala Glu Ala Asp Lys Glu Ser Cys Leu Thr Pro Lys Leu Asp Gly
            195                 200                 205
Val Lys Glu Lys Ala Leu Val Ser Ser Val Arg Leu Ala Pro Arg Ser
            210                 215                 220
Tyr Ser Met Glu His Phe Arg Trp Gly Lys Pro Val
225                 230                 235
```